United States Patent
Yang et al.

(10) Patent No.: US 7,271,172 B2
(45) Date of Patent: Sep. 18, 2007

(54) PYRROLIDINE AND AZETIDINE COMPOUNDS AS CCR5 ANTAGONISTS

(75) Inventors: Hanbiao Yang, Standford, CA (US); Wieslaw Mieczyslaw Kazmierski, Durham, NC (US); Christopher Joseph Aquino, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/538,134

(22) PCT Filed: Dec. 12, 2003

(86) PCT No.: PCT/US03/39618

§ 371 (c)(1),
(2), (4) Date: Jun. 9, 2005

(87) PCT Pub. No.: WO2004/055016

PCT Pub. Date: Jul. 1, 2004

(65) Prior Publication Data

US 2006/0058284 A1    Mar. 16, 2006

Related U.S. Application Data

(60) Provisional application No. 60/433,372, filed on Dec. 13, 2002.

(51) Int. Cl.
*A61K 31/4747* (2006.01)
*A61K 31/4166* (2006.01)
*C07D 471/10* (2006.01)
*C07D 487/20* (2006.01)
*C07D 207/04* (2006.01)

(52) U.S. Cl. ............ 514/278; 514/392; 514/422; 546/16; 548/518; 548/301.4

(58) Field of Classification Search ........ 514/398, 514/278, 422, 423, 461, 392; 548/301.4, 548/524, 538, 518; 546/210, 16; 549/473, 549/505
See application file for complete search history.

(56) References Cited

U.S. PATENT DOCUMENTS 5,861,416 A    1/1999  Burkholder et al.
5,861,417 A    1/1999  Burkholder et al.

FOREIGN PATENT DOCUMENTS

WO    WO9426735    * 11/1994

OTHER PUBLICATIONS

STN search result of WO 94/26735, Burkholder et al., Nov. 1994, PCT.*
Wikipedia for hetercyclic compound, on-line edition.*
TYLE, Iontophoretic Devices for Drug Delivery, Pharmaceutical Research 3(6):318-326 (1986).

* cited by examiner

*Primary Examiner*—Rebecca Anderson
*Assistant Examiner*—Yong Chu
(74) *Attorney, Agent, or Firm*—Bonnie L. Deppenbrock

(57) ABSTRACT

The present invention relates to compounds of formula (I), or pharmaceutically acceptable derivatives thereof, useful in the treatment of CCR5-related diseases and disorders, for example, useful in the inhibition of HIV replication, the prevention or treatment of an HIV infection, and in the treatment of the resulting acquired immune deficiency syndrome (AIDS).

12 Claims, No Drawings

PYRROLIDINE AND AZETIDINE COMPOUNDS AS CCR5 ANTAGONISTS

CROSS-REFERENCE TO RELATED APPLICATIONS

This application is filed pursuant to 35 U.S.C. § 371 as a United States National Phase Application of International Application No. PCT/US2003/39618 filed Dec. 12, 2003, which claims priority from U.S. Provisional Application No. 60/433,372 filed Dec. 13, 2002.

BACKGROUND OF THE INVENTION

The human immunodeficiency virus ("HIV") is the causative agent for acquired immunodeficiency syndrome ("AIDS"), a disease characterized by the destruction of the immune system, particularly of CD4+ T-cells, with attendant susceptibility to opportunistic infections, and its precursor AIDS-related complex ("ARC"), a syndrome characterized by symptoms such as persistent generalized lymphadenopathy, fever and weight loss.

In addition to CD4, HIV requires a co-receptor for entry into target cells. The chemokine receptors function together with CD4 as co-receptors for HIV. The chemokine receptors CXCR4 and CCR5 have been identified as the main co-receptors for HIV-1. CCR5 acts as a major co-receptor for fusion and entry of macrophage-tropic HIV into host cells. These chemokine receptors are thought to play an essential role in the establishment and dissemination of an HIV infection. Therefore, CCR5 antagonists are thought to be useful as therapeutic agents active against HIV.

We have now discovered a series of small molecule nonpeptide compounds that are useful as inhibitors of HIV replication.

BRIEF DESCRIPTION OF THE INVENTION

The present invention features compounds that are useful in the inhibition of HIV replication, the prevention of infection by HIV, the treatment of infection by HIV and in the treatment of AIDS and/or ARC, either as pharmaceutically acceptable salts or pharmaceutical composition ingredients. The present invention further features methods of treating AIDS, methods of preventing infection by HIV, and methods of treating infection by HIV as monotherapy or in combination with other antivirals, anti-infectives, immunomodulators, antibiotics or vaccines. The present invention also features pharmaceutical compositions, comprising the above-mentioned compounds that are suitable for the prevention or treatment of CCR5-related diseases and conditions. The present invention further features processes for making the above-mentioned compounds.

SUMMARY OF THE INVENTION

The present invention includes compounds of formula (I)

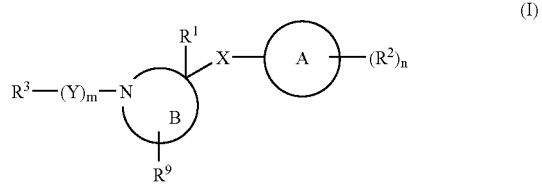

(I)

and pharmaceutically acceptable derivatives thereof, wherein:

X is a $C_{1-5}$ alkylene chain, wherein said X is optionally substituted by one or more =O, =S, alkyl, or halogen and wherein said $C_{1-5}$ alkylene chain may optionally have 0-3 heteroatoms selected from oxygen, phosphorus, sulfur, or nitrogen;

Ring A is a saturated, partially saturated, or aromatic 3-7 monocyclic or 8-10 membered bicyclic ring having one ring nitrogen and 0-4 additional heteroatoms selected from oxygen, phosphorus, sulfur, or nitrogen;

Ring B is a saturated 4 or 5 membered ring containing the depicted ring nitrogen;

$R^1$ is alkyl optionally substituted by one or more $R^7$, alkenyl optionally substituted by one or more $R^7$, alkynyl optionally substituted by one or more $R^7$, cycloalkyl optionally substituted by one or more $R^8$, heterocyclyl optionally substituted by one or more $R^8$, heteroaryl optionally substituted by one or more $R^6$, or aryl optionally substituted by one or more $R^6$; or $R^1$ and X taken together form a saturated, partially saturated or aromatic 5-6 membered ring having 0-3 heteroatoms selected from oxygen, phosphorus, sulfur, or nitrogen that is fused to Ring A;

each $R^2$ is independently selected from —$OR^0$, —C(O)—$R^0$, —S(O)$_2$—$R^0$, —C(O)—N($R^0$)$_2$, —S(O)$_2$—N($R^0$)$_2$, —(CH$_2$)$_a$—N($R^0$)(—V$_b$R$^+$), —(CH$_2$)$_a$—(—V$_b$—R$^+$), halogen, alkyl optionally substituted by one or more $R^7$, alkenyl optionally substituted by one or more $R^7$, alkynyl optionally substituted by one or more $R^7$, aryl optionally substituted by one or more $R^6$, heteroaryl optionally substituted by one or more $R^6$, cycloalkyl optionally substituted by one or more $R^8$, or heterocyclyl optionally substituted by one or more $R^8$; and two adjacent $R^2$s on Ring A are optionally taken together to form a fused, saturated, partially saturated or aromatic 5-6 membered ring having 0-3 heteroatoms selected from oxygen, phosphorus, sulfur, or nitrogen; or two geminal $R^2$s are optionally taken together to form a spiro, saturated, partially saturated or aromatic 56 membered ring having 0-3 heteroatoms selected from oxygen, phosphorus, sulfur, or nitrogen, said fused or spiro ring being optionally substituted by one or more $R^8$;

each a independently is 0-3;

each b independently is 0 or 1;

V is —C(O)—, —C(O)O—, —S(O)$_2$—, or —C(O)—N($R^1$)—;

$R^+$ is alkyl, cycloalkyl, aralkyl, aryl, heteroaryl, heteroaralkyl, or heterocyclyl, wherein said $R^+$ is optionally substituted by one or more $R^8$;

m is 0 or 1;

n is 0-5;

$R^3$ is H, —N($R^0$)$_2$, —N($R^0$)C(O)$R^0$, —CN, halogen, $CF_3$, alkyl optionally substituted by one or more groups selected from $R^7$ or —S-aryl optionally substituted by —(CH$_2$)$_{1-6}$—N($R^0$)SO$_2$($R^0$), alkenyl optionally substituted by one or more groups selected from $R^7$ or —S-aryl optionally substituted by —(CH$_2$)$_{1-6}$—N($R^0$)SO$_2$($R^0$), alkynyl optionally substituted by one or more groups selected from $R^7$ or —S-aryl optionally substituted by —(CH$_2$)$_{1-6}$—N($R^0$)SO$_2$($R^0$), cycloalkyl or carbocyclyl optionally substituted by one or more $R^8$, aryl optionally substituted by one or more $R^6$, heteroaryl optionally substituted by one or more $R^6$, or heterocyclyl optionally substituted by one or more $R^8$;

Y is alkyl, alkenyl, alkynyl, —(CR$^4$R$^5$)$_p$—, —C(O)—, —C(O)C(O)—, —C(S)—, —O—(CH$_2$)$_{0-4}$—C(O)—, —(CH$_2$)$_{0-4}$—C(O)—O—, —N($R^0$)—C(O)—, —C(O)—N($R^0$)—, —N($R^0$)—C(S)—, —S(O)$_t$—, —O—C(=N—CN)—, —O—C(=N—$R^0$)—, —C(=N—CN)—O—, —C(=N—$R^0$)—O—, —C(=N—CN)—S—, —S—C(=N—CN)—, —N($R^0$)—C(=N—CN)—, —C(=N—

CN)—, —N(R⁰)—C[=N—C(O)—R⁰], —N(R⁰)—C[=N—S(O)ₜ—R⁰], —N(R⁰)—C(=N—OR⁰)—, —N(R⁰)—C(=N—R⁰)—, or —C(=N—R⁰)—;

each R⁴ is independently H, alkyl optionally substituted by R⁷, alkenyl optionally substituted by R⁷, or alkynyl optionally substituted by R⁷;

each R⁵ is independently selected from H, —C(O)—OR⁶, —C(O)—N(R⁰)₂, —S(O)₂—N(R⁰)₂, —S(O)₂—R⁰, aryl optionally substituted by R⁶, or heteroaryl optionally substituted by R⁶;

p is 1-5;

t is 1 or 2;

each R⁶ is independently selected from halogen, —CF₃, —OCF₃, —OR⁰, —(CH₂)₁₋₆—OR⁰, —SR⁰, —(CH₂)₁₋₆—SR⁰, —SCF₃, —R⁰, methylenedioxy, ethylenedioxy, —NO₂, —CN, —(CH₂)₁₋₆—CN, —N(R⁰)₂, —(CH₂)₁₋₆—N(R⁰)₂, —NR⁰C(O)R⁰, —NR⁰(CN), —NR⁰C(O)N(R⁰)₂, —NR⁰C(S)N(R⁰)₂, —NR⁰CO₂R⁰, —NR⁰NR⁰C(O)R⁰, —NR⁰NR⁰C(O)N(R⁰)₂, —NR⁰NR⁰CO₂R⁰, —C(O)C(O)R⁰, —C(O)CH₂C(O)R⁰, —(CH₂)₀₋₆CO₂R⁰, —O—C(O)R⁰, —C(O)R⁰, —C(O)N(R⁰)N(R⁰)₂, —C(O)N(R⁰)₂, —C(O)N(R⁰)OH, —C(O)N(R⁰)SO₂R⁰, —OC(O)N(R⁰)₂, —S(O)ₜR⁰, —S(O)ₜ—OR⁰, —S(O)ₜN(R⁰)C(O)R⁰, —S(O)ₜN(R⁰)OR⁰, —NR⁰SO₂N(R⁰)₂, —NR⁰SO₂R⁰, —C(=S)N(R⁰)₂, —C(=NH)—N(R⁰)₂, —(CH₂)₁₋₆—C(O)R⁰, —C(=N—OR⁰)—N(R⁰)₂, —O—(CH₂)₀₋₆—SO₂N(R⁰)₂, —(CH₂)₁₋₆—NHC(O)R⁰, or —SO₂N(R⁰)₂ wherein the two R⁰s on the same nitrogen are optionally taken together to form a 5-8 membered saturated, partially saturated, or aromatic ring having additional 0-4 heteroatoms selected from oxygen, phosphorus, nitrogen, or sulfur;

each R⁷ is independently selected from halogen, —CF₃, —R⁰, —OR⁰, —OCF₃, —(CH₂)₁₋₆—OR⁰, —SR⁰, —SCF₃, —(CH₂)₁₋₆—SR⁰, aryl optionally substituted by R⁶, methylenedioxy, ethylenedioxy, —NO₂, —CN, —(CH₂)₁₋₆—CN, —N(R⁰)₂, —(CH₂)₁₋₆—N(R⁰)₂, —NR⁰C(O)R⁰, —NR⁰(CN), —NR⁰C(O)N(R⁰)₂, —N(R⁰)C(S)N(R⁰)₂, —NR⁰CO₂R⁰, —NR⁰NR⁰C(O)R⁰, —NR⁰NR⁰C(O)N(R⁰)₂, —NR⁰NR⁰CO₂R⁰, —C(O)C(O)R⁰, —C(O)CH₂C(O)R⁰, —(CH₂)₀₋₆—CO₂R⁰, —C(O)R⁰, —C(O)N(R⁰)N(R⁰)₂, —C(O)N(R⁰)₂, —C(O)N(R⁰)OH, —OC(O)R⁰, —C(O)N(R⁰)SO₂R⁰, —OC(O)N(R⁰)₂, —S(O)ₜR⁰, —S(O)ₜ—OR⁰, —S(O)ₜN(R⁰)C(O)R⁰, —S(O)ₜN(R⁰)OR⁰, —NR⁰SO₂N(R⁰)₂, —NR⁰SO₂R⁰, —C(=S)N(R⁰)₂, —C(=NH)—N(R⁰)₂, —(CH₂)₁₋₆—C(O)R⁰, —C(=N—OR⁰)—N(R⁰)₂, —O—(CH₂)₀₋₆—SO₂N(R⁰)₂, —(CH₂)₁₋₆—NHC(O)R⁰, or —SO₂N(R⁰)₂ wherein the two R⁰s on the same nitrogen are optionally taken together to form a 5-8 membered saturated, partially saturated, or aromatic ring having additional 0-4 heteroatoms selected from oxygen, phosphorus, nitrogen, or sulfur;

each R⁸ is independently selected from R⁷, =O, =S, =N(R⁰), =N(CN);

R⁹ is H or oxo;

each R⁰ is independently selected from hydrogen, alkyl, alkenyl, alkynyl, cycloalkyl, carbocyclylalkyl, aryl, heteroaryl, aralkyl, heteroaralkyl, heterocyclyl, or heterocyclylalkyl, wherein each member of R⁰ except H is optionally substituted by one or more R*, OR*, N(R*)₂, =O, =S, halo, CF₃, NO₂, CN, —C(O)R*, —CO₂R*, —C(O)-aryl, —C(O)-heteroaryl, —C(O)-aralkyl, —S(O)ₜ-aryl, —S(O)ₜ-heteroaryl, —NR*SO₂R*, —NR*C(O)R*, —NR*C(O)N(R*)₂, —N(R*)C(S)N(R*)₂, —NR*CO₂R*, —NR*NR*C(O)R*, —NR*NR*C(O)N(R*)₂, —NR*NR*CO₂R*, —C(O)C(O)R*, —C(O)CH₂C(O)R*, —C(O)N(R*)N(R*)₂, —C(O)N(R*)₂, —C(O)NR*SO₂R*, —OC(O)N(R*)₂, —S(O)ₜR*, —NR*SO₂N(R*)₂, —SO₂N(R*)₂ wherein the two R*s on the same nitrogen are optionally taken together to form a 5-8 membered saturated, partially saturated or aromatic ring having additional 0-4 heteroatoms selected from oxygen, phosphorus, nitrogen or sulfur; and each R* is independently H, alkyl, alkenyl, alkynyl, cycloalkyl, aryl, or heteroaryl.

In one embodiment of the present invention the B ring is pyrrolidine.

In one embodiment R⁹ is H, while in another embodiment R⁹ is oxo.

In one embodiment R¹ is optionally substitued aryl. For example, R¹ is phenyl mono- or di- substituted with halogen. Suitably R¹ may be phenyl di-substituted with Cl.

In one embodiment —(Y)ₘ—R³ suitably is

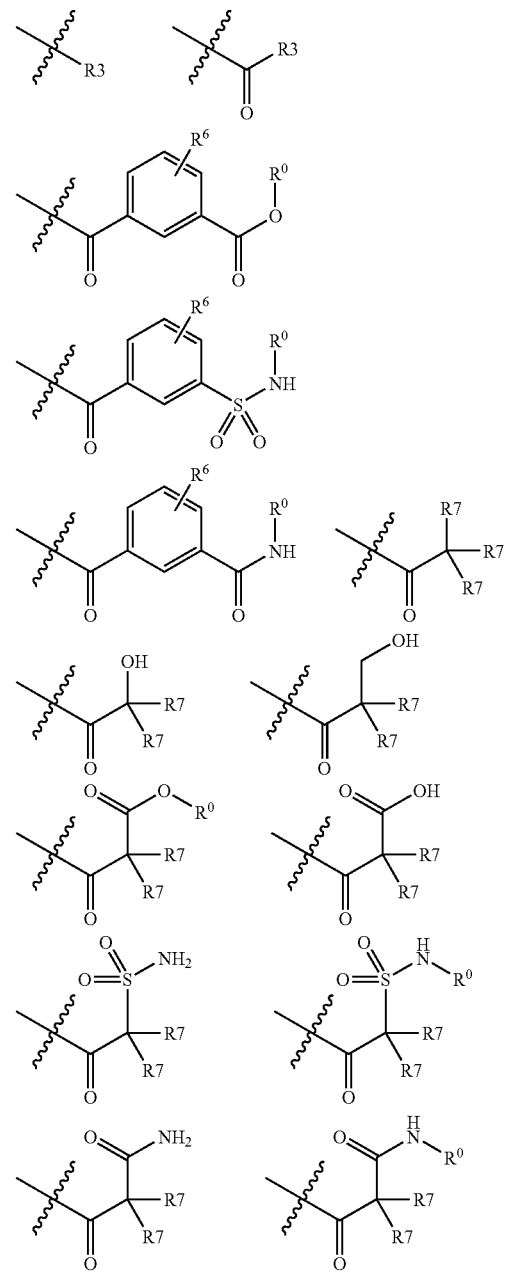

-continued
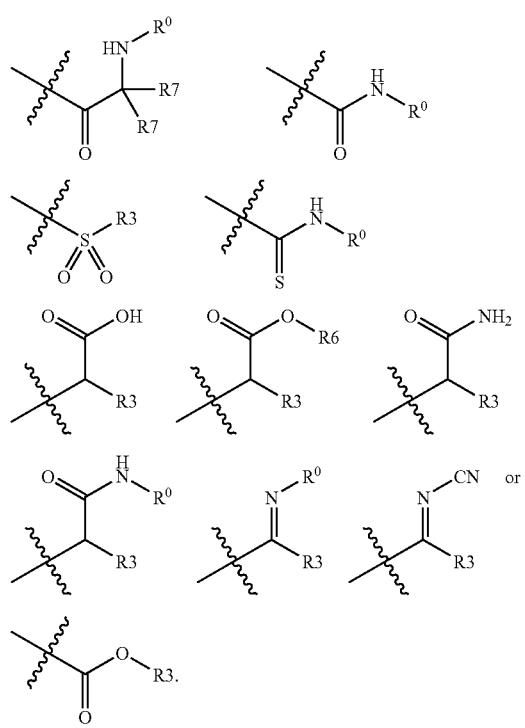
More suitably —(Y)$_m$—R$^3$ is
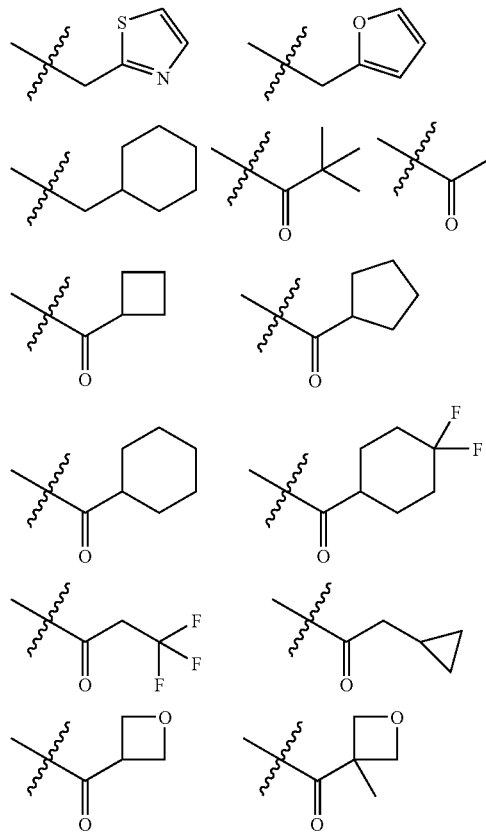
-continued
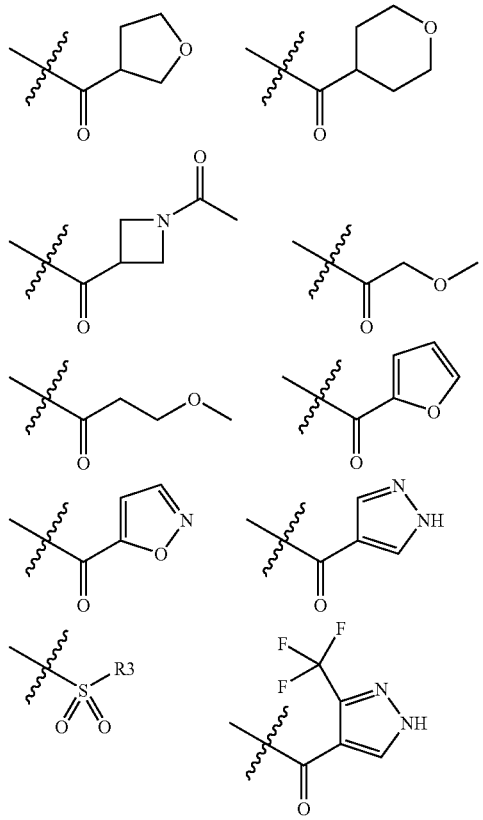
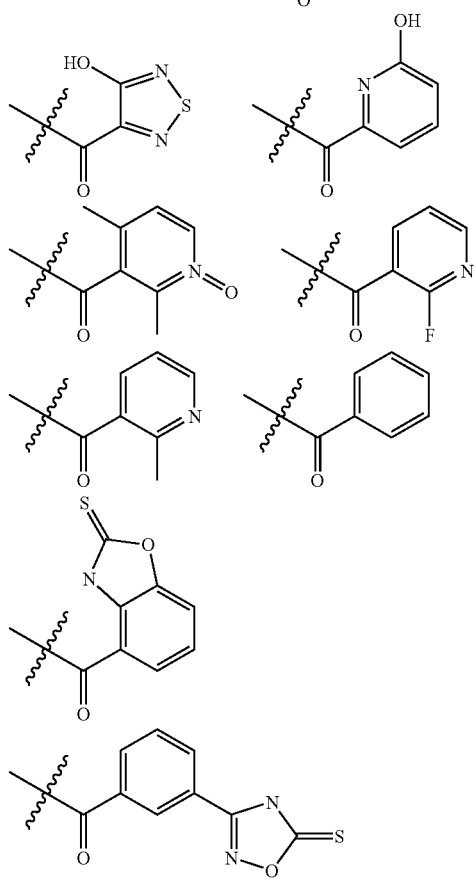

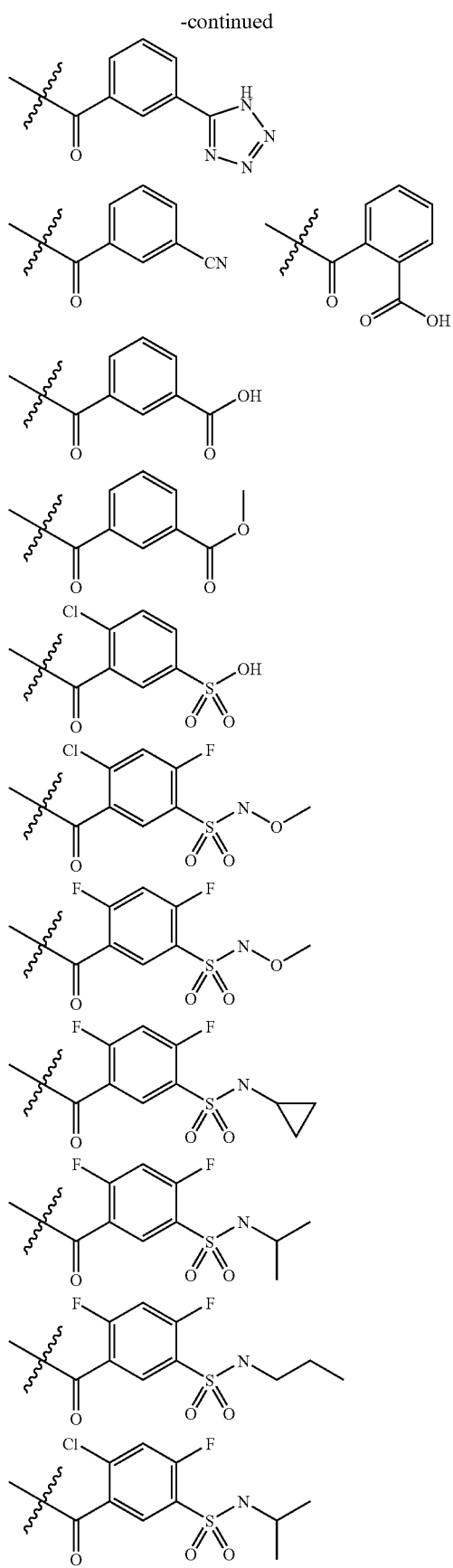
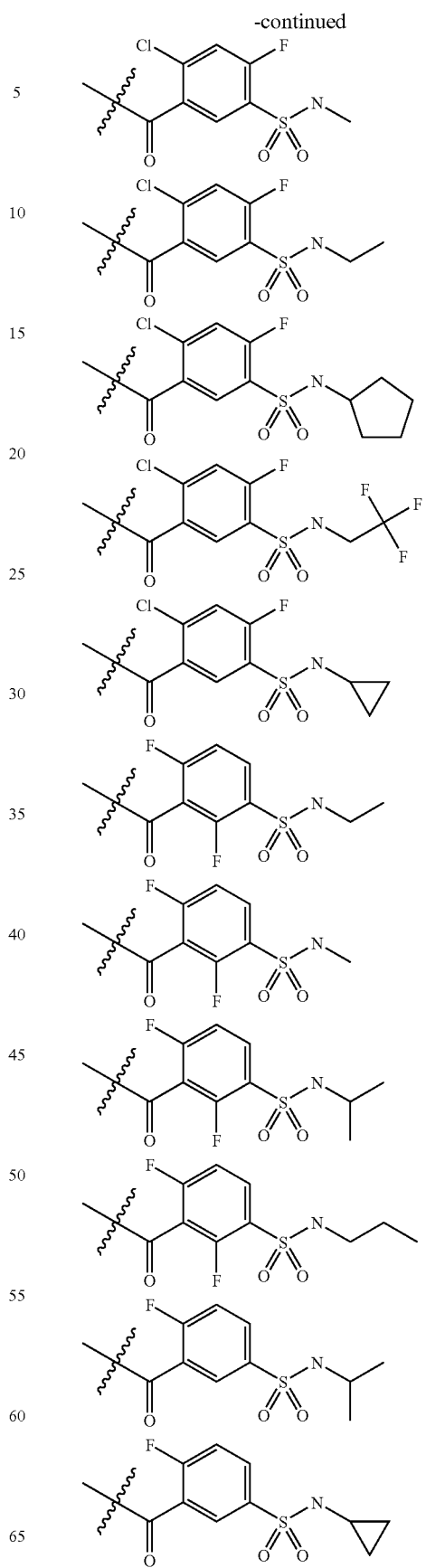

-continued
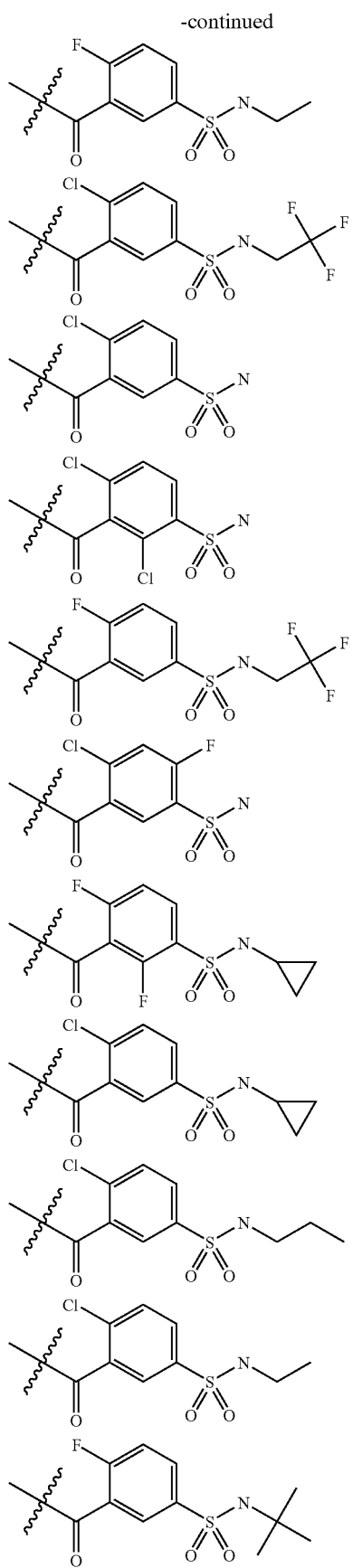
-continued
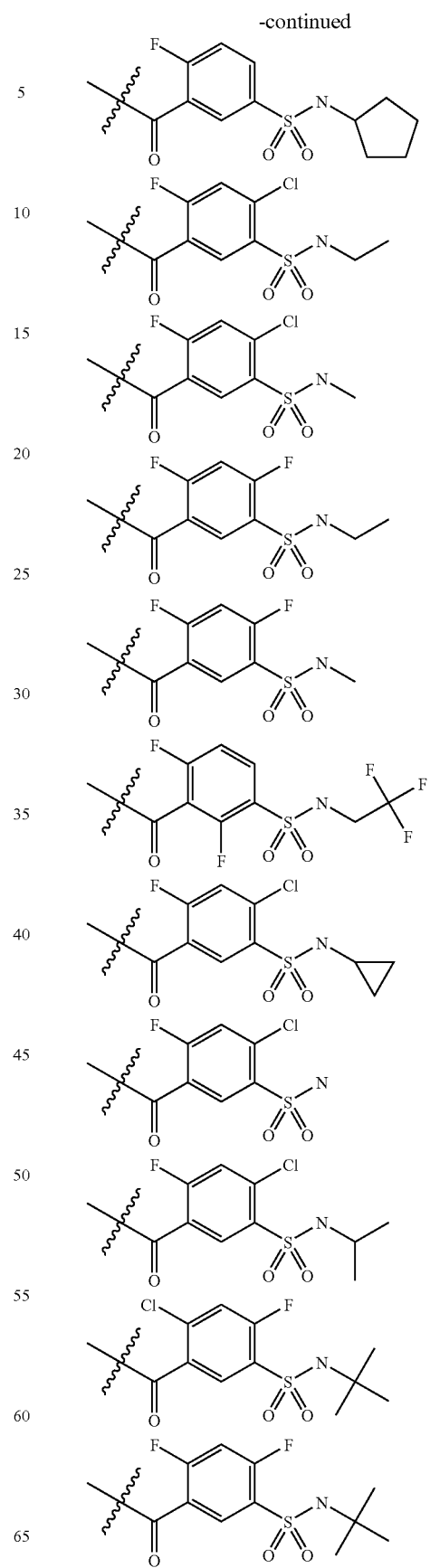

-continued
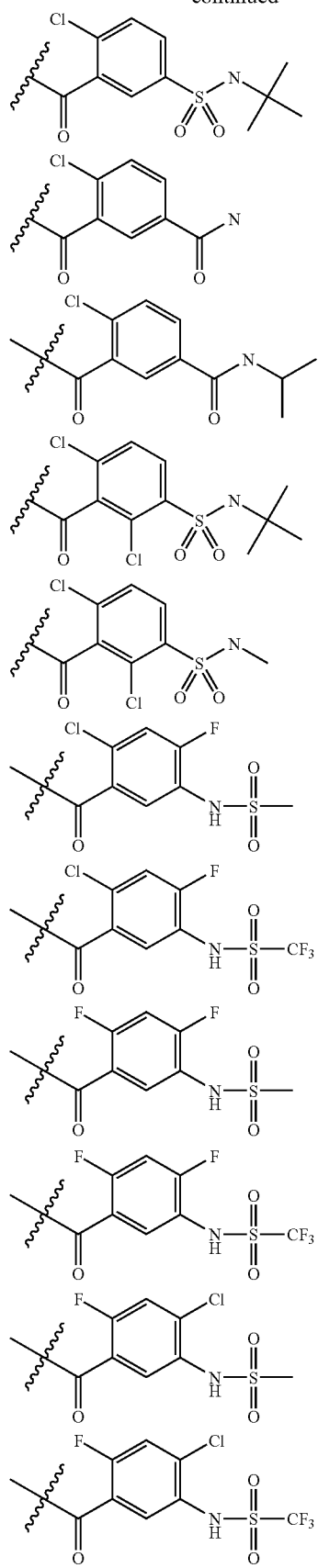
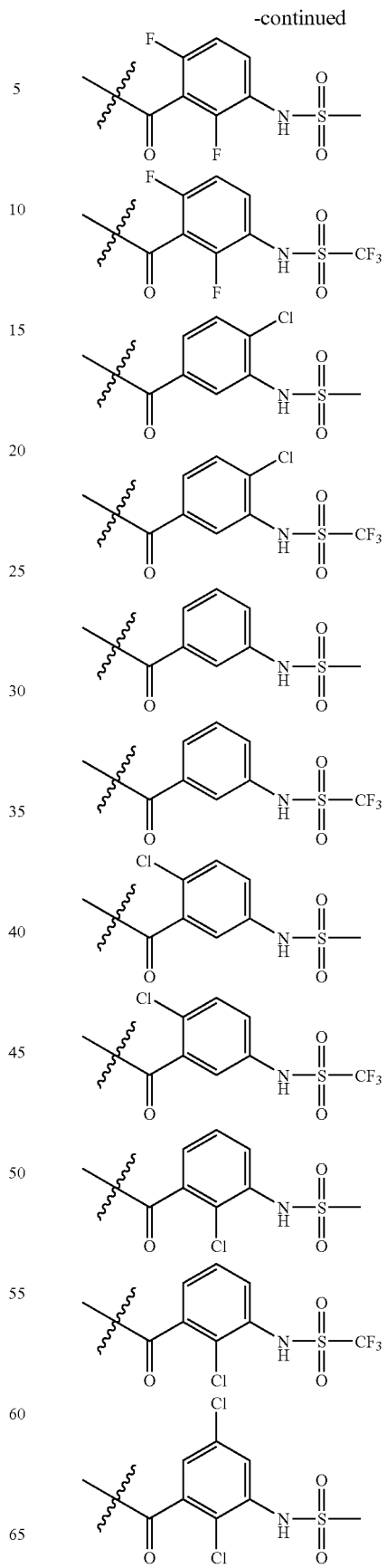

-continued
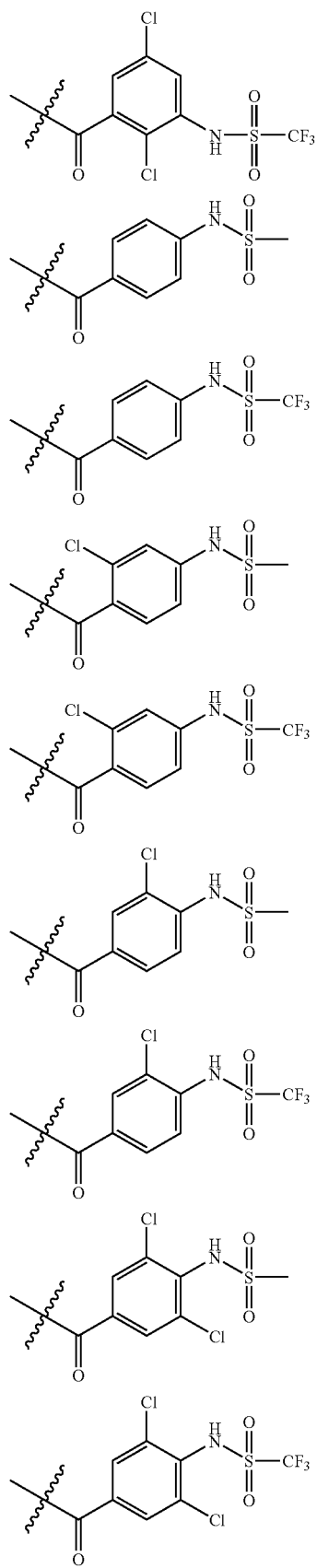
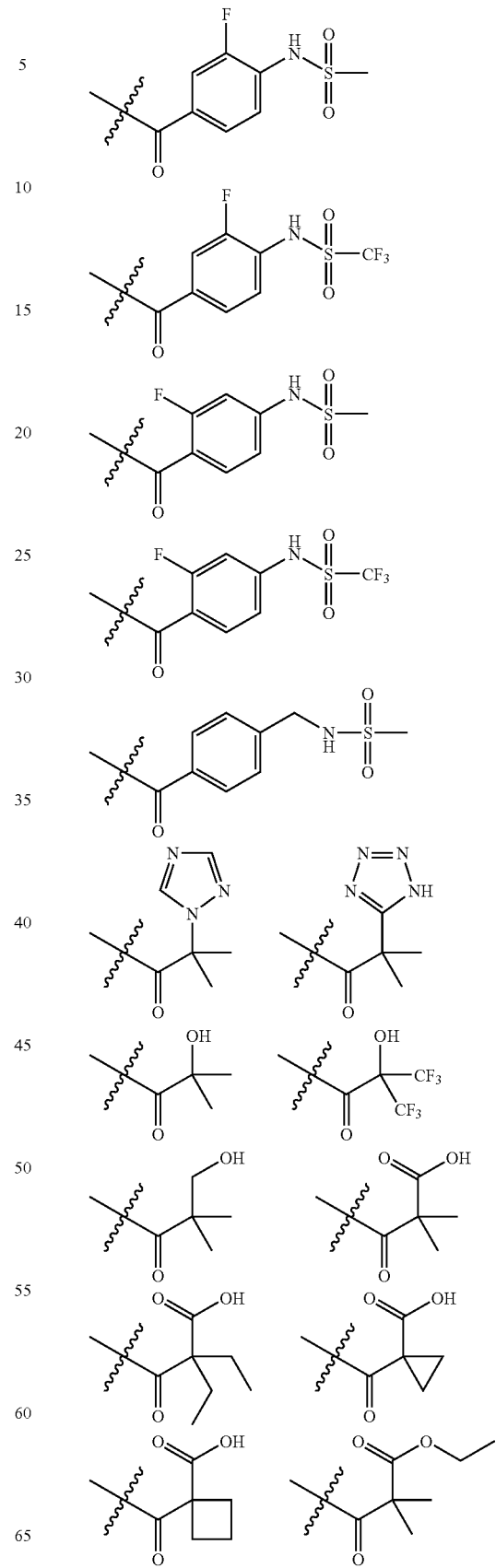

-continued
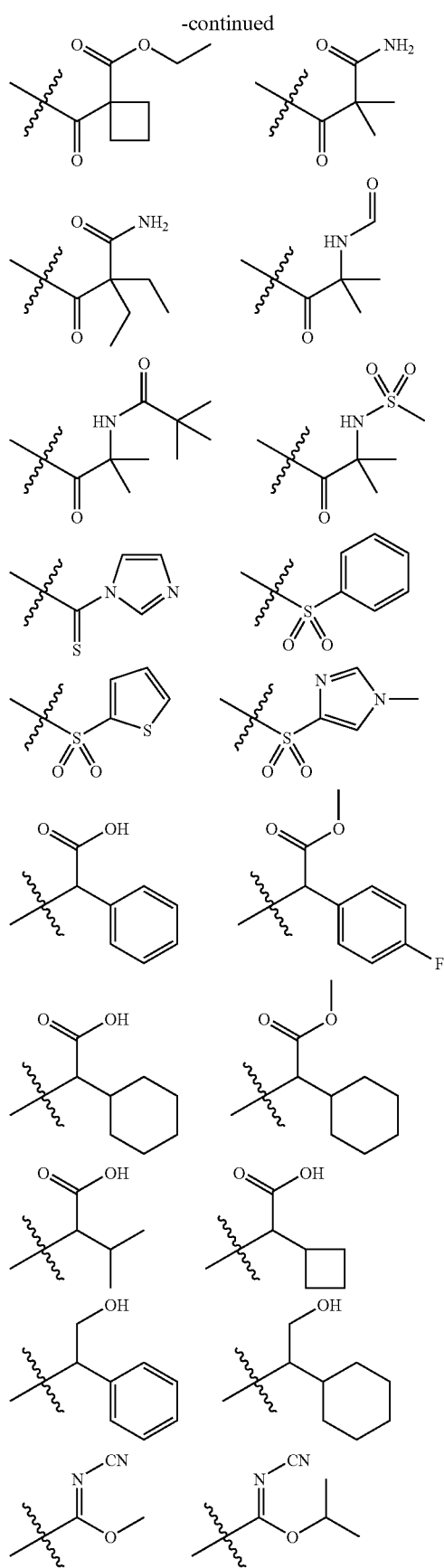
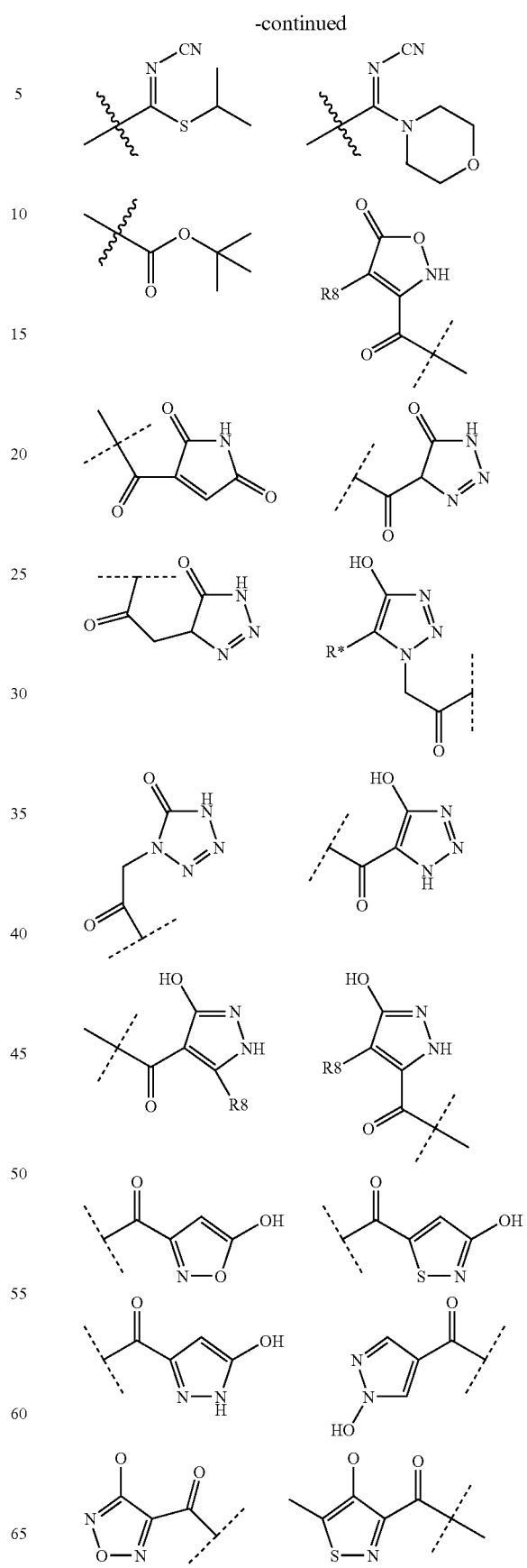

-continued

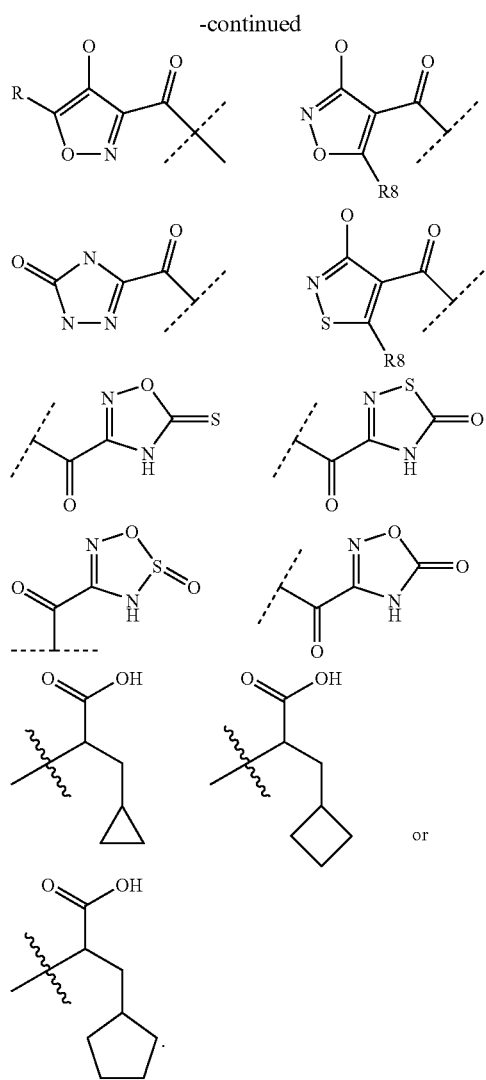

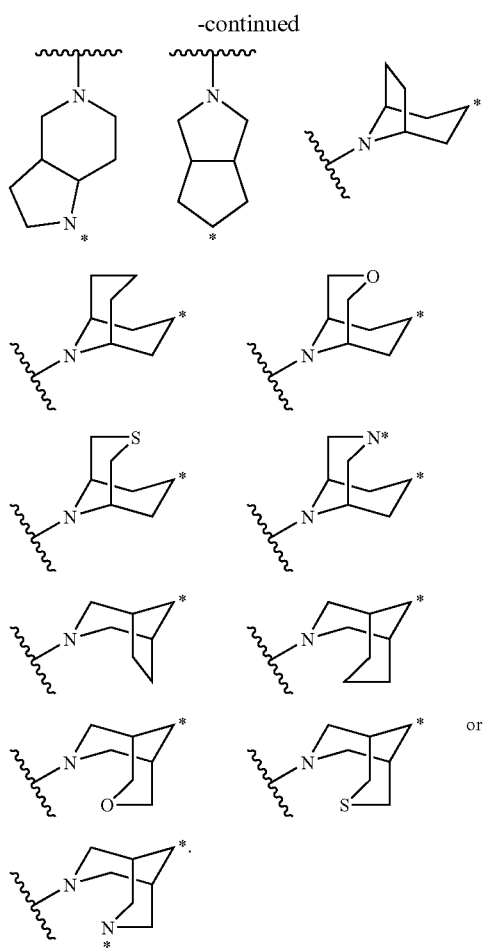

In one embodiment X is —(CH$_2$)—, —(CH$_2$—CH$_2$)—, or —(CH$_2$—CH$_2$—CH$_2$)—. Suitably X is optionally one or more halogen or oxo. Further X optionally has 1-3 heteroatoms selected from oxygen, phosphorus, sulfur, or nitrogen.

In one embodiment the A ring is selected from the following, where the asterisk (*) indicates the preferred, but not limiting, point(s) of substitution:

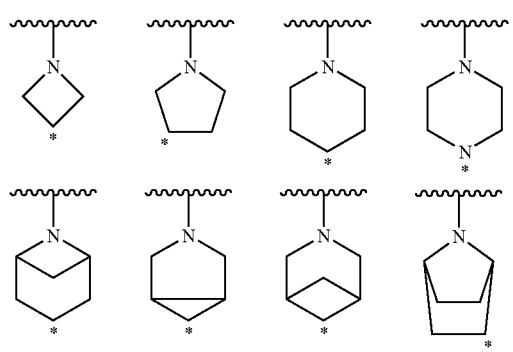

Suitably each R$^2$, with the asterisk (*) indicating a preferred, but not limiting, point of substitution from Ring A, independently is selected from

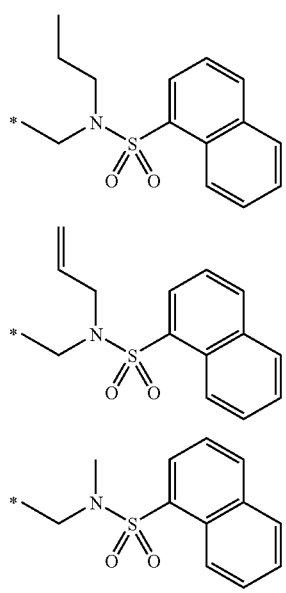

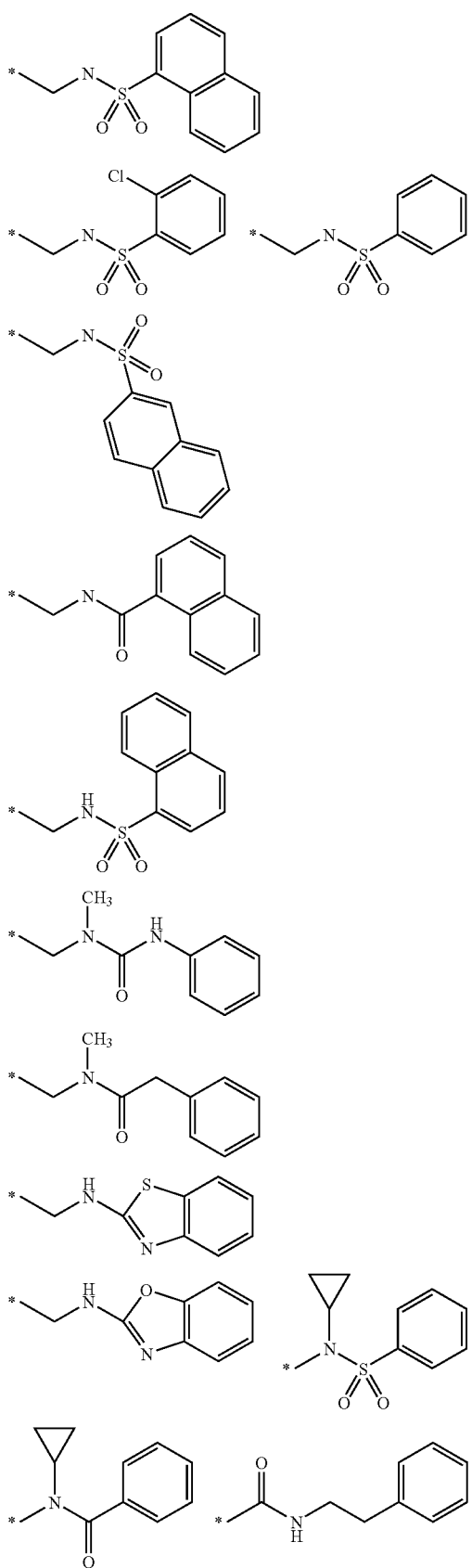
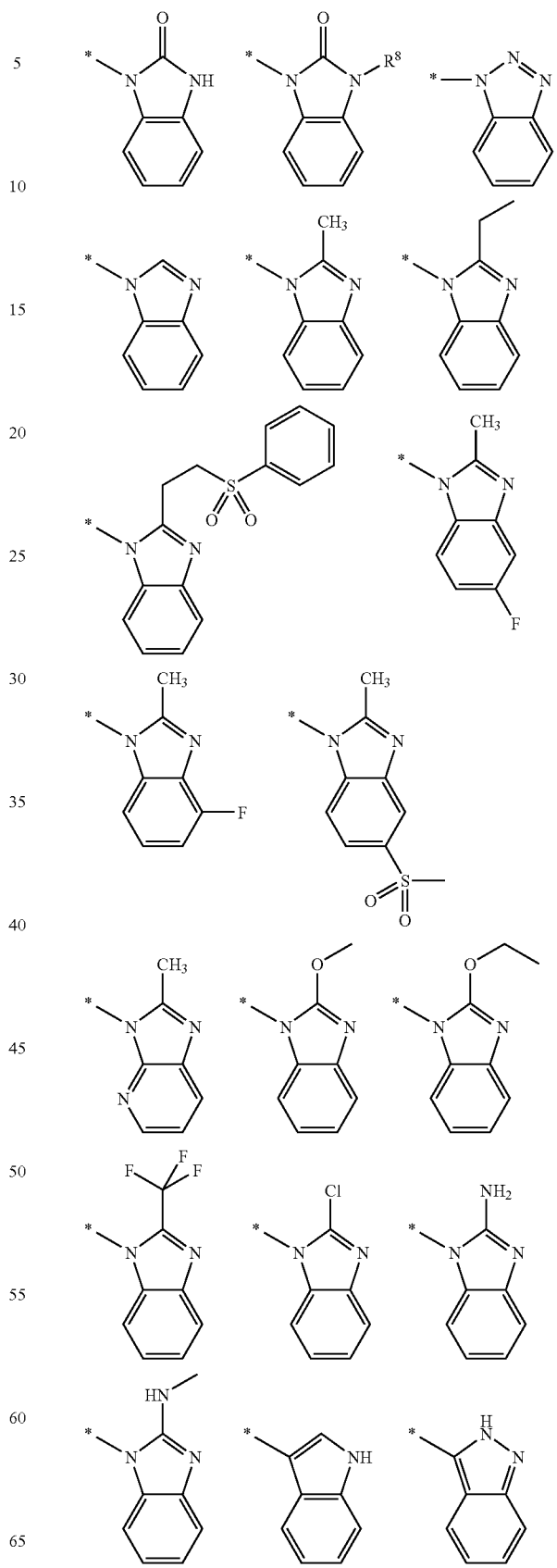

-continued
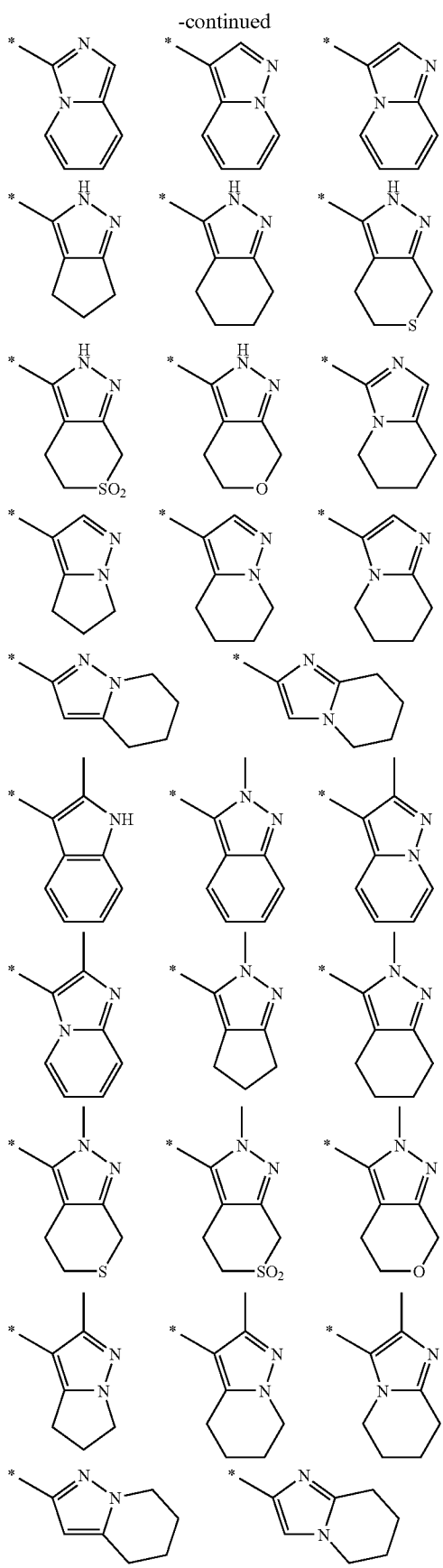
-continued
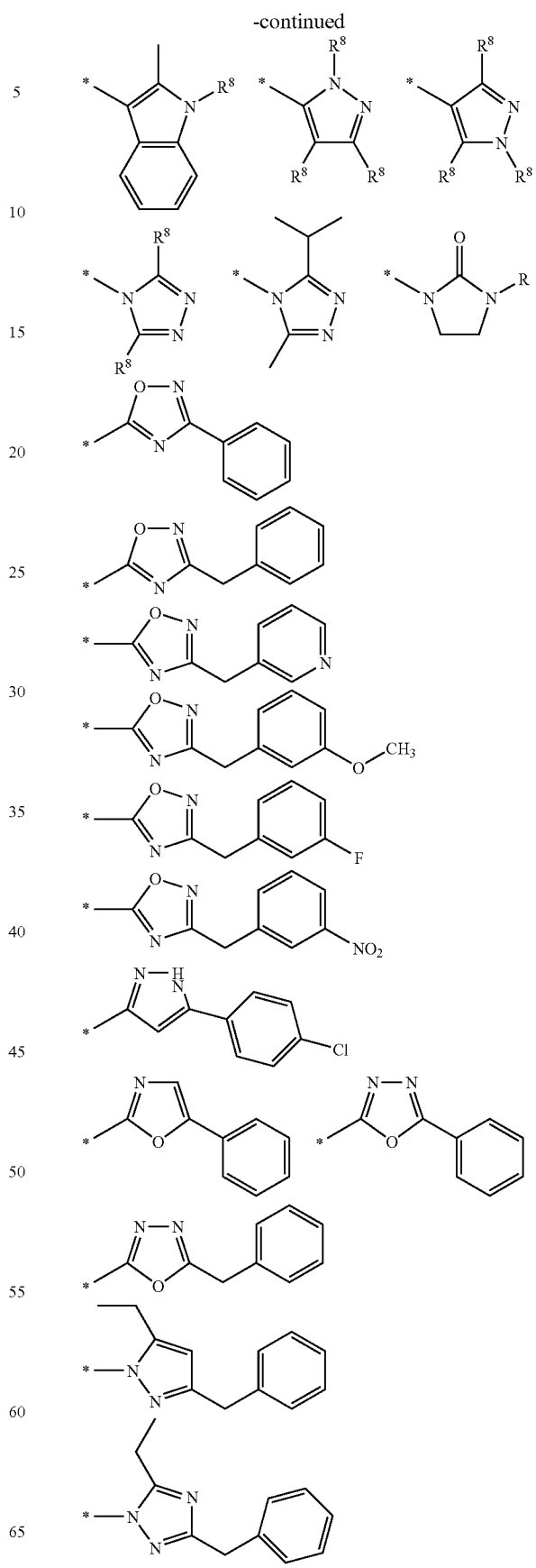

-continued
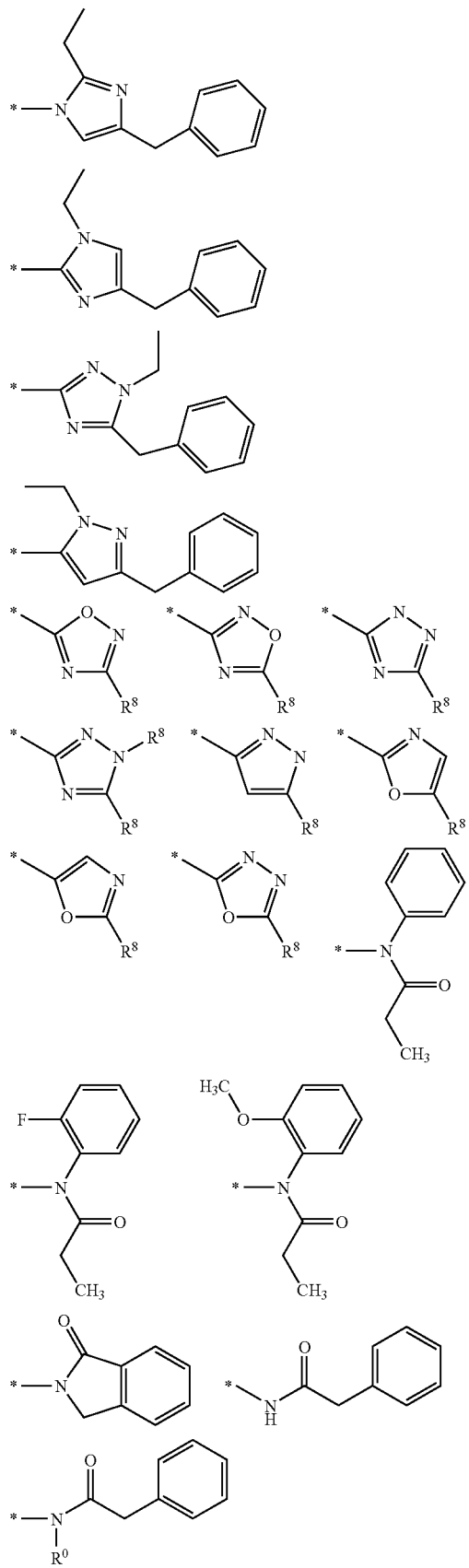
-continued
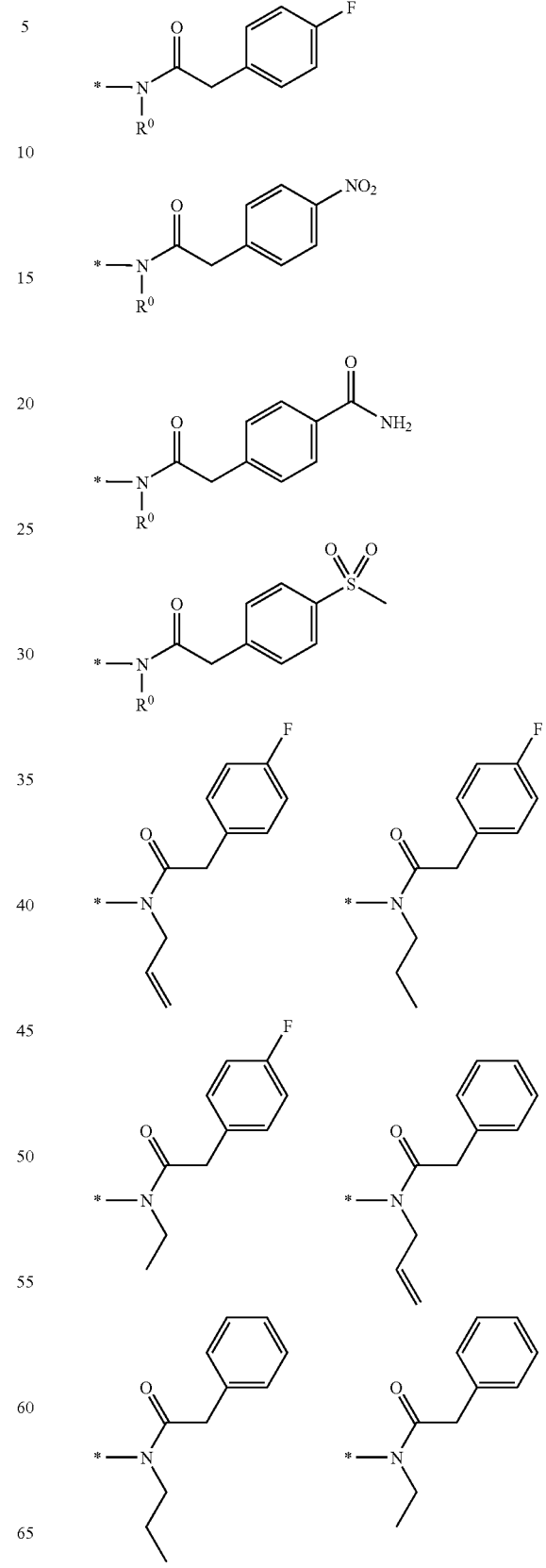

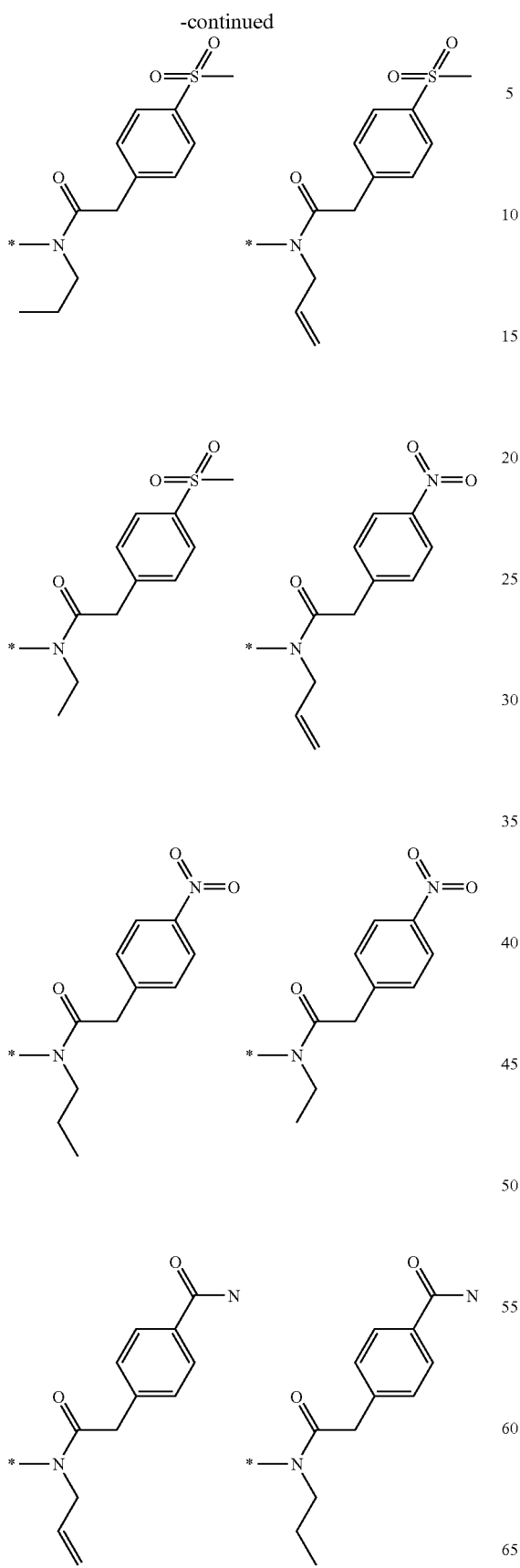
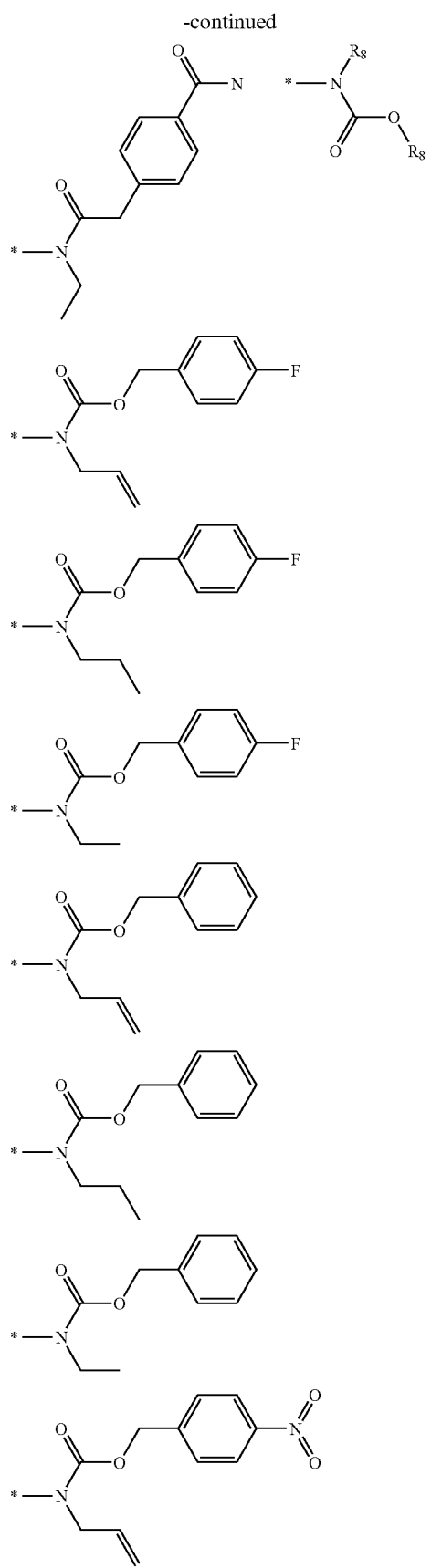

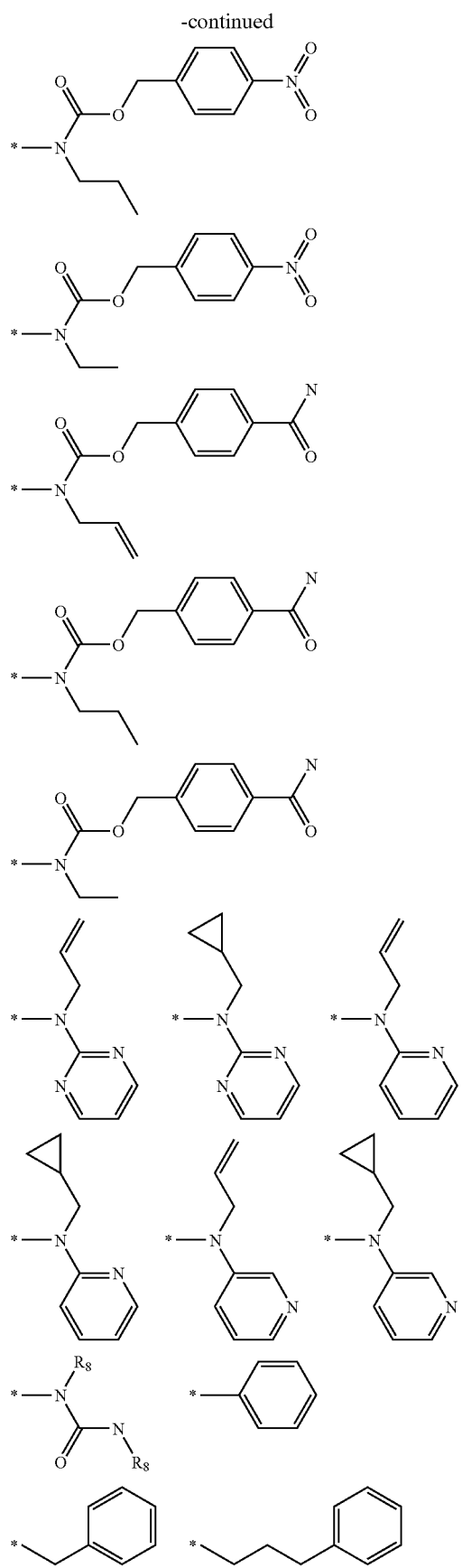
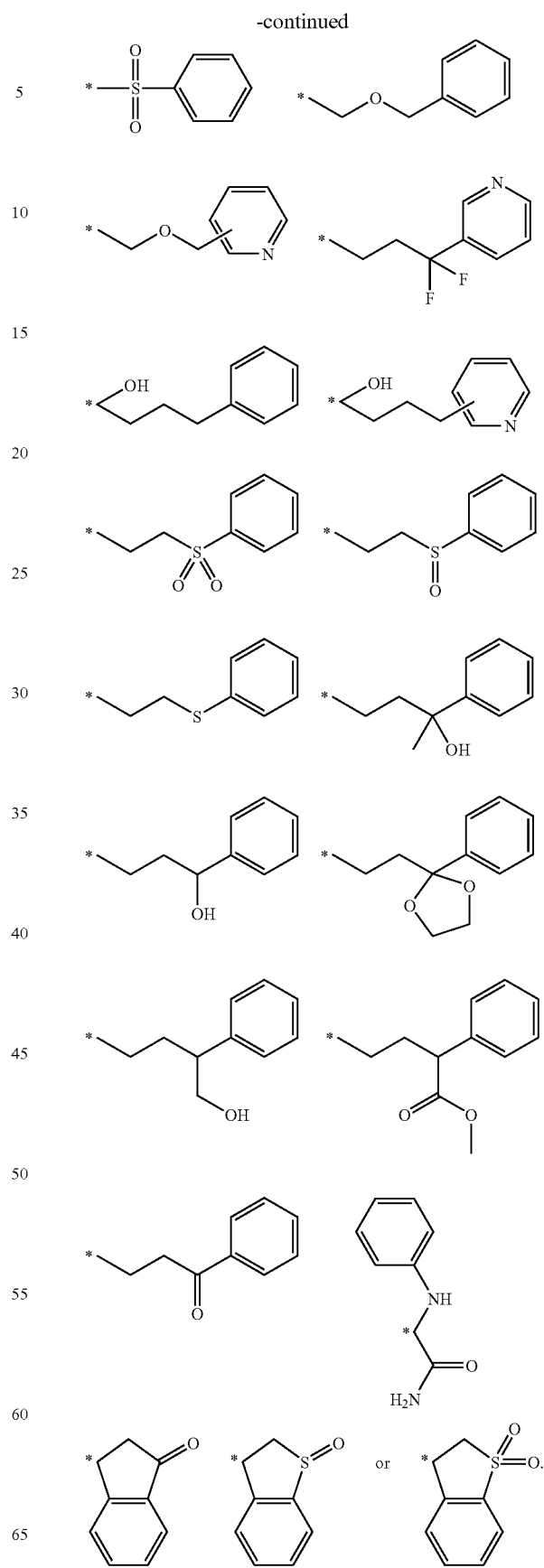

In one embodiment the ring A, with two geminal $R^2$s, is selected from:
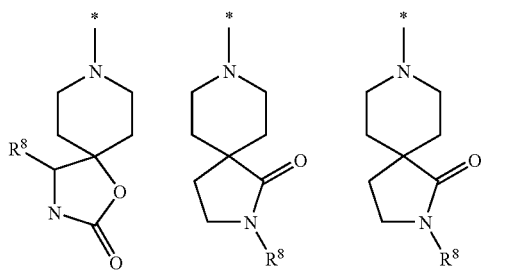
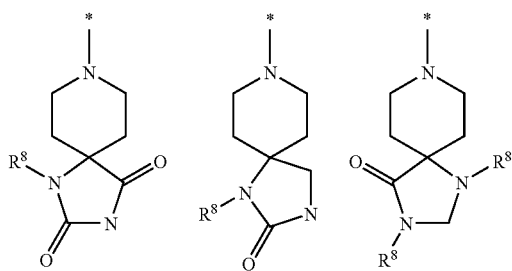
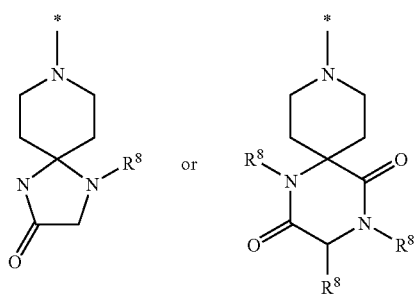
Suitably the A ring is tropane or piperidine, either optionally substituted with one or more $R^2$. Preferrably, A—$R^2$ is comprised of one of the following:
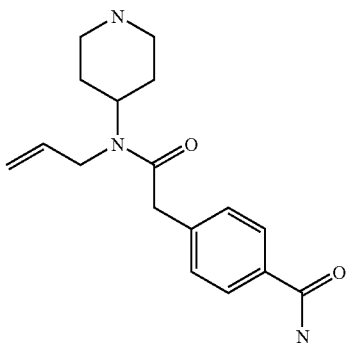
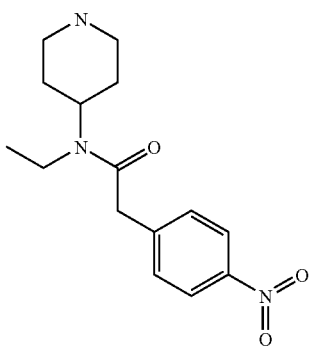
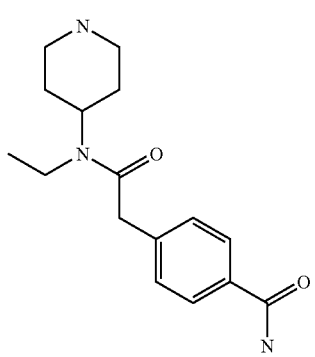
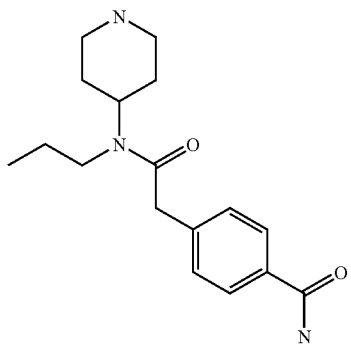
-continued
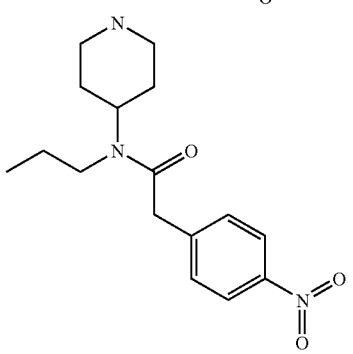
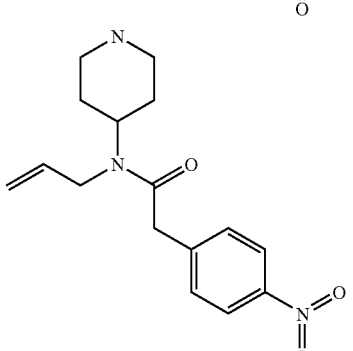
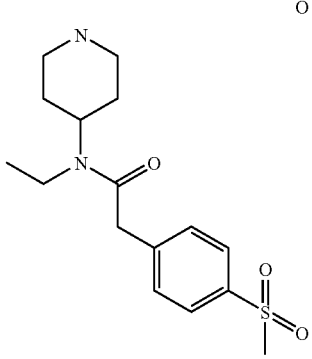

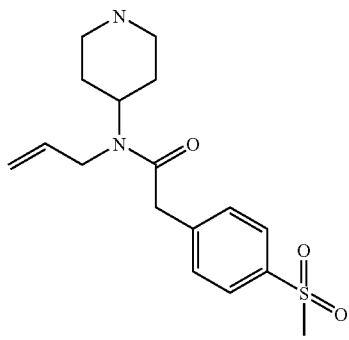
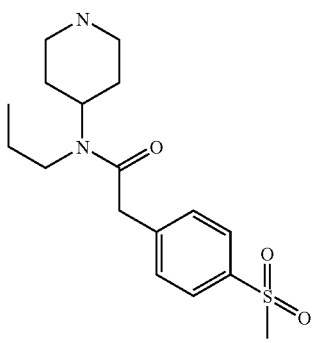
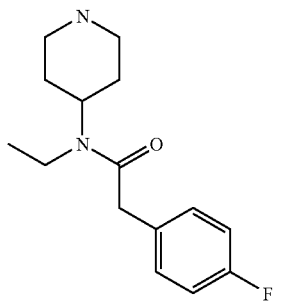
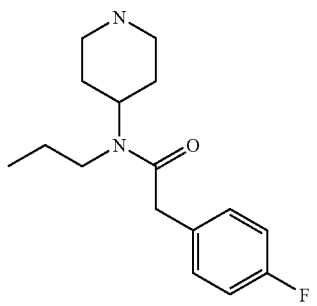
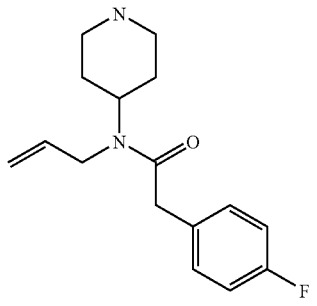
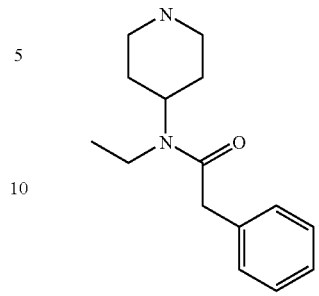
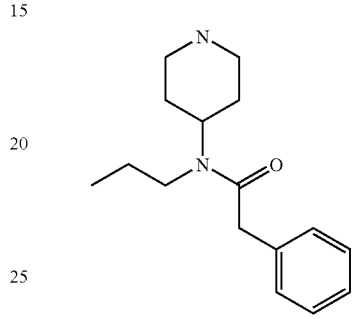
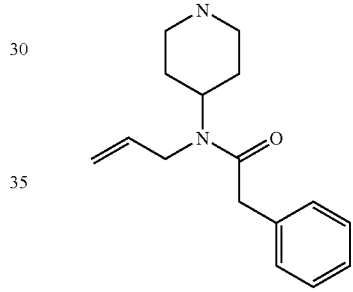
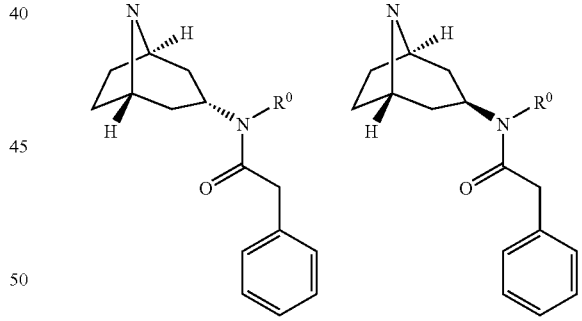
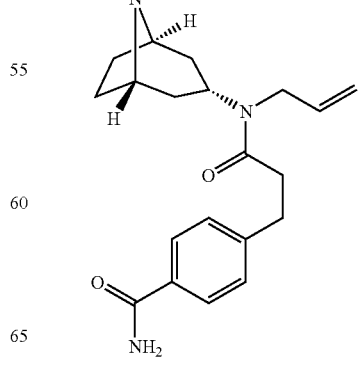

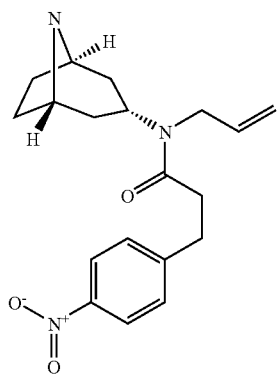
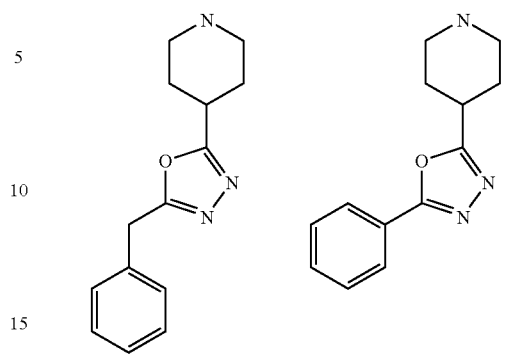
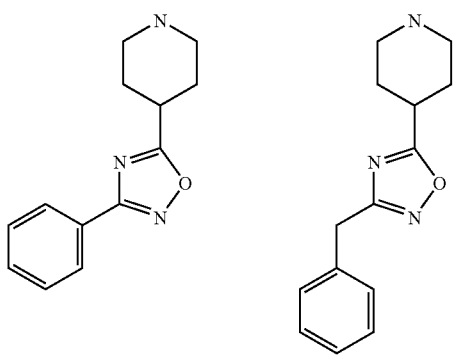
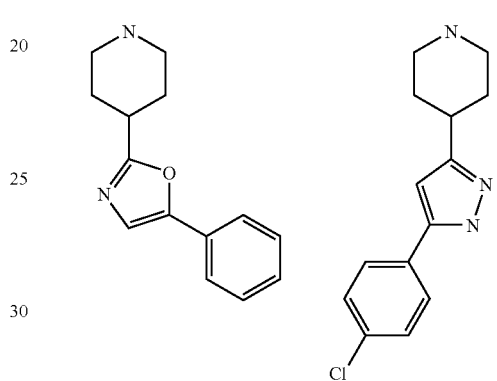
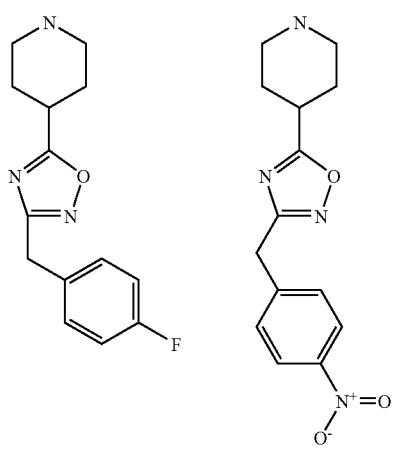
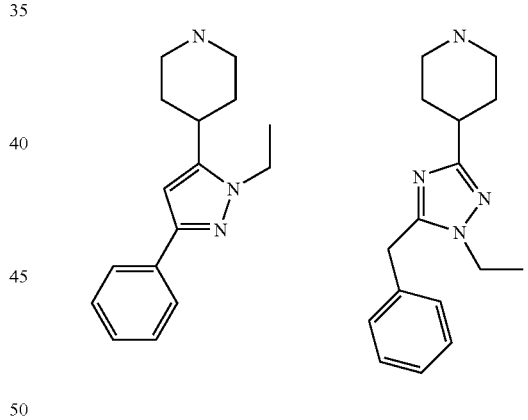
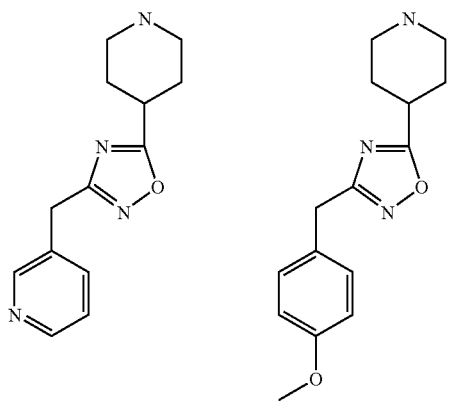
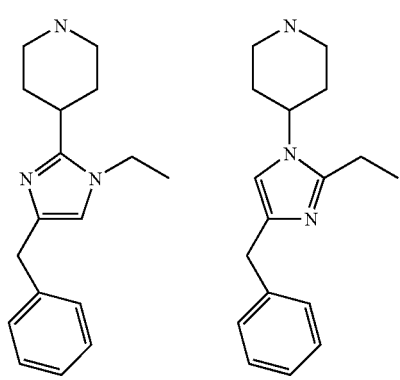

-continued
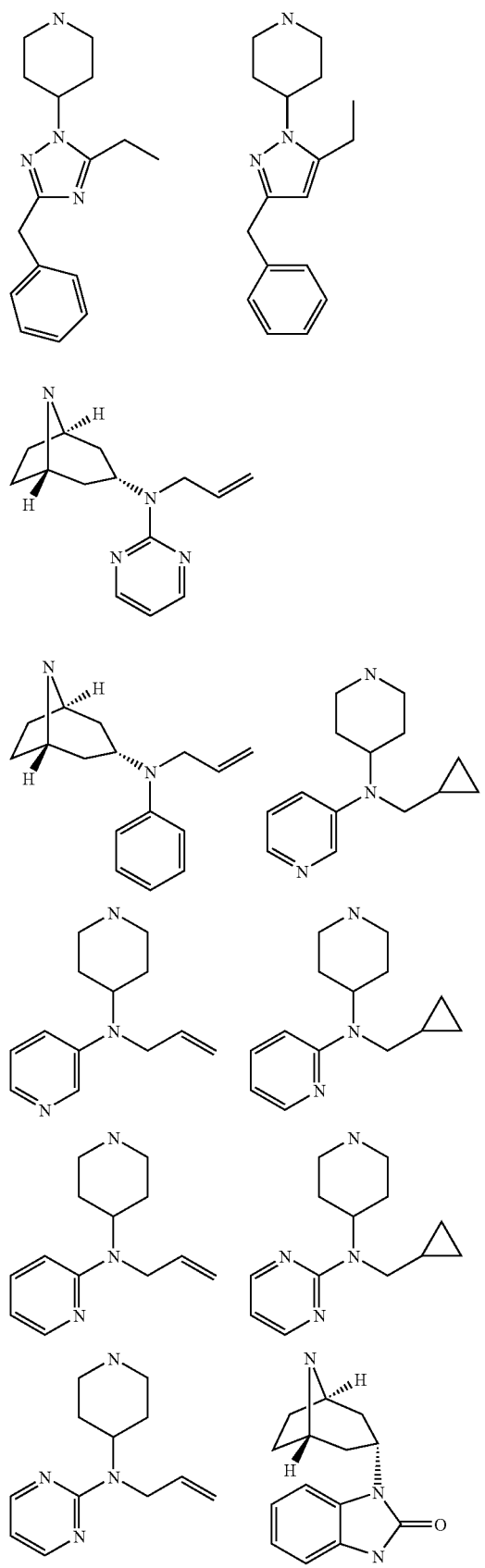
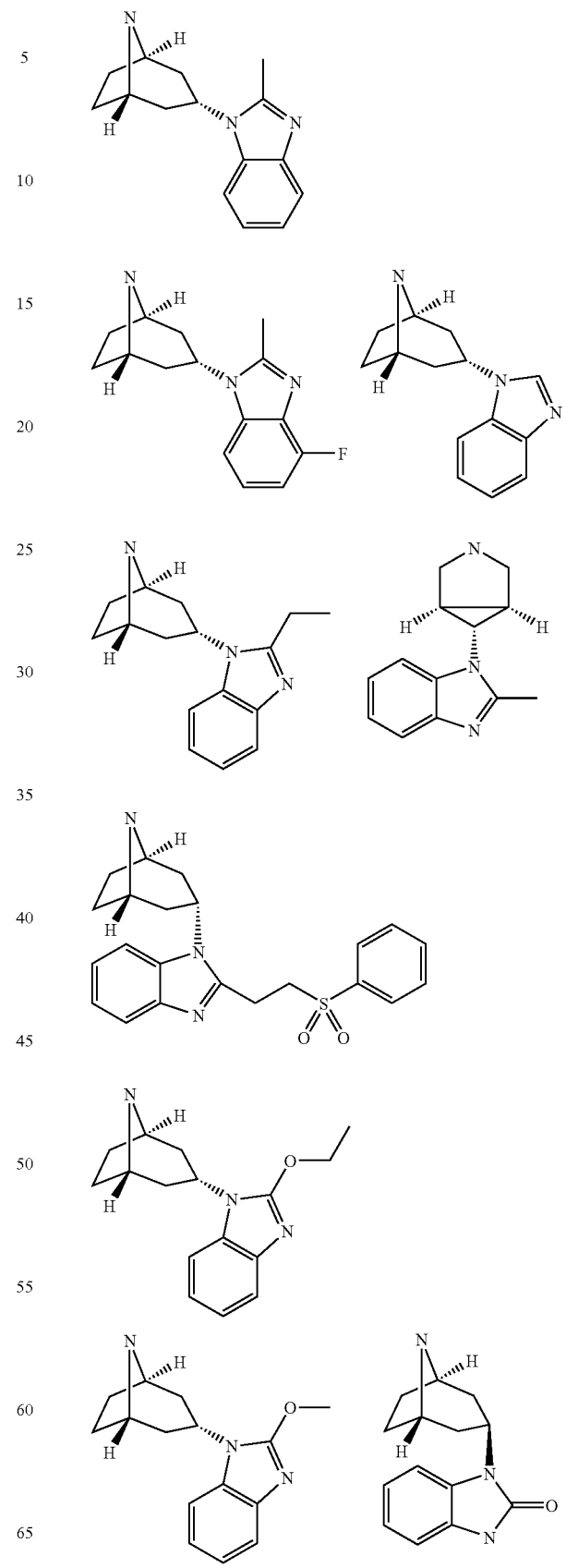

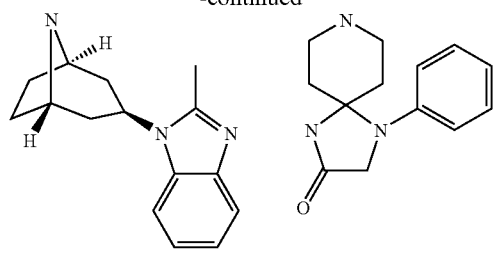
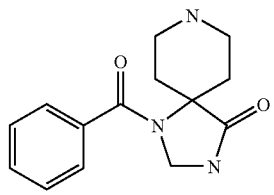
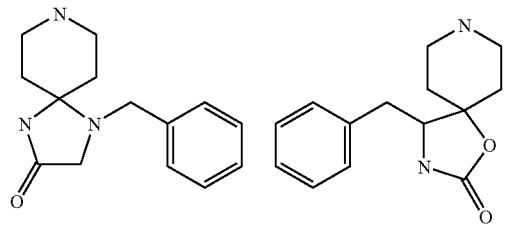
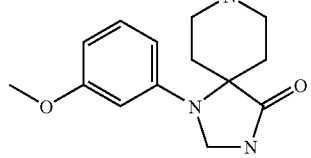
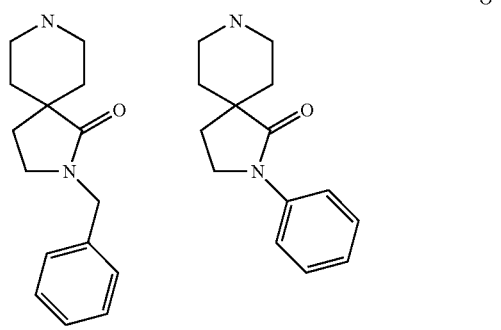
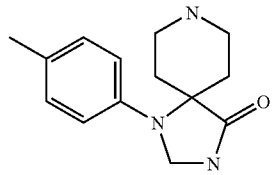
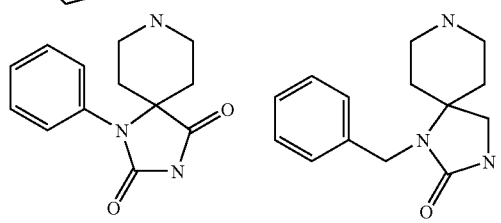
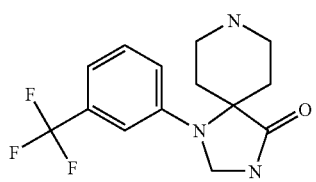
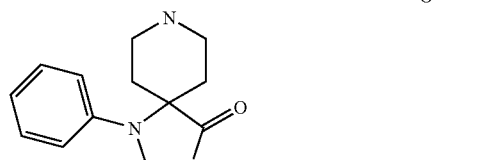
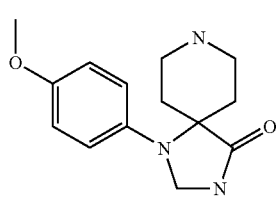
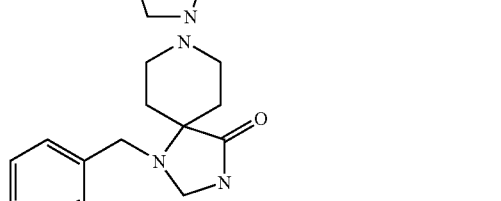
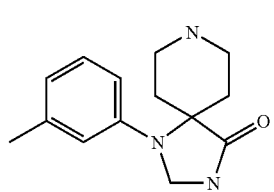
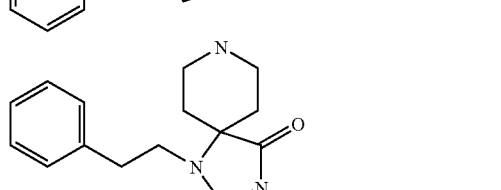
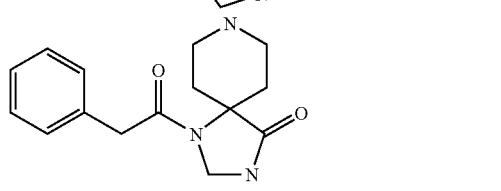

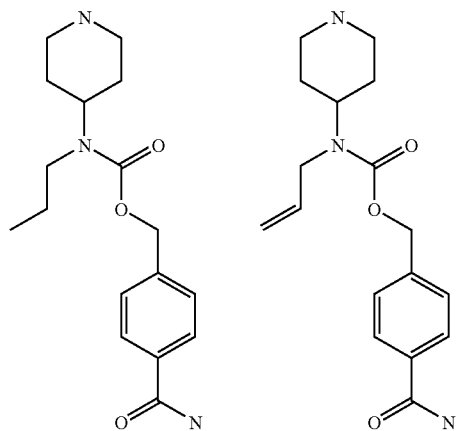
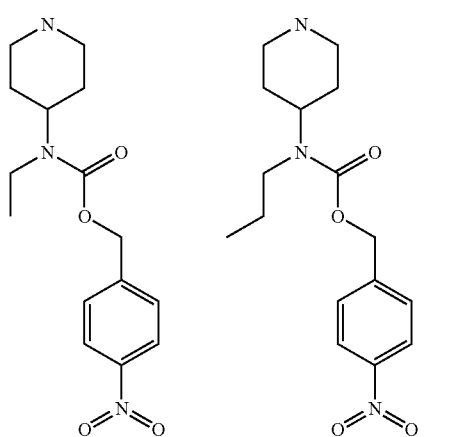
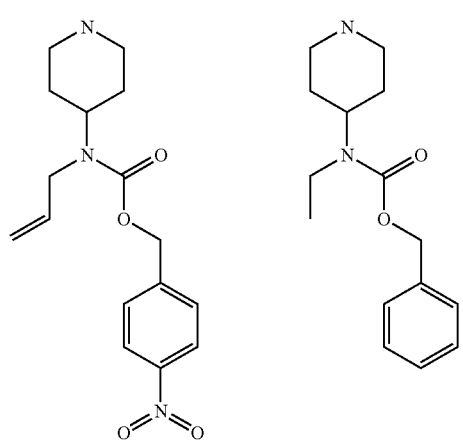
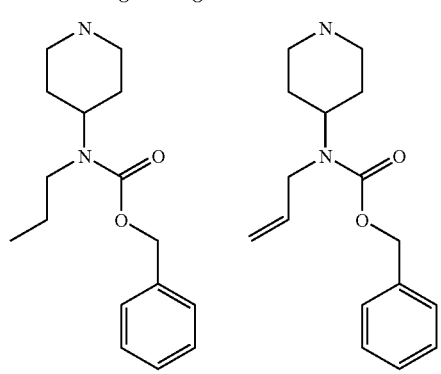
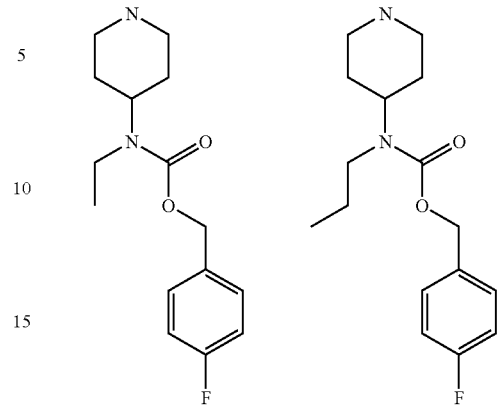
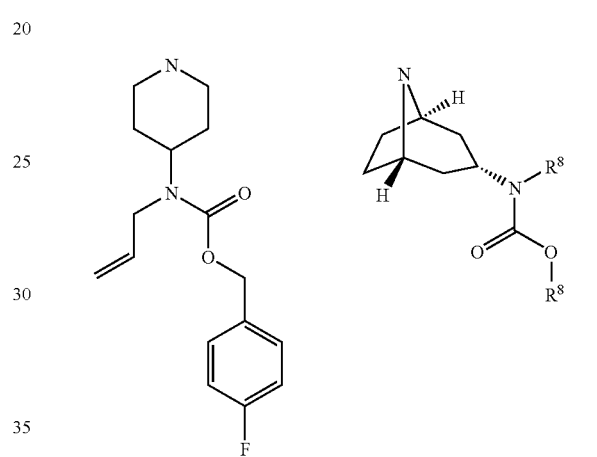
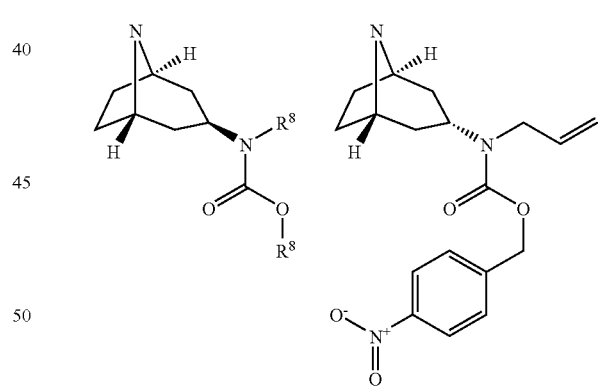
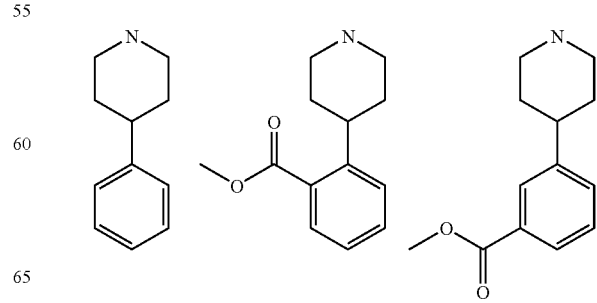

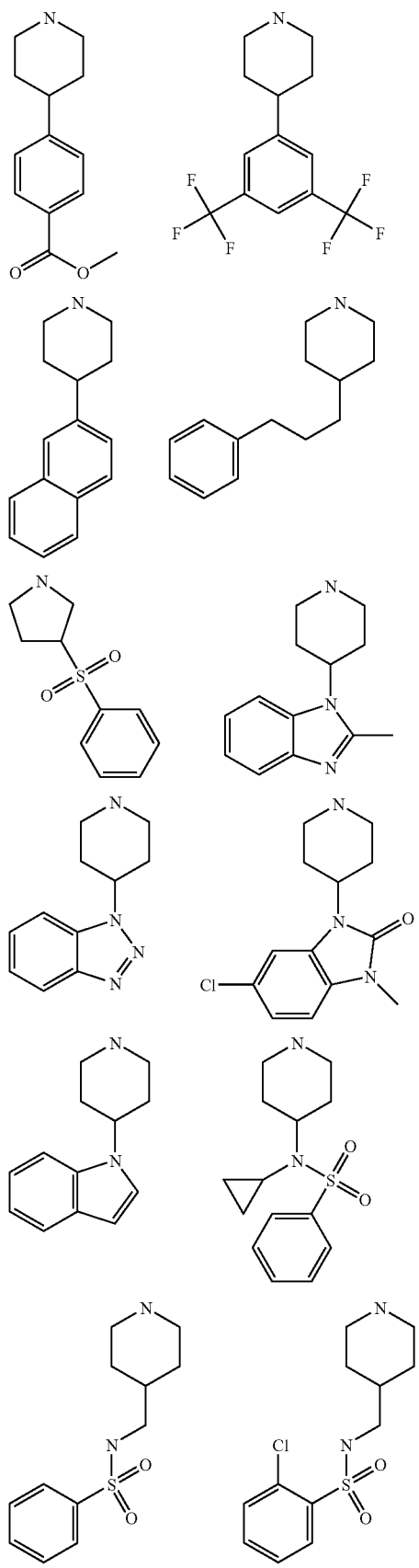
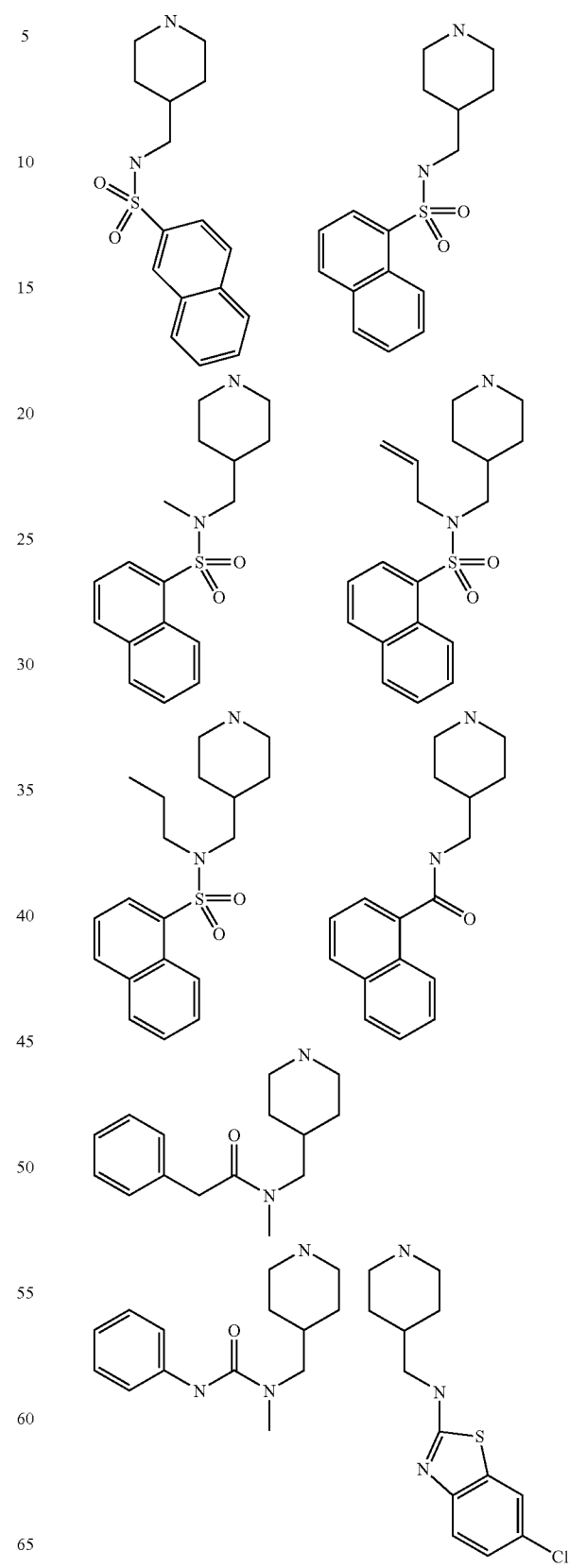

-continued

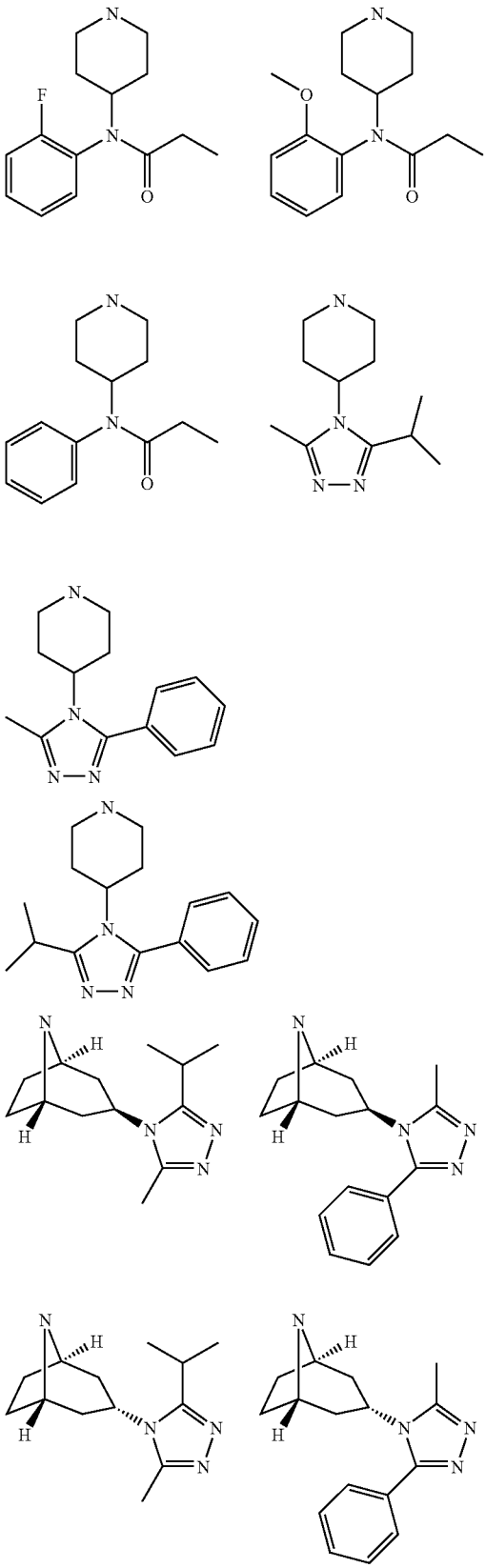

In one embodiment the A ring contains at least one additional nitrogen atom and said A ring optionally is N-substituted. Suitably the A ring is N-substituted with —(CH$_2$)$_a$—(V$_b$—R+).

Another aspect of the present invention includes a method of treatment (including prevention) of a viral infection in a mammal comprising administering to said mammal an antiviral effective amount of a compound of the present inventions Preferably the viral infection is an HIV infection.

Another aspect of the present invention includes a method of treatment (including prevention) of a bacterial infection in a mammal comprising administering to said mammal an effective amount of a compound of the present invention. Preferably the bacterium is *Yersinia pestis*.

Another aspect of the present invention includes a method of treatment (including prevention) of multiple sclerosis, rheumatoid arthritis, autoimmune diabetes, chronic implant rejection, asthma, rheumatoid arthritis, Crohns Disease, inflammatory bowel disease, chronic inflammatory disease, glomerular disease, nephrotoxic serum nephrits, kidney disease, Alzheimer's Disease, autoimmune encephalomyelitis, arterial thrombosis, allergic rhinitis, arteriosclerosis, Sjogren's syndrome (dermatomyositis), systemic lupus erythematosus, graft rejection, cancers with leukocyte infiltration of the skin or organs, infectious disorders including bubonic and pneumonic plague, human papilloma virus infection, prostate cancer, wound healing, amyotrophic lateral sclerosis and immune mediated disorders in a mammal comprising administering to said mammal a pharmceutically effective amount of a compound of the present invention.

Another aspect of the present invention includes a compound of the present invention for use in medical therapy.

Another aspect of the present invention includes the use of a compound of the present invention in the manufacture of a medicament for the treatment (including prophylaxis) of a viral infection. Preferably the viral infection is a HIV infection.

Another aspect of the present invention includes the use of a compound of the present invention in the manufacture of a medicament for the treatment, including prophylaxis, of a bacterial infection. Preferably the bacterium is *Yersinia pestis*.

Another aspect of the present invention includes the use of a compound of the present invention in the manufacture of a medicament for the treatment, including prophylaxis, of multiple sclerosis, rheumatoid arthritis, autoimmune diabetes, chronic implant rejection, asthma, rheumatoid arthritis, Crohns Disease, inflammatory bowel disease, chronic inflammatory disease, glomerular disease, nephrotoxic serum nephribs, kidney disease, Alzheimer's Disease, autoimmune encephalomyelitis, arterial thrombosis, allergic rhinitis, arteriosclerosis, Sjogren's syndrome (dermatomyositis), systemic lupus erythematosus, graft rejection, cancers with leukocyte infiltration of the skin or organs, infectious disorders including bubonic and pneumonic plague, human papilloma virus infection, prostate cancer, wound healing, amyotrophic lateral sclerosis and immune mediated disorders.

Another aspect of the present invention includes a pharmaceutical composition comprising a pharmaceutically effective amount of a compound of the present invention together with a pharmaceutically acceptable carrier. Preferably the pharmaceutical composition is in the form of a tablet, capsule, or liquid.

Another aspect of the present invention includes a method of treatment, including prevention, of a viral infection in a mammal comprising administering to said mammal a composition comprising a compound of the present invention and another therapeutic agent. Preferably the composition comprises one or more additional therapeutic agent selected from the group consisting of (1-alpha, 2-beta, 3-alpha)-9)-[2,3-bis(hydroxymethyl)cyclobutyl]guanine[(-)BHCG, SQ-34514, lobucavir], 9-[(2R,3R,4S)-3,4bis(hydroxymethyl)-2-oxetanosyl]adenine (oxetanocin-G), acyclic nucleosides, acyclovir, valaciclovir, famciclovir, ganciclovir, penciclovir, acyclic nucleoside phosphonates, (S)-1-(3-hydroxy-2-phosphonyl-methoxypropyl)cytosine (HPMPC), [[[2-(6-amino-9H-purin-9-yl)ethoxy]methyl]phosphinylidene]bis(oxymethylene)-2,2-dimethylpropanoic acid (bis-POM PMEA, adefovir dipivoxil), [[(1R)-2-(6-amino-9H-purin-9-yl)-1-methylethoxy]methyl]phosphonic acid (tenofovir), (R)-[[2-(6-Amino-9H-purin-9-yl)-1-methylethoxy]methyl]phosphonic acid bis-(isopropoxycarbonyloxymethyl)ester (bis-POC-PMPA), ribonucleotide reductase inhibitors, 2-acetylpyridine 5-[(2-chloroanilino)thiocarbonyl) thiocarbonohydrazone and hydroxyurea, nucleoside reverse transcriptase inhibitors, 3'-azido-3'-deoxythymidine (AZT, zidovudine), 2',3'-dideoxycytidine (ddC, zalcitabine), 2',3'-dideoxyadenosine, 2',3'-dideoxyinosine (ddI, didanosine), 2',3'-didehydrothymidine (d4T, stavudine), (-)-beta-D-2,6-diaminopurine dioxolane (DAPD), 3'-azido-2',3'-dideoxythymidine-5'-H-phosphophonate (phosphonovir), 2'-deoxy-5-iodo-uridine (idoxuridine), (-)-cis-1-(2-hydroxymethyl)-1,3-oxathiolane 5-yl)-cytosine (lamivudine), cis-1-(2-(hydroxymethyl)-1,3-oxathiolan-5-yl)-5-fluorocytosine (FTC), 3'-deoxy-3'-fluorothymidine, 5-chloro-2',3'-dideoxy-3'-fluorouridine, (-)-cis-4-[2-amino-6-(cyclopropylamino)-9H-purin-9-yl]-2-cyclopentene-1-methanol (abacavir), 9-[4-hydroxy-2-(hydroxymethyl)but-1-yl]-guanine (H2G), ABT-606 (2HM-H2G) ribavirin, protease inhibitors, indinavir, ritonavir, nelfinavir, amprenavir, saquinavir, fosamprenavir, (R)-N-tert-butyl-3-[(2S,3S)-2-hydroxy-3-N-[(R)-2-N-(isoquinolin-5-yloxyacetyl)amino-3-methylthiopropanoyl]amino-4-phenylbutanoyl]-5,5-dimethyl-1,3-thiazolidine-4-carboxamide (KNI-272), 4R-(4alpha,5alpha,6beta)]-1,3-bis[(3-aminophenyl) methyl]hexahydro-5,6-dihydroxy-4,7-bis(phenylmethyl)-2H-1,3-diazepin-2-one dimethanesulfonate (mozenavir), 3-[1-[3-[2-(5-trifluoromethylpyridinyl)-sulfonylamino]phenyl]propyl]-4-hydroxy-6alpha-phenethyl-6beta-propyl-5,6-dihydro-2-pyranone (tipranavir), N'-[2(S)-Hydroxy-3(S)-[N-(methoxycarbonyl)-I-tert-leucylamino]-4-phenylbutyl-N alpha-(methoxycarbonyl)-N'-[4-(2-pyridyl)benzyl]-L-tert-leucylhydrazide (BMS-232632), 3-(2(S)-Hydroxy-3(S)-(3-hydroxy-2-methylbenzamido)-4-phenylbutanoyl)-5,5-dimethyl-N-(2-methylbenzyl)thiazolidine-4(R)-carboxamide (AG-1776), N-(2(R)-hydroxy-1(S)-indanyl)-2(R)-phenylmethyl-4(S)-hydroxy-5-(1-(1-(4-benzo[b]furanylmethyl)-2(S)—N'-(tert-butylcarboxamido)piperazinyl)pentanamide (MK-944A), interferons, α-interferon, renal excretion inhibitors, probenecid, nucleoside transport inhibitors, dipyridamole, pentoxifyline, N-acetylcysteine (NAC), Procysteine, a crichosanthin, phosphonoformic acid, immunomodulators, interleukin II, thymosin, granulocyte macrophage colony stimulating factors, erythropoetin, soluble $CD_4$ and genetically engineered derivatives thereof, non-nucleoside reverse transcriptase inhibitors (NNRTIs), nevirapine (BI-RG-587), alpha-((2-acetyl-5-methylphenyl) amino)-2,6-dichloro-benzeneacetamide (loviride), 1-[3-(isopropylamino)-2-pyridyl]-4-[5-(methanesulfonamido)-1H-indol-2-ylcarbonyl]piperazine monomethanesulfonate (delavirdine), (10R, 11S, 12S)-12-hydroxy-6,6,10,11-tetramethyl-4-propyl-11,12-dihydro-2H,6H,10H-benzo(1,2-b: 3,4-b':5,6-b")tripyran-2-one ((+) calanolide A), (4S)-6-Chloro-4-[1E)-cyclopropylethenyl)-3,4-dihydro-4-(trifluoromethyl)-2(1H)-quinazolinone (DPC-083), (S)-6-chloro-4-(cyclopropylethynyl)-1,4-dihydro-4-(trifluoromethyl)-2H-3,1-benzoxazin-2-one (efavirenz, DMP 266), 1-(ethoxymethyl)-5-(1-methylethyl)-6-(phenylmethyl)-2,4(1H,3H)-pyrimidinedione (MKC-442), and 5-(3, 5dichlorophenyl)thio-4-isopropyl-1-(4-pyridyl)methyl-1H-imidazol-2-ylmethyl carbamate (capravirine), glycoprotein 120 antagonists, PRO-2000, PRO-542, 1,4-bis[3-[(2,4-dichlorophenyl)carbonylamino]-2-oxo-5,8-disodiumsulfanyl]naphthalyl-2, 5-dimethoxyphenyl-1,4-dihydrazone (FP-21399), cytokine antagonists, reticulose (Product-R), 1,1'-azobis-formamide (ADA), 1,11-(1,4-phenylenebis (methylene))bis-1,4,8,11-tetraazacyclotetradecane octahydrochloride (AMD-3100), integrase inhibitors, and fusion inhibitors.

Another aspect of the present invention includes a method of treatment, including prevention, of a viral infection in a mammal comprising administering to said mammal a composition comprising a compound of the present invention and ritonavir.

Particular compounds of the present invention include

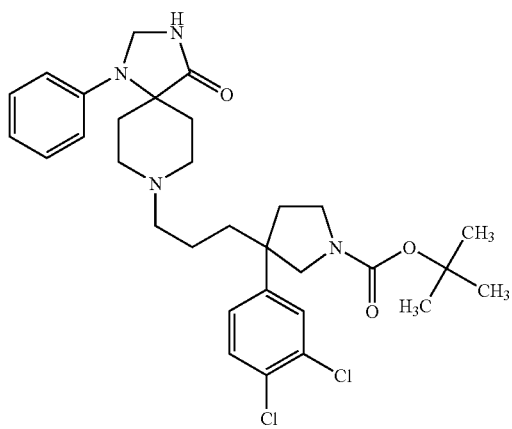

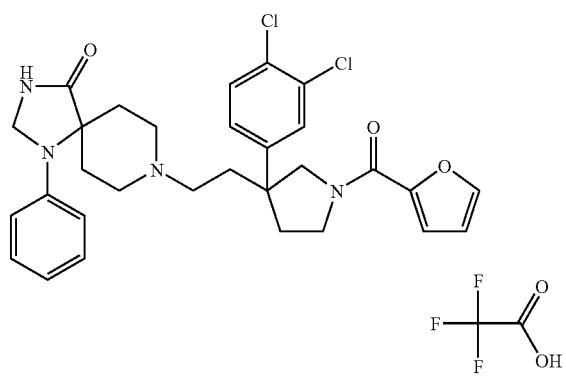

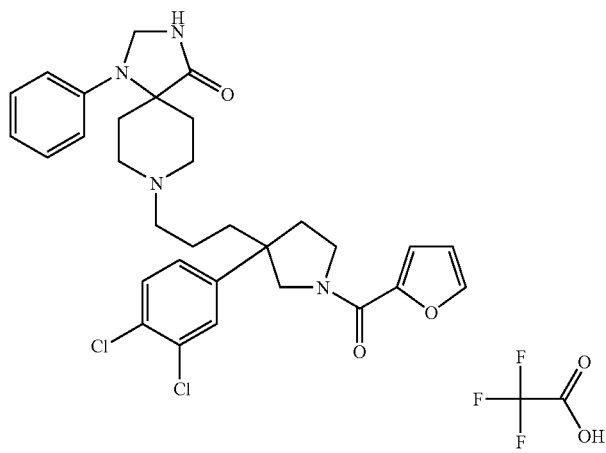
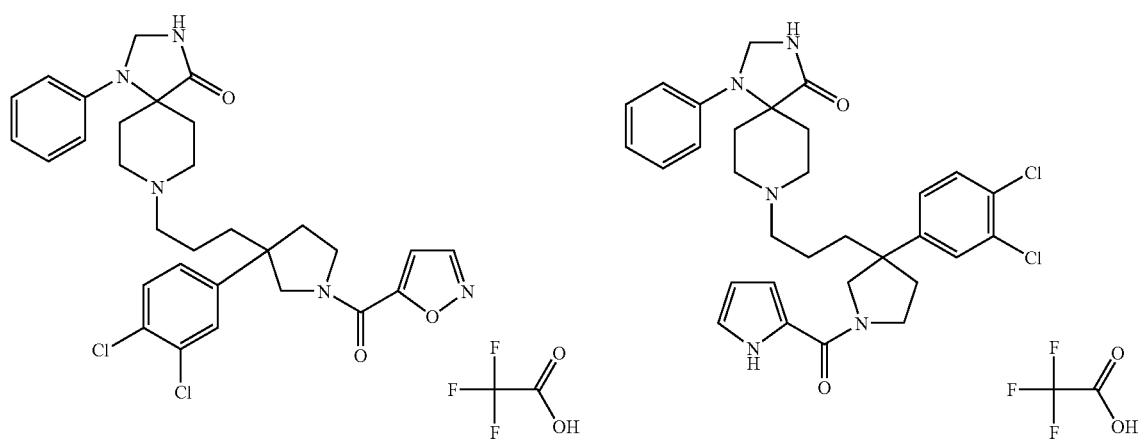
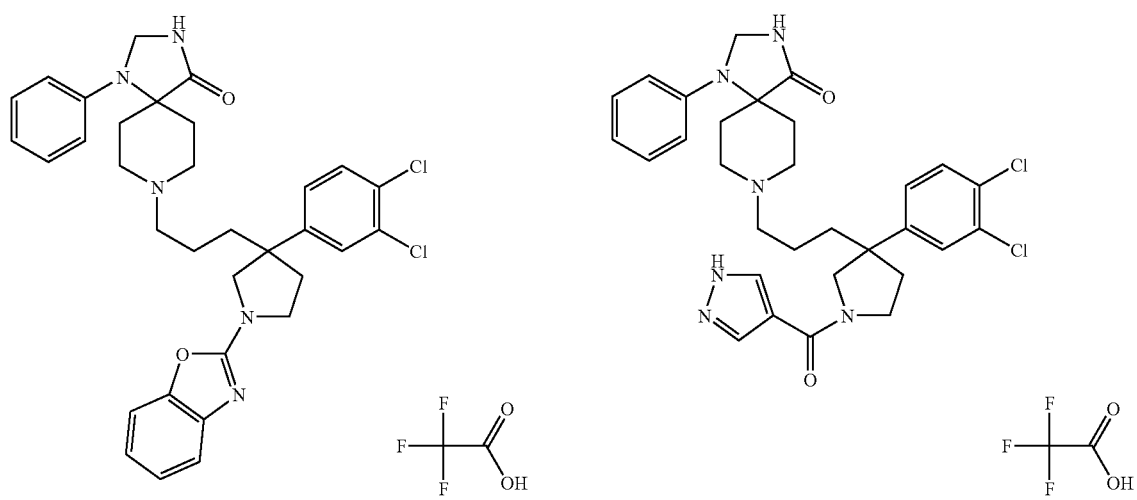

-continued
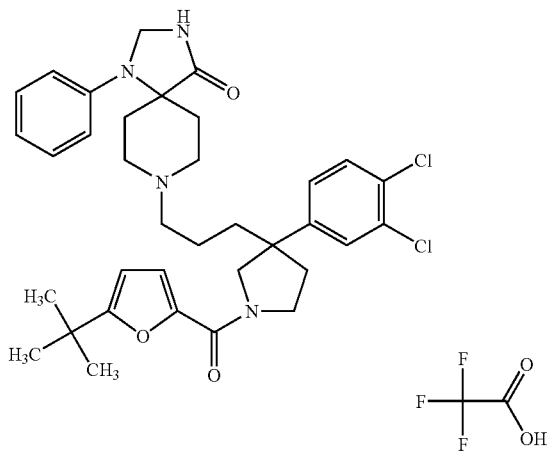
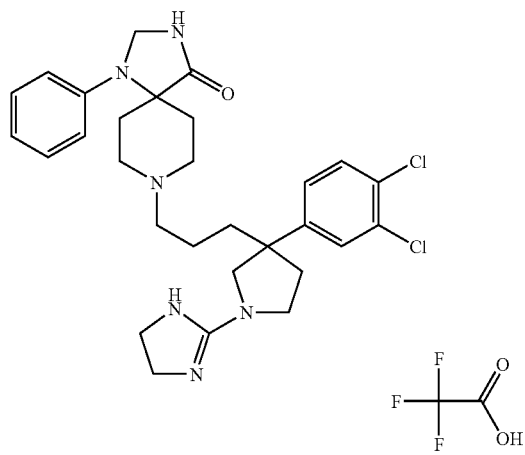
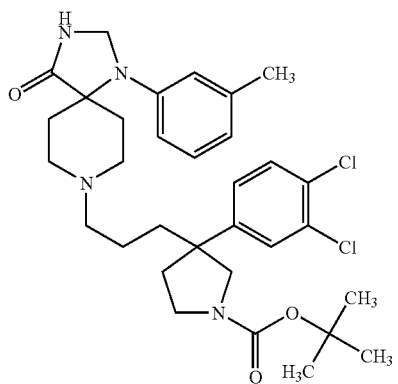
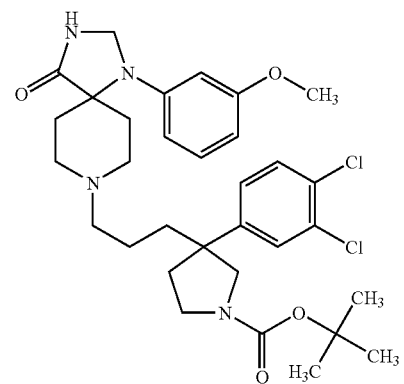
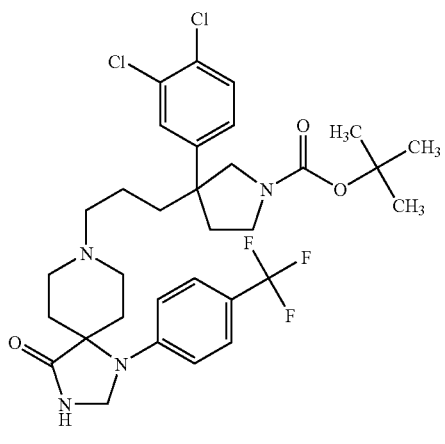
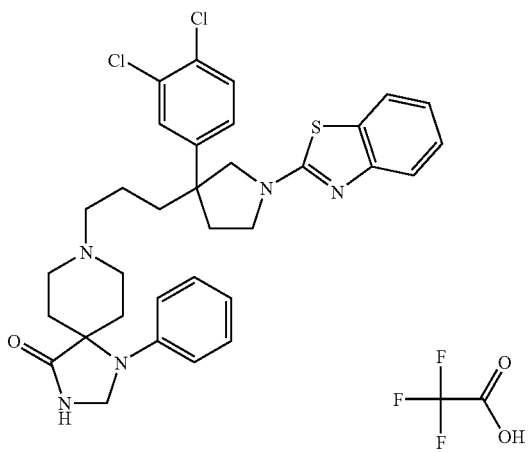

-continued
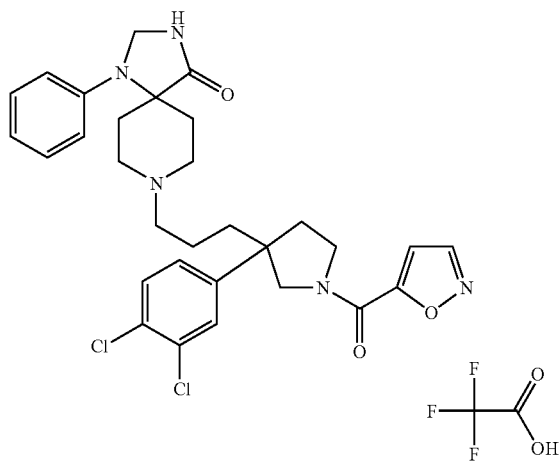
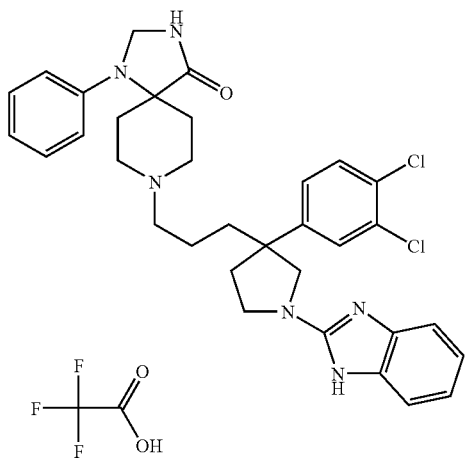
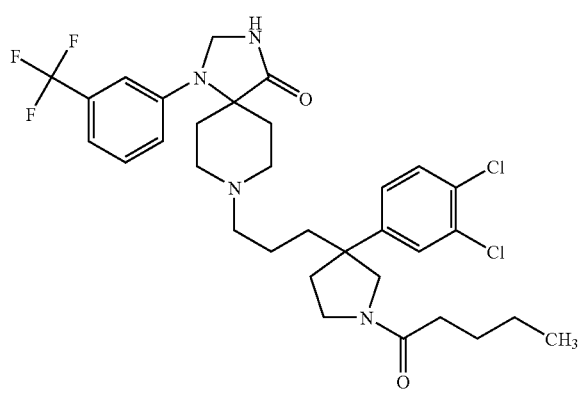
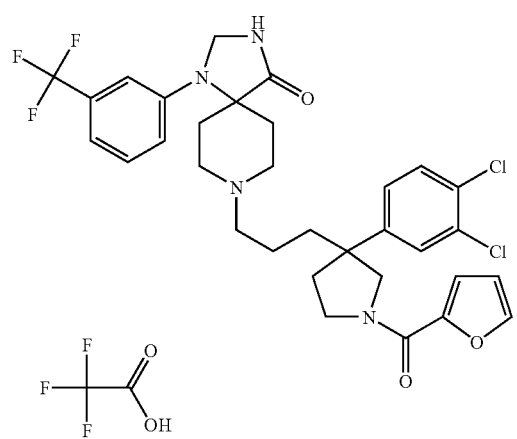
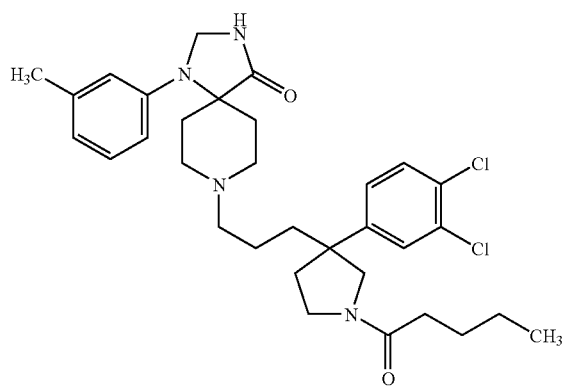
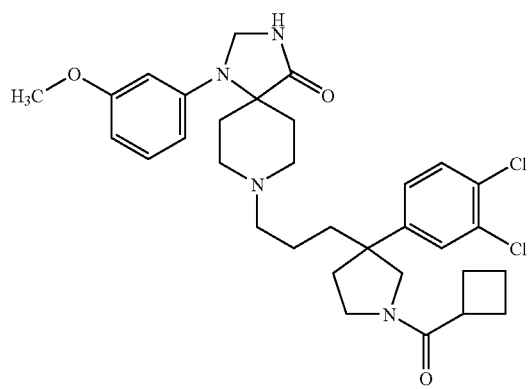
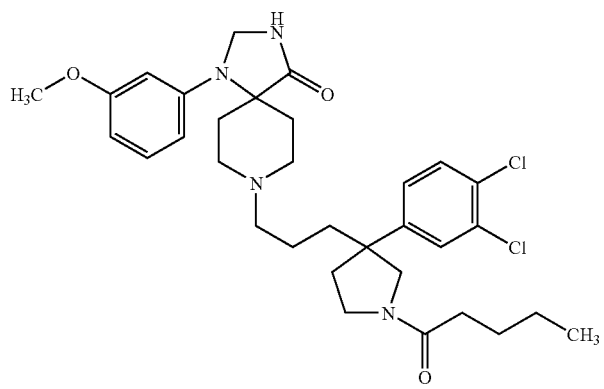

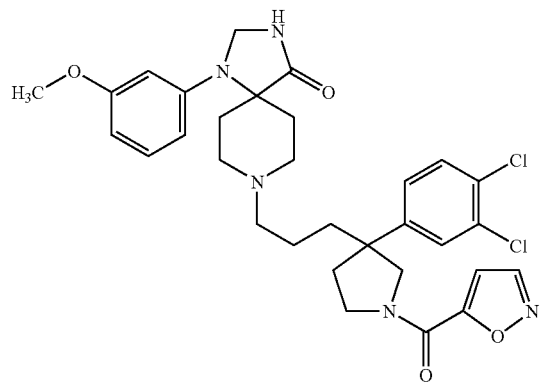
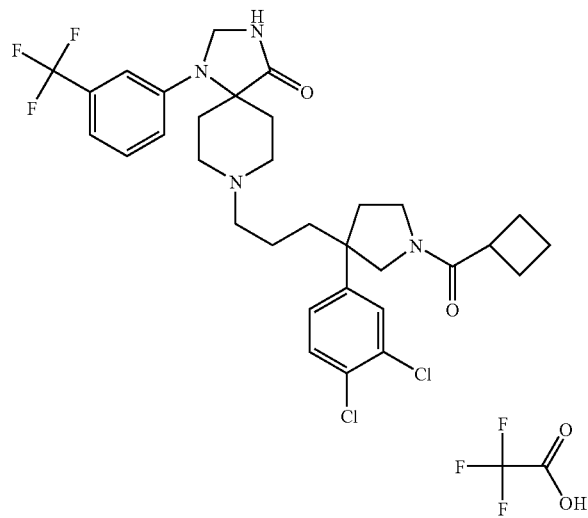
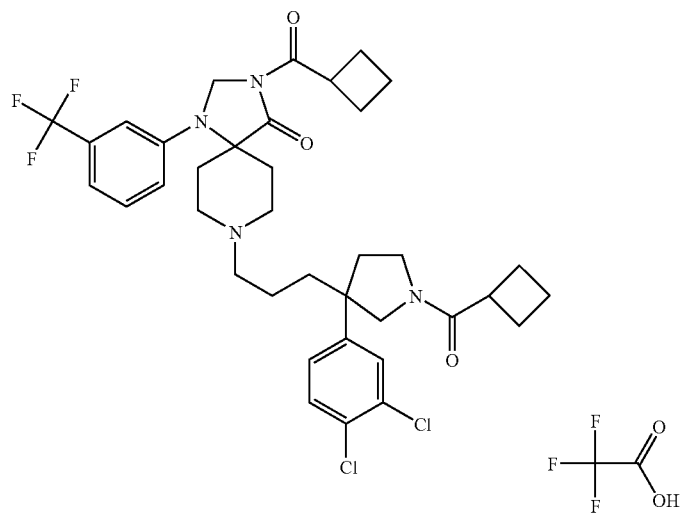
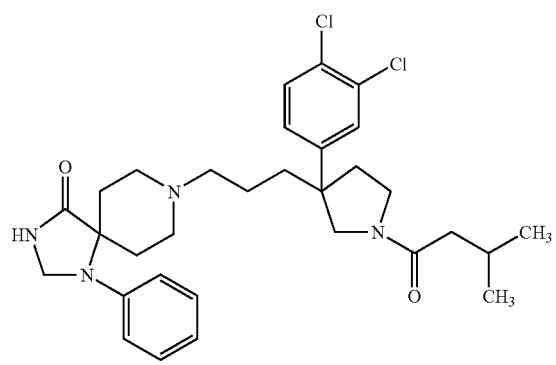

-continued
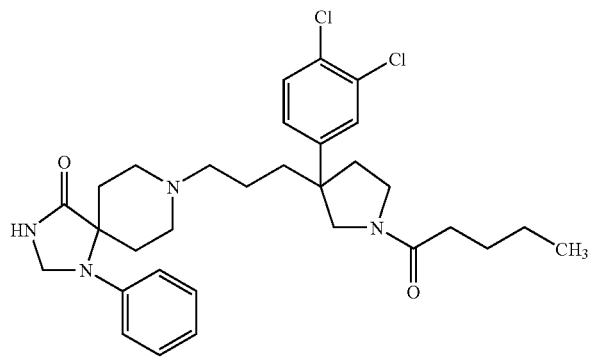
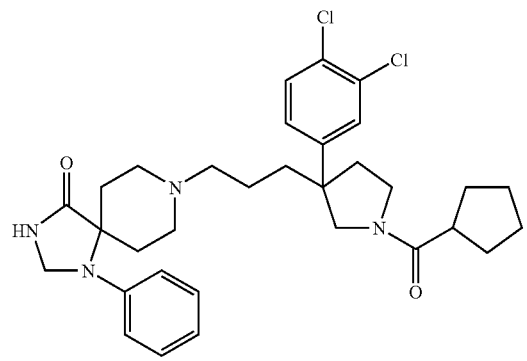
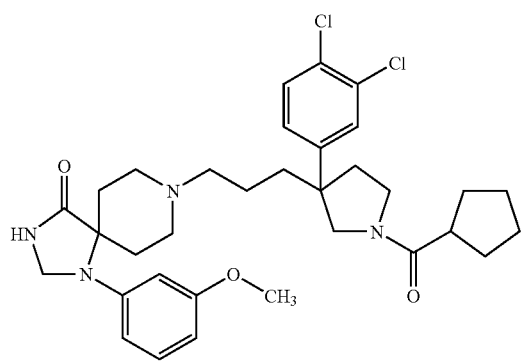
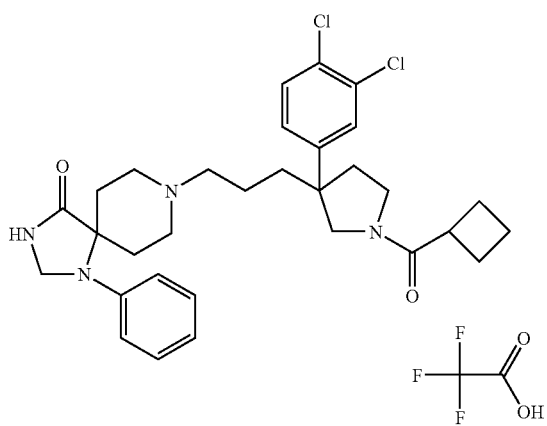
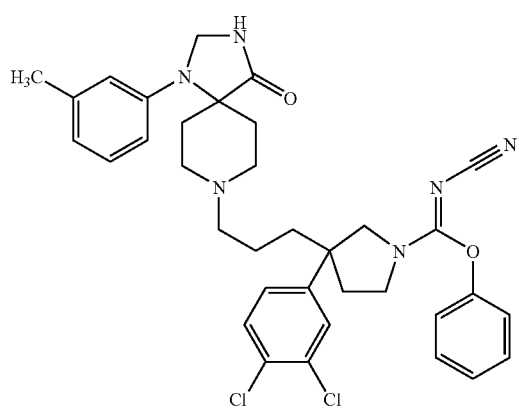
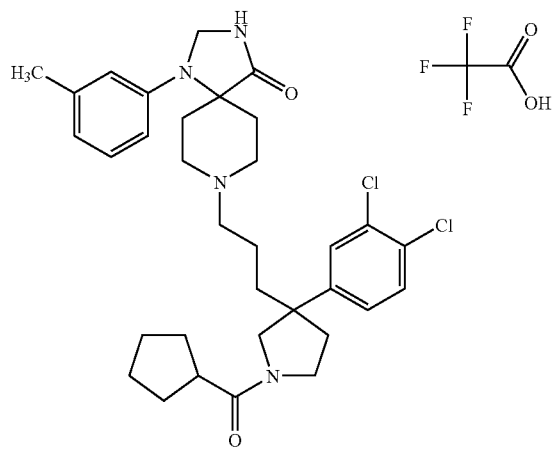

-continued
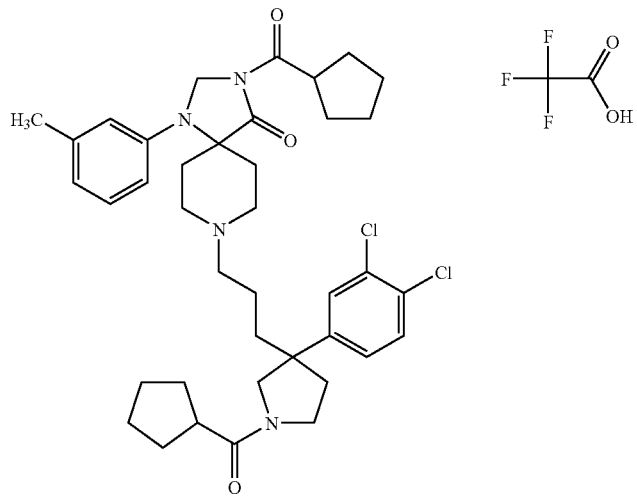 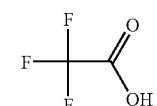
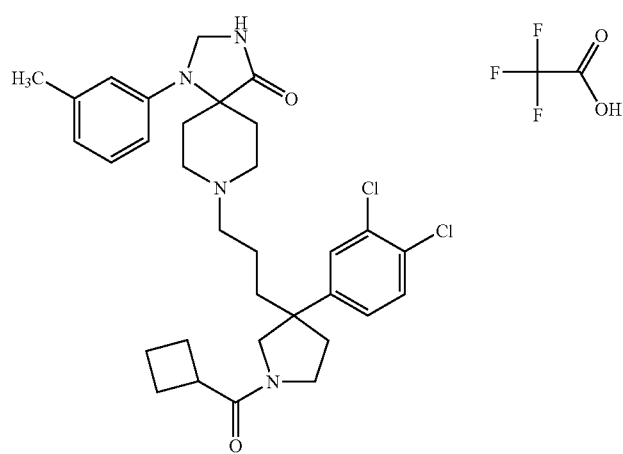 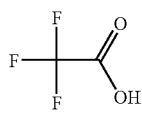
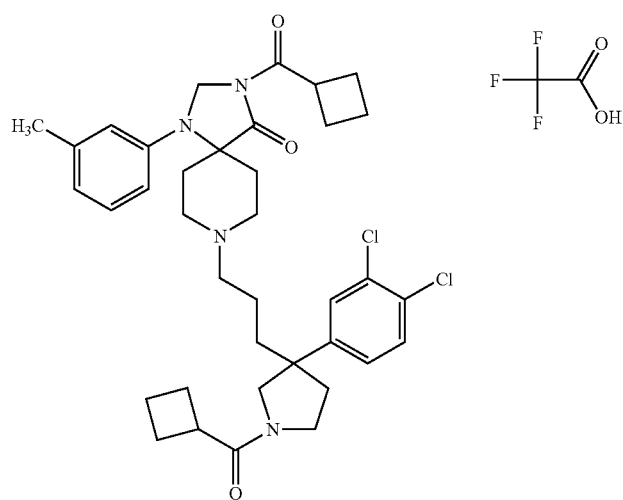 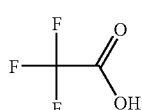

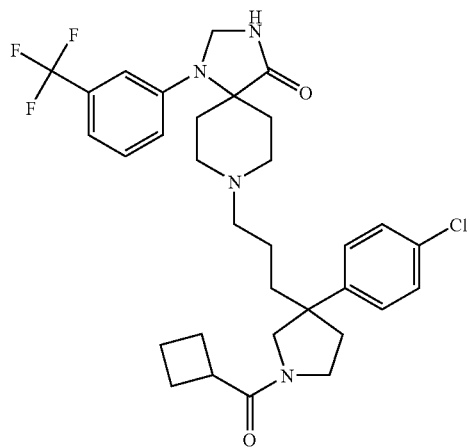
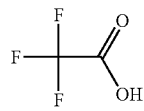
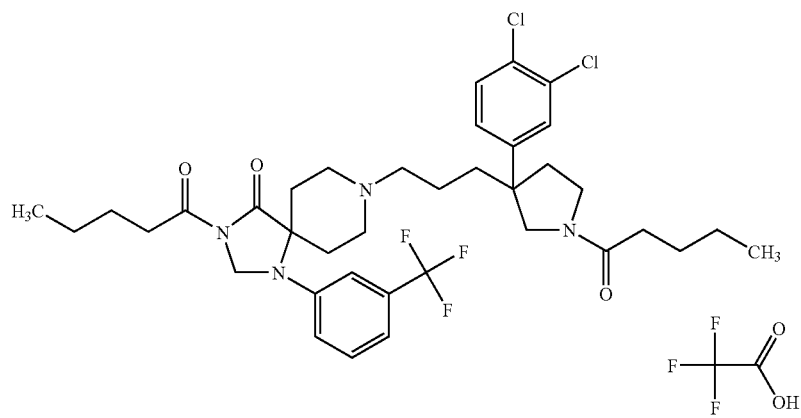
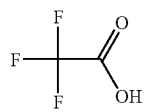
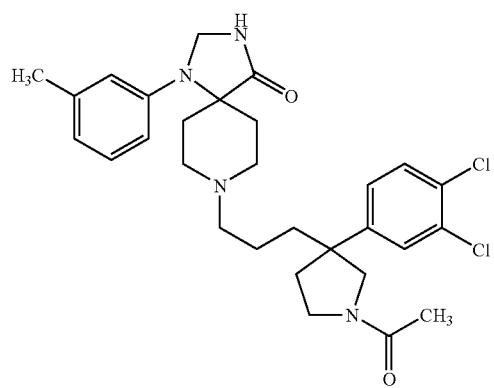
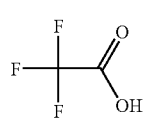

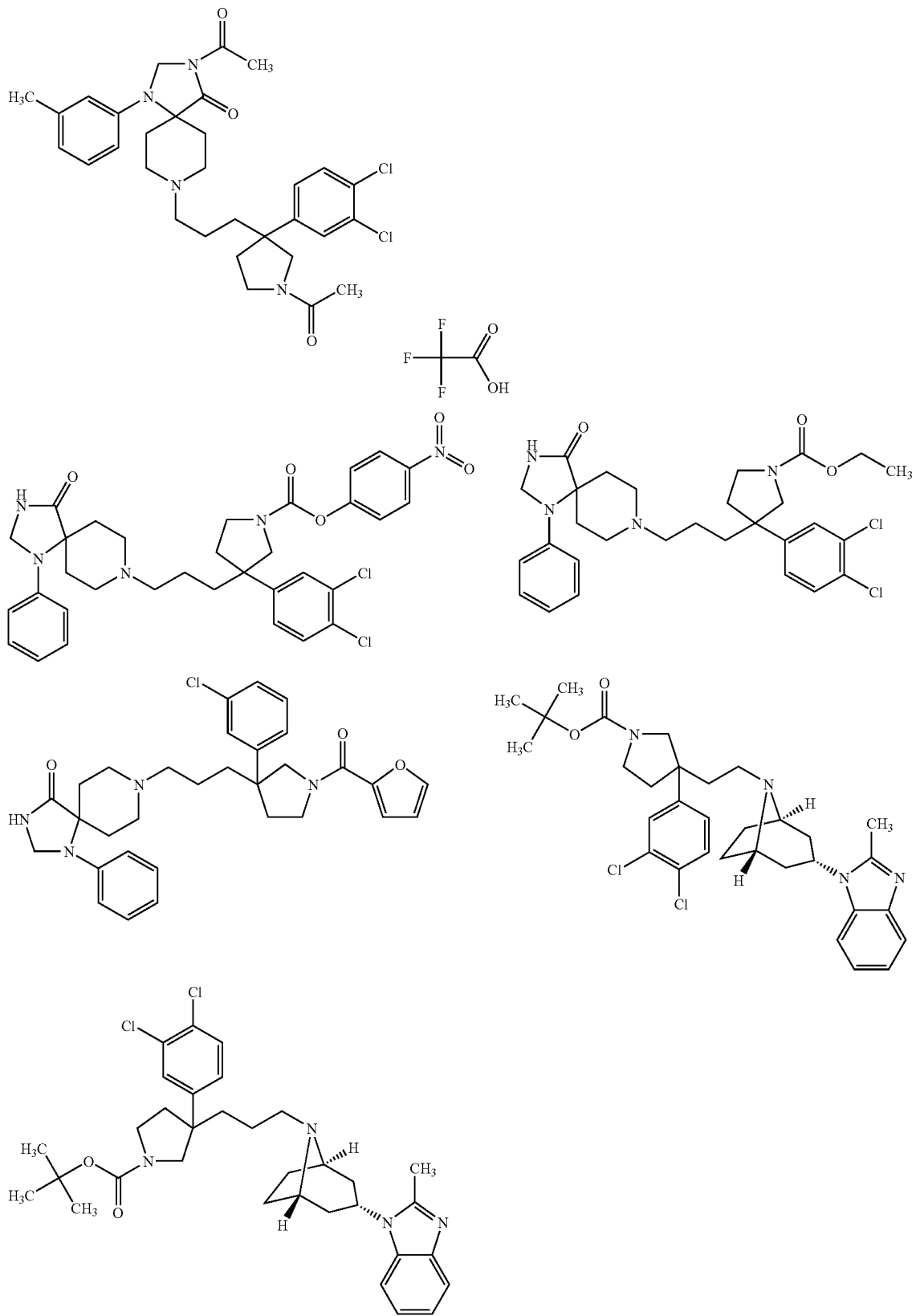

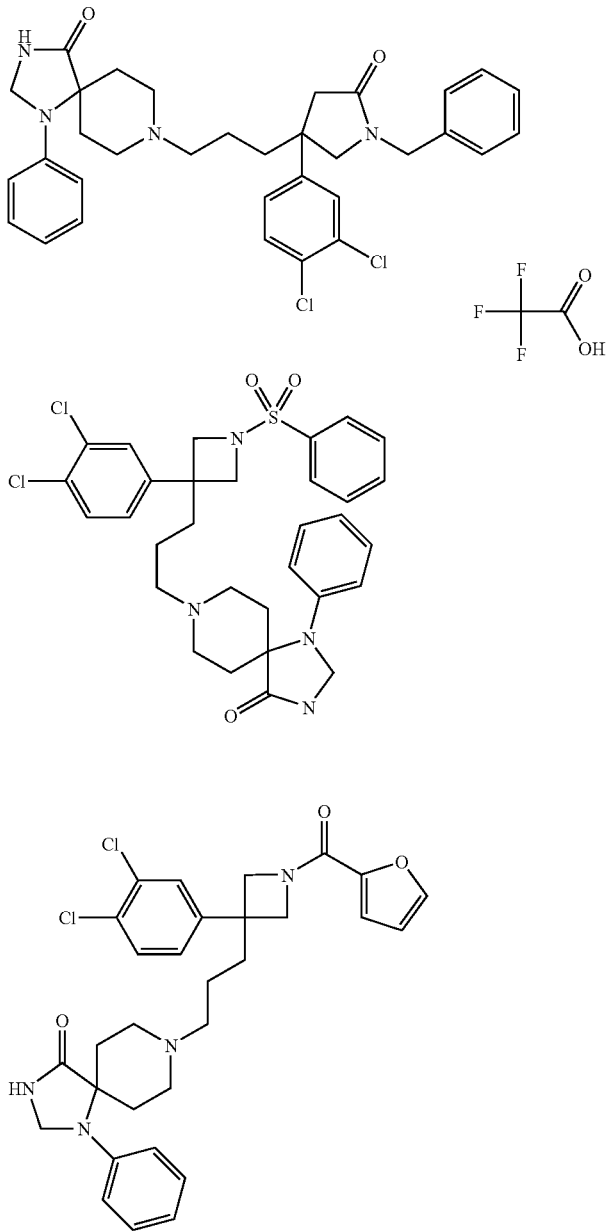
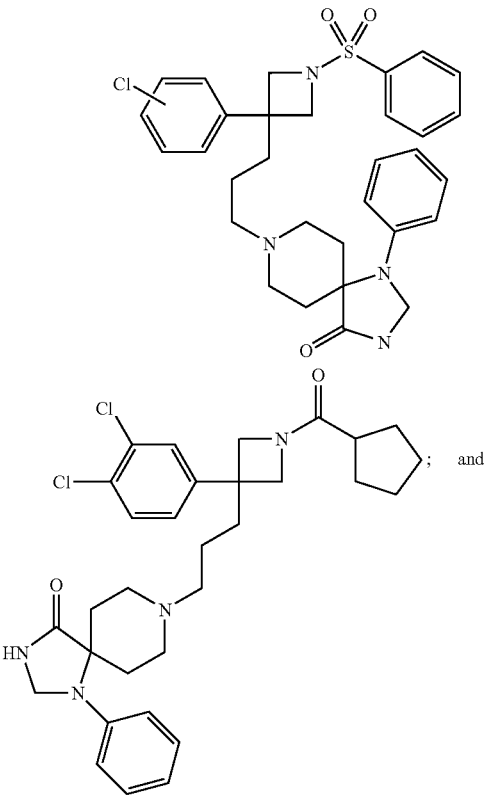

More particularly, the compounds of the present invention include:
tert-butyl 3-(3,4-dichlorophenyl)-3-[3-(4-oxo-1-phenyl-1,3,8-triazaspiro[4.5]dec-8-yl)propyl]pyrrolidine-1-carboxylate;
8-{3-[3-(3,4-dichlorophenyl)-1-(2-furoyl)pyrrolidin-3-yl]propyl}-1-phenyl-1,3,8-triazaspiro[4.5]decan-4-one;
8-{3-[3-(3,4-dichlorophenyl)-1-(isoxazol-5-ylcarbonyl)pyrrolidin-3-yl]propyl}-1-phenyl-1,3,8-triazaspiro[4.5]decan-4-one;
8-{3-[3-(3,4-dichlorophenyl)-1-(1H-pyrrol-2-ylcarbonyl)pyrrolidin-3-yl]propyl}-1-phenyl-1,3,8-triazaspiro[4.5]decan-4-one;
8-{3-[3-(3,4-dichlorophenyl)-1-pentanoylpyrrolidin-3-yl]propyl}-1-[3-(trifluoromethyl)phenyl]-1,3,8-triazaspiro[4.5]decan-4-one;

8-{3-[3-(3,4-dichlorophenyl)-1-(2-furoyl)pyrrolidin-3-yl]propyl}-1-[3-(trifluoromethyl)phenyl]-1,3,8-triazaspiro[4.5]decan-4-one;
8-{3-[1-(cyclobutylcarbonyl)-3-(3,4-dichlorophenyl)pyrrolidin-3-yl]propyl}-1-[3-(trifluoromethyl)phenyl]-1,3,8-triazaspiro[4.5]decan-4-one;
8-{3-[3-(3,4-dichlorophenyl)-1-pentanoylpyrrolidin-3-yl]propyl}-1-phenyl-1,3,8-triazaspiro[4.5]decan-4-one;
8-{3-[1-(cyclopentylcarbonyl)-3-(3,4-dichlorophenyl)pyrrolidin-3-yl]propyl}-1-phenyl-1,3,8-triazaspiro[4.5]decan-4-one;
8-{3-[1-(cyclobutylcarbonyl)-3-(3,4-dichlorophenyl)pyrrolidin-3-yl]propyl}-1-phenyl-1,3,8-triazaspiro[4.5]decan-4-one;

8-{3-[1-(cyclobutylcarbonyl)-3-(3,4-dichlorophenyl)pyrrolidin-3-yl]propyl}-1-(3-methylphenyl)-1,3,8-triazaspiro[4.5]decan-4-one;

3-acetyl-8-{3-[1-acetyl-3-(3,4-dichlorophenyl)pyrroidin-3-yl]propyl}-1-(3-methylphenyl)-1,3,8-triazaspiro[4.5]decan-4-one;

8-{3-[1-(1,3-benzoxazol-2-yl)-3-(3,4-dichlorophenyl)pyrrolidin-3-yl]propyl}-1-phenyl-1,3,8-triazaspiro[4.5]decan-4-one;

8-(2-{[3-(3,4-dichlorophenyl)-1-(2-furoyl)pyrrolidin-3-yl]oxy}ethyl)-1-phenyl-1,3,8-triazaspiro[4.5]decan-4-one;

8-(2-{[1-(cyclopentylcarbonyl)-3-(3,4-dichlorophenyl)pyrrolidin-3-yl]oxy}ethyl)-1-phenyl-1,3,8-triazaspiro[4.5]decan-4-one;

8-(2-{[1-acetyl-3-(3,4-dichlorophenyl)pyrrolidin-3-yl]oxy}ethyl)-1-phenyl-1,3,8-triazaspiro[4.5]decan-4-one;

8-(2-{[3-(3,4-dichlorophenyl)-1-(phenylsulfonyl)pyrrolidin-3-yl]oxy}ethyl)-1-phenyl-1,3,8-triazaspiro[4.5]decan-4-one;

8-(2-{[3-(3,4-dichlorophenyl)-1-(2-furoyl)pyrrolidin-3-yl]oxy}ethyl)-1-(3-methoxyphenyl)-1,3,8-triazaspiro[4.5]decan-4-one;

8-(2-{[1-(cyclopentylcarbonyl)-3-(3,4-dichlorophenyl)pyrrolidin-3-yl]oxy}ethyl)-1-(3-methoxyphenyl)-1,3,8-triazaspiro[4.5]decan-4-one;

8-(2-{[1-acetyl-3-(3,4-dichlorophenyl)pyrrolidin-3-yl]oxy}ethyl)-1-(3-methoxyphenyl)-1,3,8-triazaspiro[4.5]decan-4-one; and 8-(2-{[3-(3,4-dichlorophenyl)-1-(phenylsulfonyl)pyrrolidin-3-yl]oxy}ethyl)-1-(3-methoxyphenyl)-1,3,8triazaspiro[4.5]decan-4-one.

DETAILED DESCRIPTION OF THE INVENTION

The phrase "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other.

The term "alkyl", alone or in combination with any other term, refers to a straight-chain or branched-chain saturated aliphatic hydrocarbon radical containing the specified number of carbon atoms. Examples of alkyl radicals include, but are not limited to, methyl, ethyl, n-propyl, isopropyl, n-butyl, isobutyl, sec-butyl, tert-butyl, pentyl, isoamyl, n-hexyl and the like.

The term "cycloalkyl", "carbocylyl", "carbocyclic", or "carbocycle", or "carbocyclo", alone or in combination with any other term, refers to a monocyclic or polycyclic non-aromatic hydrocarbon ring radical having three to twenty carbon atoms, preferably from three to twelve carbon atoms, and more preferably from three to ten carbon atoms. If polycyclic, each ring in a carbocylyl radical is non-aromatic unless otherwise indicated. A carbocylyl radical is either completely saturated or contains one or more units of unsaturation but is not aromatic. The unsaturation, if present, may occur in any point in the ring that may result in any chemically stable configuration. The term "cycloalkyl", "carbocylyl", "carbocyclic", or "carbocycle", or "carbocyclo" also includes hydrocarbon rings that are fused to one or more aromatic rings, such as in tetrahydronaphthyl, where the radical or point of attachment is on the non-aromatic ring.

Unless otherwise indicated, the term "cycloalkyl", "carbocylyl", "carbocyclic", or "carbocycle", or "carbocyclo" also includes each possible positional isomer of a non-aromatic hydrocarbon radical, such as in 1-decahydronaphthyl, 2-decahydronaphthyl, 1-tetrahydronaphthyl and 2-tetrahydronaphthyl. Examples of suitable cycloalkyl groups include, but are not limited to, cyclopropyl, cyclobutyl, cyclopentyl, cyclohexyl, cyclohexenyl, decahydronaphthyl, tetrahydronaphthyl and the like.

The term "alkenyl," alone or in combination with any other term, refers to a straight-chain or branched-chain alkyl group with at least one carbon-carbon double bond. Examples of alkenyl radicals include, but are not limited to, ethenyl, propenyl, isopropenyl, butenyl, isobutenyl, pentenyl, hexenyl, hexadienyl and the like.

The term "alkynyl" refers to hydrocarbon groups of either a straight or branched configuration with one or more carbon-carbon triple bonds which may occur in any stable point along the chain, such as ethynyl, propynyl, butynyl, pentynyl, and the like.

The term "alkoxy" refers to an alkyl ether radical, wherein the term "alkyl" is defined above. Examples of suitable alkyl ether radicals include, but are not limited to, methoxy, ethoxy, n-propoxy, isopropoxy, n-butoxy, isobutoxy, sec-butoxy, tert-butoxy and the like.

The term "aryl", alone or in combination with any other term, refers to an aromatic monocyclic or polycyclic hydrocarbon ring radical containing five to twenty carbon atoms, preferably from six to fourteen carbon atoms, and more preferably from six to ten carbon atoms. Also included within the scope of the term "aryl", as it is used herein, is a group in which an aromatic hydrocarbon ring is fused to one or more non-aromatic carbocyclic or heteroatom-containing rings, such as in an indanyl, phenanthridinyl or tetrahydronaphthyl, where the radical or point of attachment is on the aromatic hydrocarbon ring.

Unless otherwise indicated, the term "aryl" also includes each possible positional isomer of an aromatic hydrocarbon radical, such as in 1-naphthyl, 2-naphthyl, 5-tetrahydronaphthyl, 6-tetrahydronaphthyl, 1-phenanthridinyl, 2-phenanthridinyl, 3-phenanthridinyl, 4-phenanthridinyl, 7-phenanthridinyl, 8-phenanthridinyl, 9-phenanthridinyl and 10-phenanthridinyl. Examples of aryl radicals include, but are not limited to, phenyl, naphthyl, indenyl, azulenyl, fluorenyl, anthracenyl, phenanthrenyl, tetrahydronaphthyl, indanyl, phenanthridinyl and the like.

The term "aralkyl" further refers to groups of —$R_aR_b$, where $R_a$ is an alkylene as defined herein and $R_b$ is an aryl as defined herein.

The term "heterocycle", "heterocyclic", and "heterocyclyl", alone or in combination with any other term, refers to a non-aromatic monocyclic or polycyclic ring radical containing three to twenty carbon atoms, preferably three to seven carbon atoms if monocyclic and eight to eleven carbon atoms if bicyclic, and in which one or more ring carbons, preferably one to four, are each replaced by a heteroatom such as N, O, and S. If polycyclic, each ring in a heterocyclyl radical is non-aromatic unless otherwise indicated. A heterocyclic ring may be fully saturated or may contain one or more units of unsaturation but is not aromatic. The unsaturation, if present, may occur in any point in the ring that may result in any chemically stable configuration. The heterocyclic ring may be attached at a carbon or heteroatom that results in the creation of a stable structure. Preferred heterocycles include 5-7 membered monocyclic heterocycles and 8-10 membered bicyclic heterocycles.

Also included within the scope of the term "heterocycle", "heterocyclic", or "heterocyclyl" is a group in which a non-aromatic heteroatom-containing ring is fused to one or more aromatic rings, such as in an indolinyl, chromanyl, phenanthridinyl or tetrahydroquinolinyl, where the radical or point of attachment is on the non-aromatic heteroatom-containing ring. Unless otherwise indicated, the term "heterocycle", "heterocyclic", or "heterocyclyl" also includes each possible positional isomer of a heterocyclic radical, such as in 1-decahydroquinoline, 2-decahydroquinoline, 3-decahydroquinoline, 4-decahydroquinoline, 5-decahydroquinoline, 6-decahydroquinoline, 7-decahydroquinoline, 7-decahydroquinoline, 8-decahydroquinoline, 4a-decahydroquinoline, 8a-decahydroquinoline, 1-indolinyl, 2-indolinyl, 3-indolinyl, 1-tetrahydroquinoline, 2-tetrahydroquinoline, 3-tetrahydroquinoline and 4-tetrahydroquinoline. The term "heterocyclylalkyl" refers to an alkyl group substituted by a heterocyclyl.

Examples of heterocyclic groups include, but are not limited to, imidazolinyl, 2,3-dihydro-1H-imidazolyl, imidazolidinyl, indazolinolyl, perhydropyridazyl, pyrrolinyl, pyrrolidinyl, 4H-pyrazolyl, piperidinyl, pyranyl, pyrazolinyl, piperazinyl, morpholinyl, thiamorpholinyl, thiazolidinyl, thiamorpholinyl, oxopiperidinyl, oxopyrrolidinyl, azepinyl, tetrahydrofuranyl, oxoazepinyl, tetrahydropyranyl, thiazolyl, dioxolyl, dioxinyl, oxathiolyl, benzodioxolyl, dithiolyl, dithiolanyl, tetrahydrothiophenyl, sulfolanyl, dioxanyl, dioxolanyl, tetrahydrofurodihydrofuranyl, dihydropyranyl, tetrahydropyranodihydrofuranyl, tetradyrofurofuranyl, tetrahydropyranofuranyl, diazolonyl, phthalimidinyl, benzoxanyl, benzopyrrolidinyl, benzopiperidinyl, benzoxolanyl, benzothiolanyl and benzothianyl.

The term "heteroaryl", alone or in combination with any other term, refers to an aromatic monocyclic or polycyclic ring radical containing five to twenty carbon atoms, preferably five to ten carbon atoms, in which one or more ring carbons, preferably one to four, are each replaced by a heteroatom such as N, O, and S. Preferred heteroaryl groups include 5-6 membered monocyclic heteroaryls and 8-10 membered bicyclic heteroaryls.

Also included within the scope of the term "heteroaryl" is a group in which a heteroaromatic ring is fused to one or more aromatic or non-aromatic rings where the radical or point of attachment is on the heteroaromatic ring. Examples include, but are not limited to, pyrido[3,4-d]pyrimidinyl, 7,8-dihydro-pyrido[3,4-d]pyrimidine and 5,6,7,8-tetrahydro-pyrido[3,4-d]pyrimidine. Unless otherwise indicated, the term "heteroaryl" also includes each possible positional isomer of a heteroaryl radical, such as in 2-pyrido[3,4-d]pyrimidinyl and 4-pyrido[3,4-d]pyrimidinyl.

Examples of heteroaryl groups include, but are not limited to, imidazolyl, quinolyl, isoquinolyl, indolyl, indazolyl, pyridazyl, pyridyl, pyrrolyl, pyrazolyl, pyrazinyl, quinoxalyl, pyrimidinyl, pyridazinyl, furyl, thienyl, triazolyl, thiazolyl, carbazolyl, carbolinyl, tetrazolyl, benzofuranyl, oxazolyl, benzoxazolyl, isoxozolyl, isothiazolyl, thiadiazolyl, furazanyl, oxadiazolyl, benzimidazolyl, benzothienyl, quinolirnyl, benzotriazolyl, benzothiazolyl, isoquinolinyl, isoindolyl, acridinyl and benzoisoxazolyl.

The term "heteroaralkyl" further refers to groups of —$R_aR_b$, where $R_a$ is an alkylene as defined herein and $R_b$ is a heteroaryl as defined herein.

The term "heteroatom" means nitrogen, oxygen, phosphorus, or sulfur and includes any oxidized forms thereof, including as non-limiting examples oxidized forms of nitrogen such as $N(O)\{N^+\!\!-\!\!O^-\}$, oxidized forms of sulfur such as $S(O)$ and $S(O)_2$, and the quaternized form of any basic nitrogen.

The term "halogen" refers to fluorine, chlorine, bromine or iodine.

The term "pharmaceutically effective amount" refers to an amount of a compound of the invention that is effective in treating a CCR5-related disease, for example a virus infection, for example an HIV infection, in a patient either as monotherapy or in combination with other agents. The term "treatment" as used herein refers to the alleviation of symptoms of a particular disorder in a patient, or the improvement of an ascertainable measurement associated with a particular disorder, and may include the suppression of symptom recurrence in an asymptomatic patient such as a patient in whom a viral infection has become latent. The term "prophylaxis" refers to preventing a disease or condition or preventing the occurrence of symptoms of such a disease or condition, in a patient. As used herein, the term "patient" refers to a mammal, including a human.

The term "pharmaceutically acceptable carrier" refers to a carrier that may be administered to a patient, together with a compound of this invention, and which does not destroy the pharmacological activity thereof and is nontoxic when administered in doses sufficient to deliver a therapeutic amount of the therapeutic agent.

The term "pharmaceutically acceptable derivative" means any pharmaceutically acceptable salt, ester, salt of an ester, or other derivative of a compound of this invention which, upon administration to a recipient, is capable of providing (directly or indirectly) a compound of this invention or an inhibitorily active metabolite or residue thereof. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species.

Pharmaceutically acceptable salts of the compounds according to the invention include those derived from pharmaceutically acceptable inorganic and organic acids and bases. Examples of suitable acids include hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, ethanesulfonic, formic, benzoic, malonic, naphthalene-2-sulfonic and benzenesulfonic acids. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g. sodium), alkaline earth metal (e.g., magnesium), ammonium, $NW_4^+$ (wherein W is $C_{1-4}$ alkyl) and other amine salts. Physiologically acceptable salts of a hydrogen atom or an amino group include salts of organic carboxylic acids such as acetic, lactic, tartaric, malic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids. Physiologically acceptable salts of a compound with a hydroxy group include the anion of said compound in combination with a suitable cation such as $Na^+$, $NH_4^+$, and $NW_4^+$ (wherein W is a $C_{1-4}$alkyl group).

Any reference to any of the above compounds also includes a reference to a pharmaceutically acceptable salt thereof.

Salts of the compounds of the present invention may be made by methods known to a person skilled in the art. For example, treatment of a compound of the present invention with an appropriate base or acid in an appropriate solvent will yield the corresponding salt.

Esters of the compounds of the present invention are independently selected from the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted by, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$) acyl glycerol.

In such esters, unless otherwise specified, any alkyl moiety present advantageously contains from 1 to 18 carbon atoms, particularly from 1 to 6 carbon atoms, more particularly from 1 to 4 carbon atoms, Any cycloalkyl moiety present in such esters advantageously contains from 3 to 6 carbon atoms. Any aryl moiety present in such esters advantageously comprises a phenyl group.

The compounds according to the invention contain one or more asymmetric carbon atoms and thus occur as racemates and racemic mixtures, single enantiomers, diastereomeric mixtures and individual diastereoisomers. All such isomeric forms of these compounds are expressly included in the present invention. Each stereogenic carbon may be of the R or S configuration. Although the specific compounds exemplified in this application may be depicted in a particular stereochemical configuration, compounds having either the opposite stereochemistry at any given chiral center or mixtures thereof are also envisioned.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}C$- or $^{14}C$-enriched carbon are also within the scope of this invention.

Certain compounds of this invention may exist in alternative tautomeric forms. All such tautomeric forms of the present compounds are within the scope of the invention. Unless otherwise indicated, the representation of either tautomer is meant to include the other.

The present invention features compounds according to the invention for use in medical therapy, for example for the treatment including prophylaxis of viral infections such as an HIV infections and associated conditions. Reference herein to treatment extends to prophylaxis as well as the treatment of established infections, symptoms, and associated clinical conditions such as AIDS related complex (ARC), Kaposi's sarcoma, and AIDS dementia.

The present invention features use of the compounds of the present invention in the manufacture of a medicament for the treatment including prophylaxis of a CCR5-related disease or condition, for example, a viral infection, for example, an HIV. infection.

According to another aspect, the present invention provides a method for the treatment including prevention of the symptoms or effects of a viral infection in an infected animal, for example, a mammal including a human, which comprises treating said animal with a pharmaceutically effective amount of a compound according to the invention. According to one aspect of the invention, the viral infection is a retroviral infection, in particular an HIV infection. A further aspect of the invention includes a method for the treatment including prevention of the symptoms or effects of an HBV infection.

The compounds according to the invention may also be used in adjuvant therapy in the treatment of HIV infections or HIV-associated symptoms or effects, for example Kaposi's sarcoma.

The compounds of the present invention may also be used in the treatment including prevention of other CCR5-related diseases and conditions, including multiple sclerosis, rheumatoid arthritis, autoimmune diabetes, chronic implant rejection, asthma, rheumatoid arthritis, Crohns Disease, inflammatory bowel disease, chronic inflammatory disease, glomerular disease, nephrotoxic serum nephritis, kidney disease, Alzheimer's Disease, autoimmune encephalomyelitis, arterial thrombosis, allergic rhinitis, arteriosclerosis, Sjogren's syndrome (dermatomyositis), systemic lupus erythematosus, graft rejection, cancers with leukocyte infiltration of the skin or organs, infectious disorders including bubonic and pneumonic plague, human papilloma virus infection, prostate cancer, wound healing, amyotrophic lateral sclerosis, immune mediated disorders.

The present invention further provides a method for the treatment of a clinical condition in an animal, for example, a mammal including a human which clinical condition includes those which have been discussed hereinbefore, which comprises treating said animal with a pharmaceutically effective amount of a compound according to the invention. The present invention also includes a method for the treatment including prophylaxis of any of the aforementioned diseases or conditions.

In yet a further aspect, the present invention provides the use of a compound according to the invention in the manufacture of a medicament for the treatment including prophylaxis of any of the above mentioned viral infections or conditions.

The above compounds according to the invention and their pharmaceutically acceptable derivatives may be employed in combination with other therapeutic agents for the treatment of the above infections or conditions. Combination therapies according to the present invention comprise the administration of a compound of the present invention or a pharmaceutically acceptable derivative thereof and another pharmaceutically active agent. The active ingredient(s) and pharmaceutically active agents may be administered simultaneously in either the same or different pharmaceutical compositions or sequentially in any order. The amounts of the active ingredient(s) and pharmaceutically active agent(s) and the relative timings of administration will be selected in order to achieve the desired combined therapeutic effect.

Examples of such therapeutic agents include agents that are effective for the treatment of viral infections or associated conditions. Among these agents are (1-alpha, 2-beta, 3-alpha)-9-[2,3-bis(hydroxymethyl)cyclobutyl]guanine [(−) BHCG, SQ-34514, lobucavir], 9-[(2R,3R,4S)-3,4-bis(hydroxymethyl)-2-oxetanosyl]adenine (oxetanocin-G), acyclic nucleosides, for example acyclovir, valaciclovir, famciclovir, ganciclovir, and penciclovir, acyclic nucleoside phosphonates, for example (S)-1-(3-hydroxy-2-phosphonylmethoxypropyl)cytosine (HPMPC), [[[2-(6-amino-9H- purin-9-yl)ethoxy]methyl]phosphinylidene]bis (oxymethylene)-2,2-dimethylpropanoic acid (bis-POM PMEA, adefovir dipivoxil), [[(1R)-2-(6-amino-9H-purin-9-yl)-1-methylethoxy]methyl]phosphonic acid (tenofovir), and (R)-[[2-(6-Amino-9H-purin-9-yl)-1-methylethoxy]methyl]phosphonic acid bis-(isopropoxycarbonyloxymethyl) ester (bis-POC-PMPA), ribonucleotide reductase inhibitors, for example 2-acetylpyridine 5-[(2-chloroanilino)thiocarbonyl)thiocarbonohydrazone and hydroxyurea, nucleoside reverse transcriptase inhibitors, for example 3'-azido-3'-deoxythymidine (AZT, zidovudine), 2',3'-dideoxycytidine (ddC, zalcitabine), 2',3'-dideoxyadenosine, 2',3'-dideoxyinosine (ddI, didanosine), 2',3'-didehydrothymidine (d4T, stavudine), (−)-beta-D-2,6-diaminopurine dioxolane (DAPD), 3'-azido-2',3'-dideoxythymidine-5'-H-phosphophonate (phosphonovir), 2'-deoxy-5-iodo-uridine (idoxuridine), (−)-cis-1-(2-hydroxymethyl)-1,3-oxathiolane 5-yl)-cytosine (lamivudine), cis-1-(2-(hydroxymethyl)-1,3-oxathiolan-5-yl)-5-fluorocytosine (FTC), 3'-deoxy-3'-fluorothymidine, 5-chloro-2',3'-dideoxy-3'-fluorouridine, (−)-cis-4-[2-amino-6-(cyclopropylamino)-9H-purin-9-yl]-2-cyclopentene-1-methanol (abacavir), 9-[4-hydroxy-2-(hydroxymethyl)but-1-yl]-guanine (H2G), ABT-606 (2HM-H2G) and ribavirin, protease inhibitors, for example indinavir, ritonavir, nelfinavir, amprenavir, saquinavir, fosamprenavir, (R-N-tert-butyl-3-[(2S,3S)-2-hydroxy-3-N-[(R)-2-N-(isoquinolin-5-yloxyacetyl)amino-3-methylthiopropanoyl]amino-4-phenylbutanoyl]-5,5-dimethyl-1,3-thiazolidine-4-carboxamide (KNI-272),4R-(4alpha,5alpha,6beta)]-1,3-bis[(3-aminophenyl)methyl]hexahydro-5,6-dihydroxy-4,7-bis (phenylmethyl)-2H-1,3-diazepin-2-one dimethanesulfonate (mozenavir), 3-[1-[3-[2-(5-trifluoromethylpyridinyl)-sulfonylamino]phenyl]propyl]-4-hydroxy-6alpha-phenethyl-6beta-propyl-5,6-dihydro-2-pyranone (tipranavir), N'-[2(S)-Hydroxy-3(S)-[N-(methoxycarbonyl)-1-tert-leucylamino]-4-phenylbutyl-N$^{alpha}$-(methoxycarbonyl)-N'-[4-(2-pyridyl) benzyl]-L-tert-leucylhydrazide (BMS-232632), 3-(2(S)-Hydroxy-3(S)-(3-hydroxy-2-methylbenzamido)-4-phenylbutanoyl)-5,5-dimethyl-N-(2-methylbenzyl) thiazolidine-4(R)-carboxamide (AG-1776), N-(2(R)-hydroxy-1(S)-indanyl)-2(R)-phenyl-methyl-4(S)-hydroxy-5-(1-(1-(4-benzo[b]furanylmethyl)-2(S)-N'-(tert-butylcarboxamido)piperazinyl)pentanamide (MK-944A), interferons such as α-interferon, renal excretion inhibitors such as probenecid, nucleoside transport inhibitors such as dipyridamole; pentoxifylline, N-acetylcysteine (NAC), Procysteine, α-trichosanthin, phosphonoformic acid, as well as immunomodulators such as interleukin II or thymosin, granulocyte macrophage colony stimulating factors, erythropoetin, soluble $CD_4$ and genetically engineered derivatives thereof, non-nucleoside reverse transcriptase inhibitors (NNRTIs), for example nevirapine (BI-RG-587), alpha-((2-acetyl-5-methylphenyl)amino)-2,6-dichloro-benzeneacetamide (loviride), 1-[3-(isopropylamino)-2-pyridyl]-4-[5-(methanesulfonamido)-1H-indol-2-ylcarbonyl]piperazine monomethanesulfonate (delavirdine), (10R, 11S, 12S)-12-Hydroxy-6,6,10,11-tetramethyl-4-propyl-11,12-dihydro-2H,6H,10H-benzo(1,2-b:3, 4-b':5,6-b")tripyran-2-one ((+) calanolide A), (4S)-6-Chloro-4-[1E)-cyclopropylethenyl)-3,4-dihydro-4-(trifluoromethyl)-2(1H)-quinazolinone (DPC-083), (S)-6-chloro-4-(cyclopropylethynyl)-1,4-dihydro-4-(trifluoromethyl)-2H-3,1-benzoxazin-2-one (efavirenz, DMP 266), 1-(ethoxymethyl)5-(1-methylethyl)-6-(phenylmethyl)-2,4(1H,3H)-pyrimidinedione (MKC-442), and 5-(3, 5-dichlorophenyl)thio-4-isopropyl-1-(4-pyridyl)methyl-1H-imidazol-2-ylmethyl carbamate (capravirine), glycoprotein 120 antagonists, for example PRO-2000, PRO-542 and 1,4-bis[3-[(2,4-dichlorophenyl)carbonylamino]-2-oxo-5,8-disodiumsulfanyl]naphthalyl-2,5-dimethoxyphenyl-1,4-dihydrazone (FP-21399), cytokine antagonists, for example reticulose (Product-R), 1,1'-azobis-formamide (ADA), 1,11-(1,4-phenylenebis(methylene))bis-1,4,8,11-tetraazacyclotetradecane octahydrochloride (AMD-3100), integrase inhibitors, or fusion inhibitors, for example T-20 and T-1249.

The present invention further includes the use of a compound according to the invention in the manufacture of a medicament for simultaneous or sequential administration with at least another therapeutic agent, such as those defined herein before.

Compounds of the present invention may be administered with an agent known to inhibit or reduce the metabolism of compounds, for example ritonavir. Accordingly, the present invention features a method for the treatment or prophylaxis of a disease as hereinbefore described by administration of a compound of the present invention in combination with a metabolic inhibitor. Such combination may be administered simultaneously or sequentially.

In general a suitable dose for each of the above-mentioned conditions will be in the range of 0.01 to 250 mg, per kilogram body weight of the recipient (e.g. a human) per day, suitably in the range of 0.1 to 100 mg per kilogram body weight per day and most suitably in the range 0.5 to 30 mg per kilogram body weight per day and particularly in the range 1.0 to 20 mg per kilogram body weight per day. Unless otherwise indicated, all weights of active ingredient are calculated as the parent compound of formula (I); for salts or esters thereof, the weights would be increased proportionally. The desired dose may be presented as one, two, three, four, five, six or more sub-doses administered at appropriate intervals throughout the day. In some cases the desired dose may be given on alternative days. These sub-doses may be administered in unit dosage forms, for example, containing 10 to 1000 mg or 50 to 500 mg, suitably 20 to 500 mg, and most suitably 50 to 400 mg of active ingredient per unit dosage form.

While it is possible for the active ingredient to be administered alone it is preferable to present it as a pharmaceutical composition. The compositions of the present invention comprise at least one active ingredient, as defined above, together with one or more acceptable carriers thereof and optionally other therapeutic agents. Each carrier must be acceptable in the sense of being compatible with the other ingredients of the composition and not injurious to the patient.

Phamaceutical compositions include those suitable for oral, rectal, nasal, topical (including transdermal, buccal and sublingual), vaginal or parenteral (including subcutaneous, intramuscular, intravenous, intradermal, and intravitreal) administration. The compositions may conveniently be presented in unit dosage form and may be prepared by any methods well known in the art of pharmacy. Such methods represent a further feature of the present invention and include the step of bringing into association the active ingredients with the carrier, which constitutes one or more accessory ingredients. In general, the compositions are prepared by uniformly and intimately bringing into association the active ingredients with liquid carriers or finely divided solid carriers or both, and then if necessary shaping the product.

The present invention further includes a pharmaceutical composition as hereinbefore defined wherein a compound of the present invention or a pharmaceutically acceptable derivative thereof and another therapeutic agent are presented separately from one another as a kit of parts.

Compositions suitable for transdermal administration may be presented as discrete patches adapted to remain in intimate contact with the epidermis of the recipient for a prolonged period of time. Such patches suitably contain the active compound 1) in an optionally buffered, aqueous solution or 2) dissolved and/or dispersed in an adhesive or 3) dispersed in a polymer. A suitable concentration of the active compound is about 1% to 25%, suitably about 3% to 15%. As one particular possibility, the active compound may be delivered from the patch by electrotransport or lontophoresis as generally described in Pharmaceutical Research 3 (6), 318 (1986).

Pharmaceutical compositions of the present invention suitable for oral administration may be presented as discrete units such as capsules, caplets, cachets or tablets each containing a predetermined amount of the active ingredients; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredients in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Molded tablets may be made by molding a mixture of the powdered compound moistened with an inert liquid diluent in a suitable machine. The tablets may optionally be coated or scored and may be formulated so as to provide slow or controlled release of the active ingredients therein using, for example, hydroxypropylmethyl cellulose in varying proportions to provide the desired release profile. Tablets may optionally be provided with an enteric coating, to provide release in parts of the gut other than the stomach.

Pharmaceutical compositions suitable for topical administration in the mouth include lozenges comprising the active ingredients in a flavored base, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions suitable for vaginal administration may be presented as pessaries, tampons, creams, gels, pastes, foams or spray Pharmaceutical compositions containing in addition to the active ingredient such carriers as are known in the art to be appropriate.

Pharmaceutical compositions for rectal administration may be presented as a suppository with a suitable carrier comprising, for example, cocoa butter or a salicylate or other materials commonly used in the art. The suppositories may be conveniently formed by admixture of the active combination with the softened or melted carrier(s) followed by chilling and shaping in molds.

Pharmaceutical compositions suitable for parenteral administration include aqueous and nonaqueous isotonic sterile injection solutions which may contain anti-oxidants, buffers, bacteriostats and solutes which render the pharmaceutical composition isotonic with the blood of the intended recipient; and aqueous and non-aqueous sterile suspensions which may include suspending agents and thickening agents; and liposomes or other microparticulate systems which are designed to target the compound to blood components or one or more organs. The pharmaceutical compositions may be presented in unit-dose or multi-dose sealed containers, for example, ampoules and vials, and may be stored in a freeze-dried (lyophilized) condition requiring only the addition of the sterile liquid carrier, for example water for injection, immediately prior to use. Extemporaneous injection solutions and suspensions may be prepared from sterile powders, granules and tablets of the kind previously described.

Unit dosage pharmaceutical compositions include those containing a daily dose or daily subdose of the active ingredients, as hereinbefore recited, or an appropriate fraction thereof.

It should be understood that in addition to the ingredients particularly mentioned above the pharmaceutical compositions of this invention may include other agents conventional in the art having regard to the type of pharmaceutical composition in question, for example, those suitable for oral administration may include such further agents as sweeteners, thickeners and flavoring agents.

EXAMPLES

The following examples are intended for illustration only and are not intended to limit the scope of the invention in any way.

Low resolution, open-access LCMS data were acquired in either ESI pos/neg or APCI pos/neg mode with scanning from 100-1100 amu @ 0.5 sec/scan. LC conditions: flowrate 0.8 mL/min. 85% H2O (0.1% formic acid) to 100% MeOH (0.075% formic acid) in 6 minutes. Phenomenex Max-RP column, 2.0×50 mm.

High Resolution Mass Spectra were acquired using Micromass LCT mass spectrometer (time-of-flight) with flow injection (FIA-MS) at 0.3 mL/min with 100% MeOH (0.1% formic acid), run time of 2 minutes, in ESI+mode, scanning from 100-1100 amu @ 0.5 sec/scan. Reserpine was used as the lock mass (m/z 609.2812) and to adjust mass scale.

As will be appreciated by those skilled in the art, the following schemes may be followed in preparing the compounds of the present invention. Any variability depicted within the scheme(s) illustrated herein should be limited to the particular scheme and not necessarily extended throughout the rest of the present specification.

Abbreviations used:
LHMDS=lithium hexamethyl disilazide
THP=tetrahydropyran
NMO=N-methylmorpholine N-oxide I. B-Ring is Pyrroildine
  C3-Linker Pyrrolidine

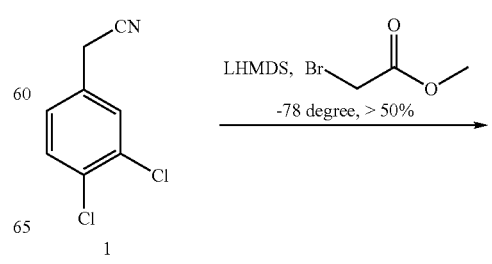

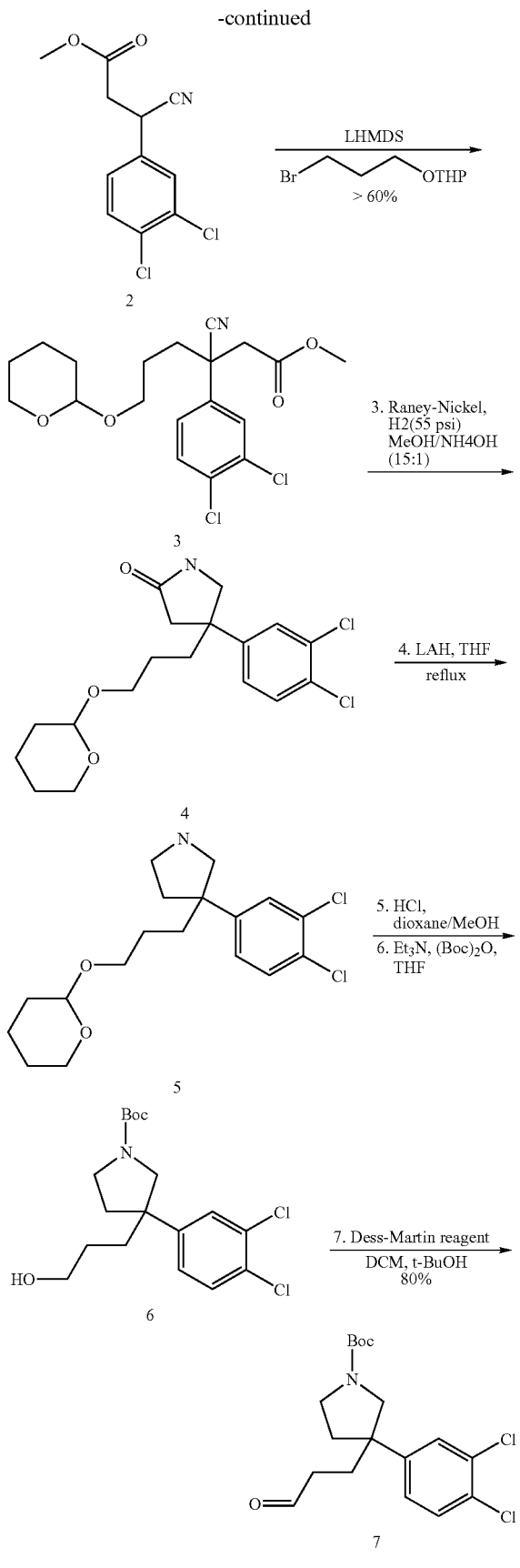

I.1. Intermediate Compound 1 (3,4dichlorophenyl)acetonitrile (50.85 g, 273.38 mmol) was dissolved in THF (200 mL). The solution was cooled down to −78° C., LHMDS (1 M in THF, 287 mL) was added via cannula. The content was stirred at −78° C. for 30 min, then it was transferred to a solution of methyl bromoacetate (40.77 mL, 430.58 mmol) at r.t. The reaction was completed in less than four hours. The solvent was then removed under reduced pressure. The residue was dissolved in ethyl acetate. The organic layer was washed with 1:1 brine:H20, dried, filtrated and concentrated. FCC with hexane:ethyl acetate (5:1) afford 20 g desired intermediate product 2.

I.2. Intermediate Compound 2 (8.2 g, 31.9 mmol) was dissolved in THF (200 mL) and cooled to −78° C. LHMDS (1 M in THF, 33.5 mmol) was added and the content stirred at −78° C. for 10 min before being transferred to a solution of 2-(3-bromopropoxy)-tetrahydro-2H-pyran (6.48 mL, 38.29 mmol) at r.t via cannula. The reaction was completed in 4 hrs and solvents were removed under reduced pressure, residue redissolved in ethyl acetate and washed with 1:1 brine:$H_2O$, dried, filtrated and concentrated. FCC with hexane:EtOAc (5:1 to 4:1) afford 7.4 g of the intermediate product 3 as light yellow oil.

I.3. Intermediate Compound 3 was dissolved in MeOH (60 mL), followed by concentrated ammonium hydroxide (4 mL) and Raney-Nickel. The contents were hydrogenated (55 Psi) in the Parr apparatus overnight. The desired intermediate product 4 was secured after filtration and solvent removal.

I.4. Intermediate Compound 4 (3.35 g, 13.48 mmol) was dissolved in THF (50 mL), followed by LAH (13.5 mL, 1 M in ether). The mixture was refluxed under nitrogen for 1 h, and then cooled to 0° C. with ice bath followed by a carefully quench with water. The suspension was filtered through a plug of celite and concentrated to give colorless oil intermediate product 5.

I.5. Intermediate Crude product 5 was dissolved in methanol (15 mL), followed by HCl in dioxane (30 mL, 4M), and the mixture stirred at rt for 1 hr, during which it turned pink. The mixture was then concentrated under reduced pressure, redissolved in THF (40 mL), and added triethylamine (10 mL) and (Boc)2O in THF (14 mL, 1 M). After stirring at rt for 1.5 hrs, saturated sodium bicarbonate solution was added and the product extracted with ethyl acetate. The organic layer was then dried over sodium sulfate, solvents removed and the product purified on flash column chromatography with hexane:ethyl acetate (1:1), affording 2.64 g of oily intermediate product 6.

I.6. Synthesis of Intermediate compound 7: Dissolve Dess-Martin periodinane (4.77 g, 11.25 mmo) in dichloromethane (60 mL), followed by t-BuOH (1.07 mL), stir at r.t for 5 min and dropwise add product compound 6 (2.63 g, 7.03 mmol) in dichloromethane (10 mL). After stirring at rt for 30 min, the mixture was diluted with ethyl ether and washed with 1.3 N NaOH. The organic layer was then dried over sodium sulfate, the solvent was removed after filtration and crude product purified on flash column chromatography with hexane: ethyl acetate (3:1) affording 1.88 g product 7 as colorless oil.

The following are representative analytical data for compounds of the present invention:

I. Intermediate Compound 2 methyl 3-cyano-3-(3,4dichlorophenyl)propanoate $^1$HNMR (400 MHz, CDCl$_3$) δ[ppm]: 7.22 (1H, d, J=8.2 Hz), 4.25 (1H, t, J=7.3 Hz), 3.71 (3H, s), 3.01 (1H, dd, J=16.8 Hz, 7.5 Hz), 2.82 (1H, dd, J=16.8 Hz, 7.1 Hz). $^{13}$CNMR (400 MHz, CDCl$_3$) δ[ppm]: 169.35, 134.61, 133.39, 131.47, 129.71, 126.97, 52.75, 39.60, 32.49. Elemental Analysis calculated for C$_{11}$H$_9$Cl$_2$NO$_2$ C, 51.19%; H, 3.51%; N, 5.43%. found C, 51.02%; H, 3.93%; N, 4.25%.

I. Intermediate Compound 3 methyl 3-cyano-3-(3,4-dichlorophenyl)-6-(tetrahydro-2H-pyran-2-yloxy)hexanoate $^1$HNMR (400 MHz, CDCl$_3$) δ[ppm]: 7.47 (1H, d, J=2.3 Hz), 7.38 (1H, d, J=8.4 Hz), 7.24 (1H, dd, J=8.6 Hz, 2.4 Hz), 4.40 (1H, dt, J=17.6 Hz, 3.7 Hz), 3.75-3.58 (2H, m), 3.52 (3H, s), 3.41-3.34 (1H, m), 3.30-3.24 (1H, m), 2.98 (1H, d, J=16.5 Hz), 2.88 (1H, d, J=16.4 Hz), 2.15-2.04 (1H, m), 2.00-1.90 (1H, m), 1.73-1.54 (3H, m), 1.47-1.28 (5H, m). $^{13}$CNMR (400 MHz, CDCl$_3$) δ[ppm]: 168.67, 138.08, 133.43, 132.65, 131.06, 128.30, 125.74, 120.70, 99.18, 99.09, 66.44, 66.32, 62.74, 62.64, 52.26, 44.35, 44.29, 37.52, 30.86, 25.68, 25.60, 19.90, 19.85. HRMS calculated for C$_{19}$H$_{23}$Cl$_2$NO$_4$ Na (M+Na)$^+$ 422.0922. found 422.0890.

I. Intermediate Compound 7

1,1-dimethylethyl 3-(3,4-dichlorophenyl)-3-(3-oxopropyl)-1-pyrrolidinecarboxylate $^1$HNMR (400 MHz, CDCl$_3$) δ[ppm]: 9.49 (1H, s), 7.29 (1H, d, J=8.3 Hz), 7.17 (1H, s), 6.94 (1H, d, J=8.4 Hz), 3.53-3.42 (2H, m), 3.36-3.18 (2H, m), 2.12-1.92 (5H, m), 1.88-1.78 (1H, m). $^{13}$CNMR (400 MHz, CDCl$_3$) δ[ppm]: 200.84, 154.70, 154.56, 144.49, 132.91, 131.04, 130.77, 128.79, 126.20, 79.88, 79.73, 55.71, 54.86, 48.89, 48.05, 44.47, 44.17, 39.97, 36.61, 35.23, 31.36, 28.67.

II. C2-Linker Pyrrolidine:

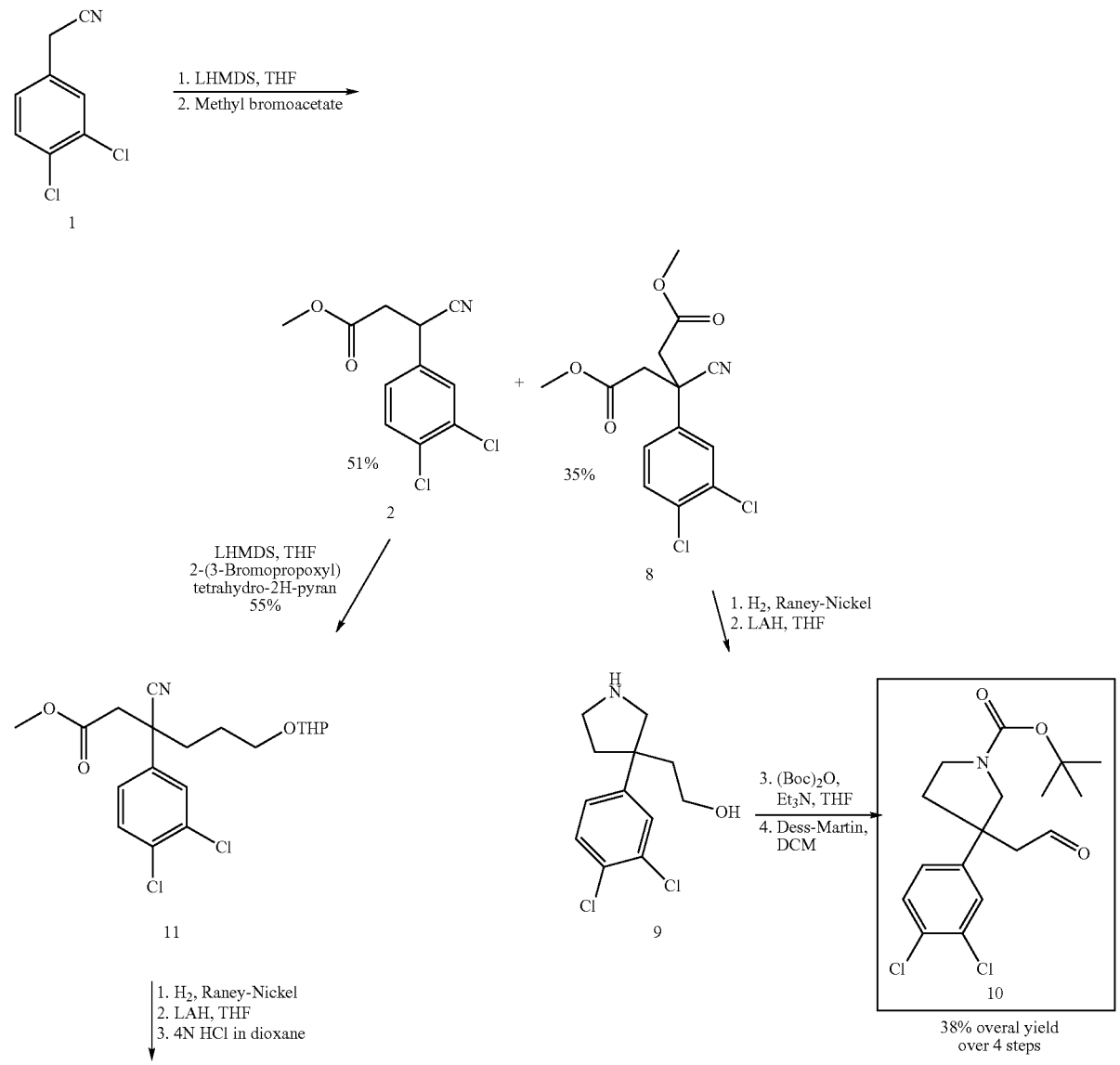

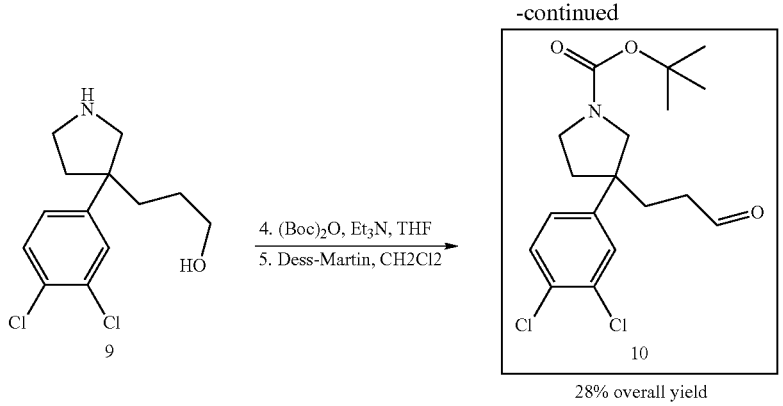

28% overall yield

The synthesis of the C2-pyrrolidine scaffold was carried out by two procedures. Alkylation of 1 with methyl bromoacetate resulted in a separable mixture of monoalkylated 2 and bis-alkylated 8, each of which was subjected to the desired 10 by a separate route.

Compound 2 was converted to 10 in five steps and in 28% overall yield, while the conversion of 8 to 10 could be accomplished in 4 steps and in a higher overall yield of 38%.

The following are representative analytical data for compounds of the present invention:

II. Intermediate Compound 8 dimethyl 3-cyano-3-(3,4-dichlorophenyl)pentanedioate $^1$HNMR (400 MHz, CDCl$_3$) δ[ppm]: 7.54 (1H, d, J=2.4 Hz), 7.43 (1H, d, J=8.6 Hz), 7.31 (1H, dd, J=8.4 Hz, 2.4 Hz), 3.60 (6H, s), 3.22 (2H, d, J=16.6 Hz), 3.04 (2H, d, J=16.7 Hz). $^{13}$CNMR(400 MHz, CDCl$_3$) δ[ppm]: 168.56, 137.38, 133.24, 131.12, 128.15, 125.48, 120.08. HRMS calculated for C$_{14}$H$_{13}$Cl$_2$NO$_4$Na (M+Na)$^+$ 352.019. found 352.0123.

II. Intermediate Compound 10

1,1-dimethylethyl 3-(3,4-dichlorophenyl)-3-(3-oxopropyl)-1-pyrrolidinecarboxylate $^1$HNMR (400 MHz, CDCl$_3$) δ[ppm]: 9.39 (1H, s), 7.30-7.25 (2H, m), 7.02 (1H, d, J=8.5 Hz), 3.62-3.51 (2H, m), 3.38-3.23 (2H, m), 2.82-2.62 (2H, m), 2.20-2.01 (2H, m), 1.36 (9H, d, J=9.2 Hz). $^{13}$CNMR(400 MHz, CDCl$_3$) δ[ppm]: 199.95, 154.56, 143.96, 132.95, 131.28, 130.80, 128.72, 126.14, 80.06, 79.91, 55.77, 55.66, 52.07, 47.16, 46.38, 44.22, 43.87, 36.35, 35.98, 28.67.

The following representative examples, Examples 1-13 of the invention were synthesized according to the following representative synthetic scheme III:

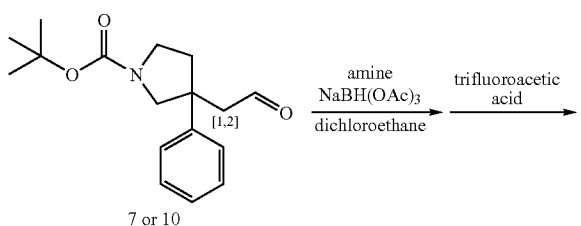

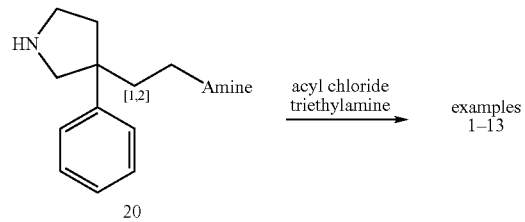

EXAMPLE 1 tert-butyl 3-(3,4-dichlorophenyl)-3-[3-(4-oxo-1-phenyl-1,3,8-triazaspiro[4.5]dec-8-yl)propyl]pyrrolidine-1-carboxylate

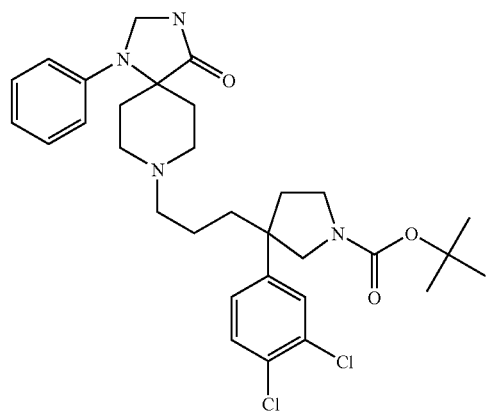

$^1$H NMR (300 MHz, CDCl$_3$) δ 7.42-7.40(m,1H), 7.31(m, 2H), 7.24-7.07(m,2H), 6.94-6.87(m,2H), 6.30(m,1H), 3.57-3.32(m,3H), 2.71-2.57(m,2H), 2.32(m,1H), 2.13-2.07(m, 2H), 1.83-1.70(m,4H), 1.52-1.49(m,7H), 1.29(s,9H), 0.91-0.86(m,4H).

mass spectrometry ES+=587/589 (M+1, 2 Cl isotope pattern)

EXAMPLE 2

8-{3-[3-(3,4-dichlorophenyl)-1-(2-furoyl)pyrrolidin-3-yl]propyl}-1-phenyl-1,3,8-triazaspiro[4.5]decan-4-one

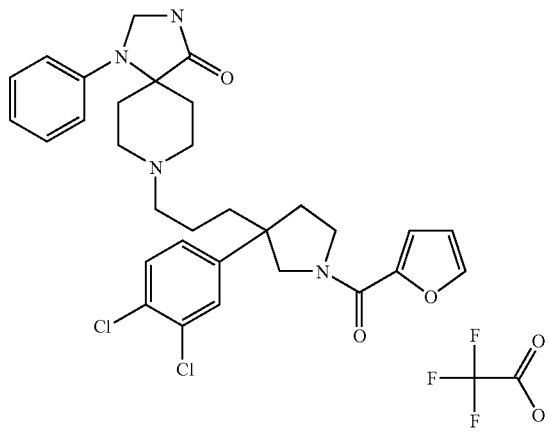

$^1$H NMR (500 MHz, DMSO-D$_6$) δ 8.99(s,1H), 7.89(m, 1H), 7.63(m,2H), 7.45-7.01(m,4H), 6.89(m,2H), 6.80(m, 1H), 6.70-6.60(m1H), 4.60(s,2H), 4.09(m,1), 3.97-3.68(m, 4H), 3.65-3.44(m,4H), 3.02(m,2H), 2.70(m,2H), 2.36-2.00 (m,2H), 1.90-1.62(m,3H), 1.44-1.29(m,2H). mass spectrometry ES+=581/583 (M+1, 2 Cl isotope pattern)

EXAMPLE 3

8-{3-[3-(3,4-dichlorophenyl)-1-(isoxazol-5-ylcarbonyl)pyrrolidin-3-yl]propyl}-1-phenyl-1,3,8-triazaspiro[4.5]decan-4-one

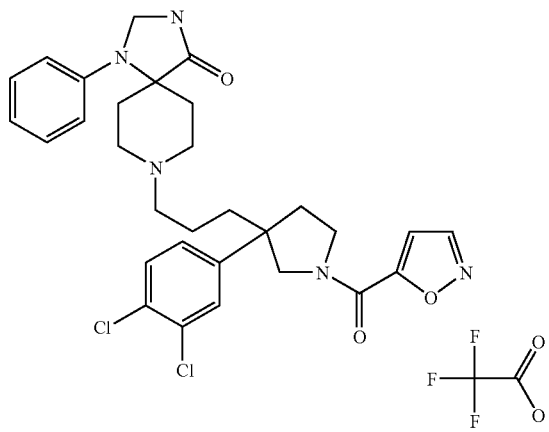

$^1$H NMR (500 MHz, DMSO-D$_6$) δ 8.97(s,1H), 8.75(m, 1H), 7.63(m,2H), 7.35-7.20(m,2H), 7.12-7.06(m,2H), 6.89 (m,2H), 6.80(m,1H), 4.59(s,2H), 4.05(m, 1H), 3.97-3.45(m, 8H), 3.01(m,2H), 2.67(m,2H), 2.36-2.18(m,2H), 1.86-1.68 (m,3H), 1.42-1.24(m,2H). mass spectrometry ES+=582/584 (M+1, 2 Cl isotope pattern)

EXAMPLE 4

8-{3-[3-(3,4-dichlorophenyl)-1-(1H-pyrrol-2-ylcarbonyl)pyrrolidin-3-yl]propyl}-1-phenyl-1,3,8-triazaspiro[4.5]decan-4-one

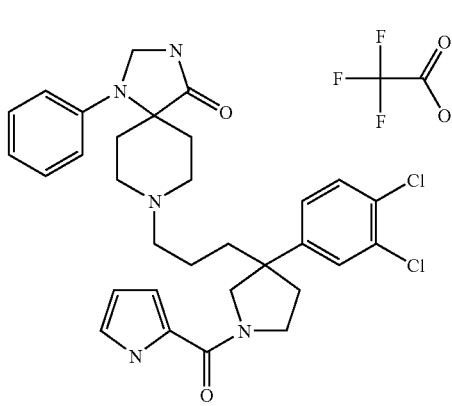

$^1$H NMR (400 MHz, DMSO-D$_6$) δ 11.45(m,1H), 8.96(s, 1H), 7.59(m,2H), 7.32-7.11(m,3H), 6.85-6.56(m,5H), 6.10 (m,1H), 4.56(s,2H), 4.01-3.40(m,9H), 2.96(m,2H), 2.66(m, 2H), 2.31-2.12(m,2H), 1.81-1.56(m,3H), 1.50-1.21(m,2H). mass spectrometry ES+=580/582 (M+1, 2 Cl isotope pattern)

EXAMPLE 5

8-{3-[3-(3,4-dichlorophenyl)-1-pentanoylpyrrolidin-3-yl]propyl}-1-[3-(trifluoromethyl)phenyl]-1,3,8-triazaspiro[4.5]decan-4-one

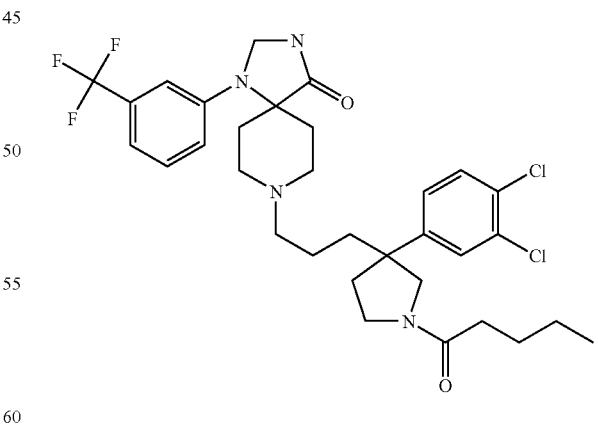

$^1$H NMR (400 MHz, CDCl$_3$) δ 7.79(m,1H), 7.36-7.01(m, 6H), 6.95-6.88(m,1H), 4.74(s,2H), 3.87-3.78(m,1H), 3.70-3.48(m,3H), 3.41-3.34(m,1H), 2.76(m,3H), 2.36-2.05(m, 6H), 1.81(m,1H), 1.68-1.53(m,5H), 1.42-1.11(m,5H), 0.94-0.83(m,4). mass spectrometry ES+=638/640 (M+1, 2 Cl isotope pattern)

EXAMPLE 6

8-{3-[3-(3,4-dichlorophenyl)-1-(2-furoyl)pyrrolidin-3-yl]propyl}-1-[3-(trifluoromethyl)phenyl]-1,3,8-triazaspiro[4.5.]decan-4-one

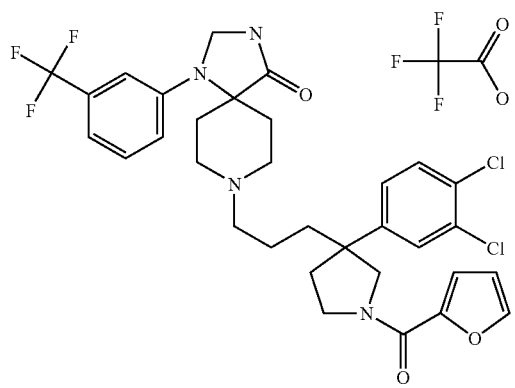

¹H NMR (400 MHz, CDCl₃) δ 7.54(m,1H), 7.47(s,1H), 7.41-7.25(m,4H), 7.18-7.02(m,4H), 6.46(m,1H), 4.73(s, 2H), 4.10-3.74(m,4H), 2.79-2.52(m,3H) 2.38-2.12(m,3H), 1.81-1.57(m,3H), 1.32-1.10(m,3H), 0.85-0.68(m,4H). mass spectrometry ES+=649/651 (M+1, 2 Cl isotope pattern)

EXAMPLE 7

8-{3-[1-(cyclobutylcarbonyl)-3-(3,4-dichlorophenyl)pyrroidin-3-yl]propyl}-1-[3-(trifluoromethyl)phenyl]-1,3,8-triazaspiro[4.5]decan-4-one

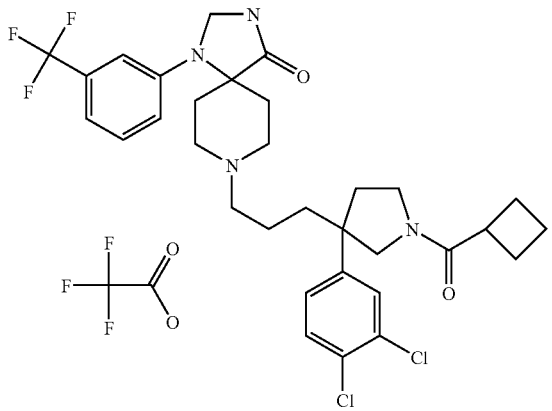

¹H NMR (500 MHz, DMSO-D₆) δ 9.63-9.51(m,1H), 7.62-7.37(m,4H), 7.31-7.22(m,2H), 7.07(s,1H), 5.04(s,2H), 3.94-3.83(m,2H), 3.65(m,1H), 3.60(s,1H), 3.48-3.20(m, 2H), 3.01(m,2H), 2.31-2.02(m,10H), 1.93-1.50(m,6H), 1.41-1.18(m,2H). mass spectrometry ES+=637/639 (M+1, 2 Cl isotope pattern)

EXAMPLE 8

8-{3-[3-(3,4-dichlorophenyl)-1-pentanoylpyrrolidin-3-yl]propyl}-1-phenyl-1,3,8-triazaspiro[4.5]decan-4-one

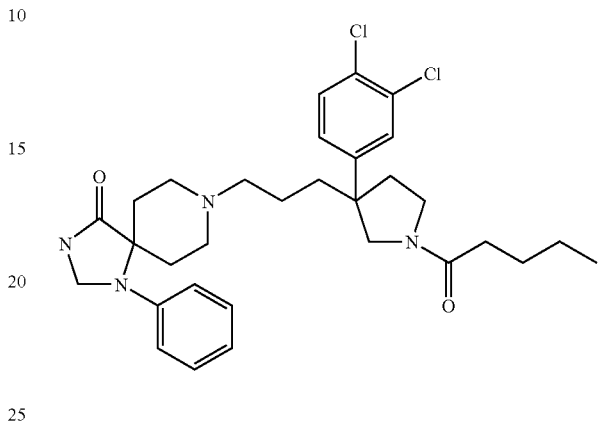

¹H NMR (300 MHz, CDCl₃) δ 7.50-7.27(m,4H), 7.14-7.04(m,1H), 6.97-6.86(m,2H), 6.81-6.67(m,1H), 4.75(s, 2H), 3.83-3.55(m,3H), 3.44(m,1H), 3.10-2.65(m,7H), 2.56-2.42(m,2H), 2.38-2.06(m,4H), 1.88-1.57(m,4H), 1.48-1.27 (m,4H), 1.04-1.87(m,3H). mass spectrometry ES+=571/573 (M+1, 2 Cl isotope pattern)

EXAMPLE 9

8-{3-[1-(cyclopentylcarbonyl)-3-(3,4-dichlorophenyl)pyrrolidin-3-yl]propyl}-1-phenyl-1,3,8-triazaspiro[4.5]decan-4-one

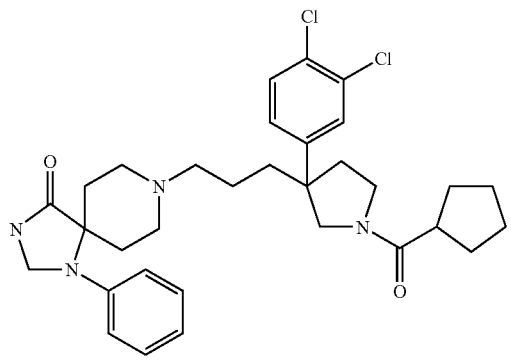

¹H NMR (300 MHz, CDCl₃) δ 7.69-7.67(m1H), 7.51-7.49(m,1H), 7.34(m,1H), 7.31-7.18(m,3H), 7.05-6.79(m, 2H), 4.69(s,1H), 4.19(m,3H), 3.76-3.64(m,1H), 3.51(m,1H), 3.28-3.12(m,1H), 2.65(m,1H), 2.32-2.09(m,4H), 1.72-1.61 (m,5H), 1.45-1.19(m,7H0, 0.94-0.78(m,8H). mass spectrometry ES+=583/585 (M+1, 2 Cl isotope pattern)

EXAMPLE 10

8-{3-[1-(cyclobutylcarbonyl)-3-(3,4-dichlorophenyl)pyrrolidin-3-yl]propyl}-1-phenyl-1,3,8-triazaspiro[4.5]decan-4-one

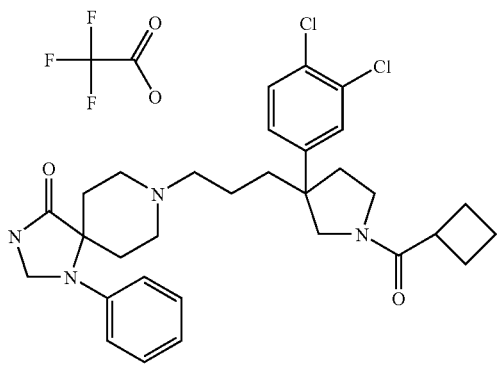

¹H NMR (300 MHz, CDCl₃) δ 7.38-7.18(m,4H), 7.04(m, 1H), 6.90-6.85(m,2H), 6.35(m,1H), 4.69(s,1H), 3.78-3.44 (m,4H), 2.78-2.63(m,5H), 2.40-2.30(m,1H), 2.17-2.06(m, 2H), 1.91-1.50(m,14H), 1.27-1.21(m,2H). mass spectrometry ES+=569/571 (M+1, 2 Cl isotope pattern)

EXAMPLE 11

8-{3-[1-(cyclobutylcarbonyl)-3-(3,4-dichlorophenyl)pyrrolidin-3-yl]propyl}-1-(3-methylphenyl)-1,3,8-triazaspiro[4.5]decan-4-one

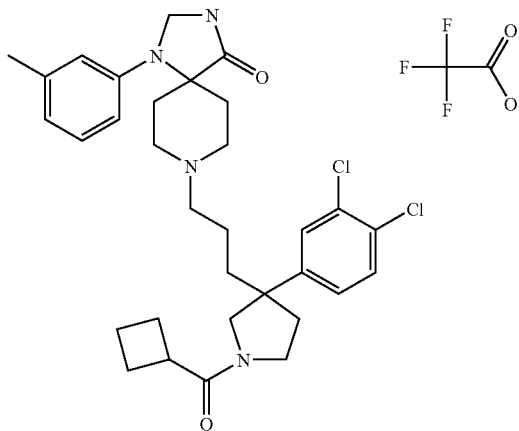

¹H NMR (500 MHz, DMSO-D₆) δ 8.96(s,1H), 7.67-7.49 (m,2H), 7.31-7.26(m,1H), 7.08(m,1H), 6.77(m,1H), 6.62(m, 2H), 4.58(s,2H), 3.67-3.22(m,10H), 2.98(m,2H), 2.66(m, 2H), 2.25(s,3H), 2.16-2.04(m,5H), 1.94-1.79(m,3H), 1.74-1.52(m,3H), 1.42-1.22(m,2H). mass spectrometry ES+=583/585 (M+1, 2 Cl isotope pattern)

EXAMPLE 12

3-acetyl-8-{3-[1-acetyl-3-(3,4-dichlorophenyl)pyrrolidin-3-yl]propyl}-1-(3-methylphenyl)-1,3,8-triazaspiro[4.5]decan-4-one

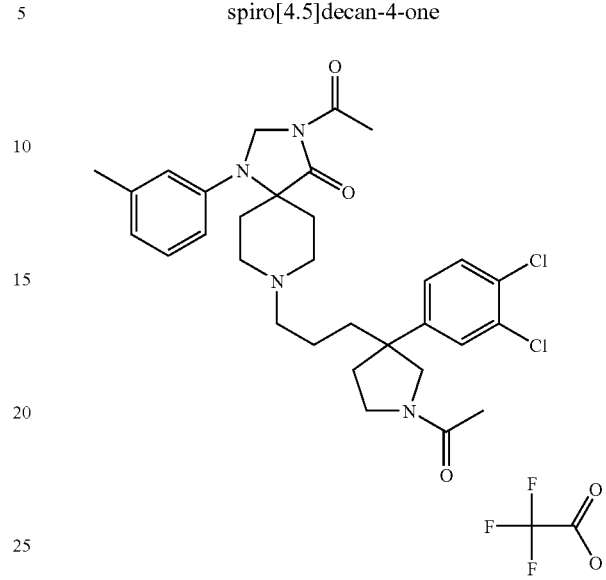

¹H NMR (500 MHz, DMSO-D₆) δ 7.61-7.49(m,2H), 7.30(m,1H), 7.15(m,1H), 6.89(m,1H), 6.77(m,2H), 4.93(s, 3H), 3.79(m,1H), 3.61-3.34(m,7H), 2.99(m,2H), 2.46(s,4H), 23.1-1.86(m,10H), 1.75-1.59(m,2H), 1.41-1.30(m,2H). mass spectrometry ES+=543/545 (M+1, 2 Cl isotope pattern)

EXAMPLE 13

Compound 13 was synthesized by reacting amine 20 with chlorobenzoxazole.

8-{3-[1-(1,3-benzoxazol-2-yl)-3-(3,4-dichlorophenyl)pyrrolidin-3-yl]propyl}-1-phenyl-1,3,8-triazaspiro[4.5]decan-4-one

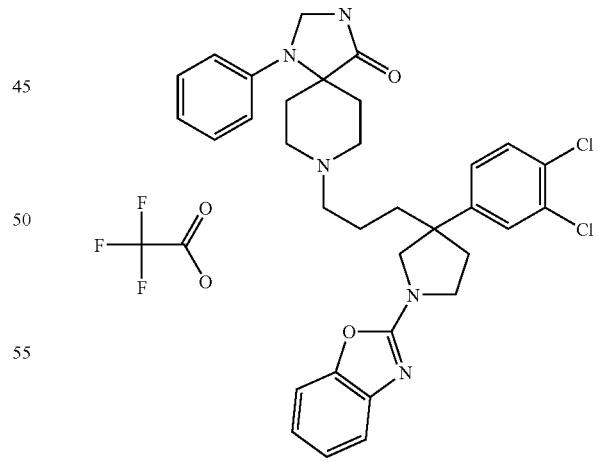

¹H NMR (400 MHz, DMSO-D₆) δ 8.96(s,1H), 7.58(m, 2H), 7.37-7.29(m,2H), 7.26-7.07(m,4H), 6.96(m,1H), 6.85 (m,2H), 6.75(m,1H), 4.56(s,2H), 3.94-3.88(m,1H), 3.80(m, 1H), 3.67(m,1H), 3.55-3.42(m,6H), 2.96(m,2H), 2.66(m, 2H), 2.35-224(m,2H), 1.82-1.67(m,3H), 1.48-1.34(m,2H). mass spectrometry ES+=604/606 (M+1, 2 Cl isotope pattern)

Additional compounds of the present invention include oxygen linked compounds as illustrated hereinbelow.

IV. O-Linker Pyrrolidine

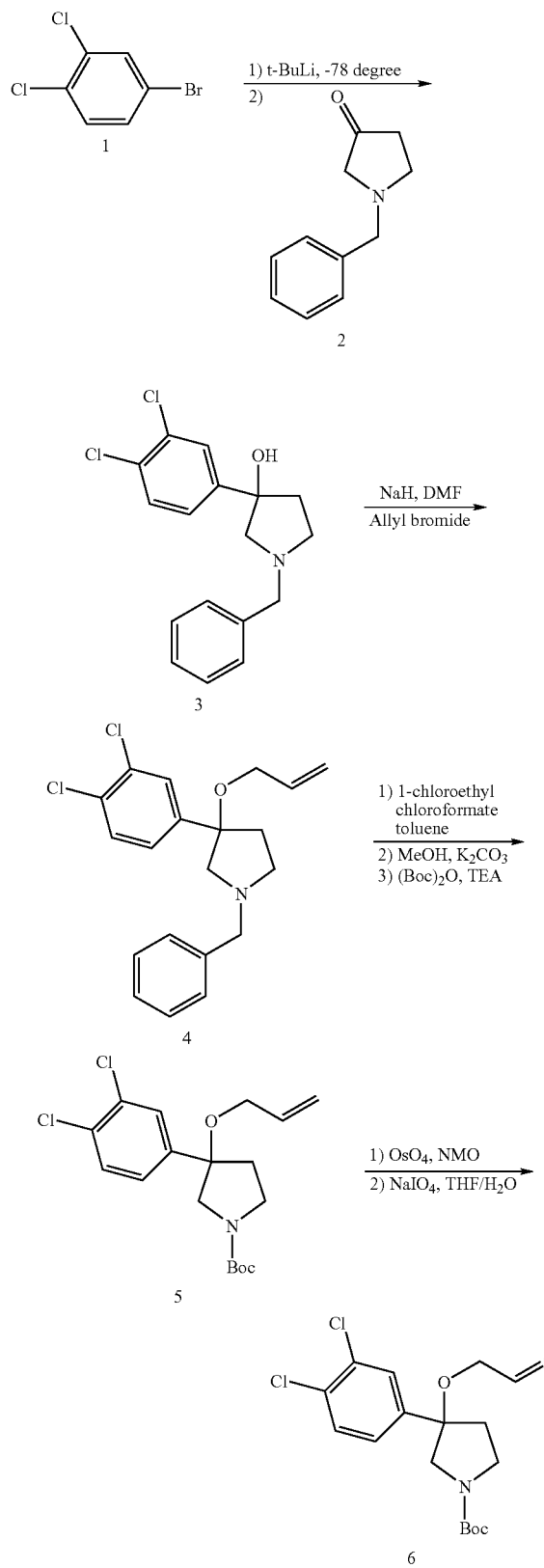

The following are representative analytical data for compounds of the present invention:

IV. Intermediate Compound 3

3-(3,4-dichlorophenyl)-1-(phenylmethyl)-3-pyrrolidinol $^1$HNMR (400 MHz, CDCl$_3$) δ[ppm]: 7.63 (1H, d, J=2.0 Hz), 7.40-7.26 (7H, m), 3.72 (2H, s), 3.42-3.30 (1H, m), 3.15-3.08 (1H, m), 2.64 (1H, d, J=10.2 Hz), 2.60-2.53 (2H, m), 2.32-2.25 (1H, m), 2.22-2.14 (1H, m). $^{13}$CNMR (400 MHz, CDCl$_3$) δ[ppm]: 145.19, 138.65, 132.53, 131.12, 130.34, 129.04, 128.68, 127.85, 127.54, 125.02, 80.21, 68.85, 60.01, 52.85, 42.44.

IV. Intermediate Compound 4

3-(3,4-dichlorophenyl)-1-(phenylmethyl)-3-(2-propen-1-yloxy)pyrrolidine $^1$HNMR (400 MHz, CDCl$_3$) δ[ppm]: 7.54 (1H, d, J=2.0 Hz), 7.40-7.24 (7H, m), 5.82-5.82 (1H, m), 5.28 (1H, dd, J=17.2 Hz, 1.6 Hz), 5.14 (1H, dd, J=10.5 Hz, 1.1 Hz), 3.71-3.67 (4H, m), 3.01-2.77 (4H, m), 2.36-2.30 (1H, m), 2.18-2.13 (1H, m). $^{13}$CNMR (400 MHz, CDCl$_3$) δ[ppm]: 135.05, 132.71, 131.20, 130.55, 128.92, 128.63, 128.52, 127.41, 125.76, 116.55, 86.06, 65.63, 64.88, 60.78, 53.50, 39.05.

IV. Intermediate Compound 5

3-(3,4-dichlorophenyl)-3-(2-propen-1-yloxy)pyrrolidine

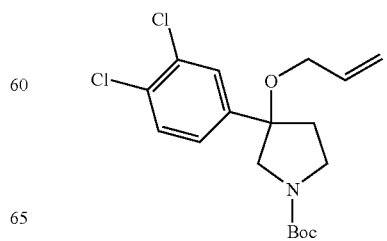

$^1$HNMR (400 MHz, CDCl$_3$) δ[ppm]: 7.47 (1H, d, J=2.0 Hz), 7.42 (1H, d, J=8.4 Hz), 7.23 (1H, dd, J=8.4 Hz, 2.0 Hz), 5.88-5.78 (1H, m), 5.24 (1H, dd, J=9.3 Hz, 1.5 Hz), 3.68-3.60 (3H, m), 3.40 (1H, d, J=12.0 Hz), 3.337-3.27 (1H, m), 3.20-3.13 (1H, m), 2.95 (1H, d, J=12.1 Hz), 2.36-2.29 (1H, m), 2.15-2.06 (1H, m). $^{13}$CNMR (400 MHz, CDCl$_3$) δ[ppm]: 141.61, 134.85, 133.03, 132.09, 130.80, 128.95, 126.28, 116.77, 87.39, 65.16, 57.59, 45.87, 36.21.

Additionally Intermediate Compound 5 may be protected with an appropriate protecting group, as will be appreciated by those skilled in the art: 1,1-dimethylethyl 3-(3,4-dichlorophenyl)-3-(2-propen-1-yloxy)-1-pyrrolidinecarboxylate ¹HNMR (400 MHz, CDCl₃) δ[ppm]: 7.47-7.7.42 (2H, m), 7.24-7.21 (1H, m), 5.85-5.75 (1H, m), 5.23 (1H, d, J=17.2 Hz), 5.12 (1H, dd, J=10.3 Hz, 3.7 Hz), 3.88-3.42 (6H, m), 2.40-2.34 91H, m), 2.17-2.08 (1H, m), 1.46 (9H, s).

IV. Intermediate Compound 6

1,1-dimethylethyl 3-(3,4-dichlorophenyl)-3-[(2-oxo-ethyl)oxy]-1-pyrrolidinecarboxylate ¹HNMR (400 MHz, CDCl₃) δ[ppm]: 9.59 (1H, d, J=7.7 Hz), 7.47-7.45 (2H, m), 7.23-7.21 (1H, m), 3.94-3.72 (3H, m), 3.62-3.48 (3H, m), 2.41-2.38 (1H, m), 2.23-2.18 (1H, m), 1.47 (9H, s).

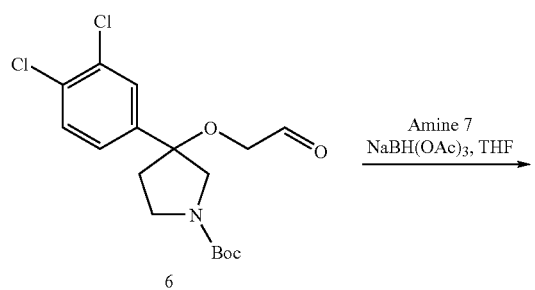

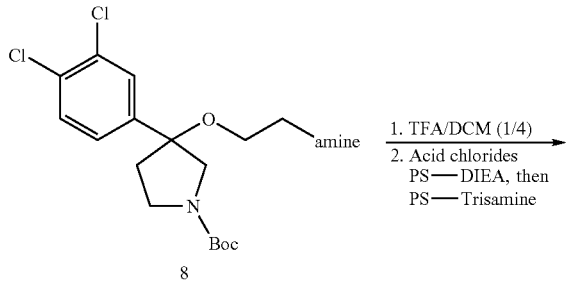

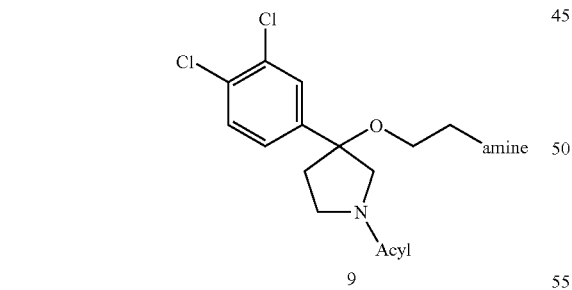

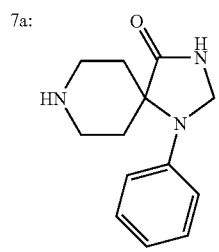

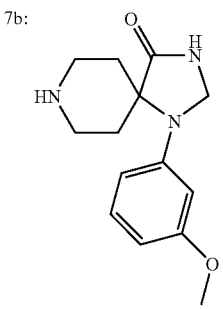

Acid Chlorides:

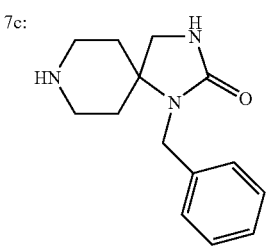

IV. Intermediate Compound 8a 1,1-dimethylethyl 3-(3,4-dichlorophenyl)-3-{[2-(4-oxo-1-phenyl-1,3,8-triazaspiro[4.5]dec-8-yl)ethyl]oxy}-1-pyrrolidinecarboxylate

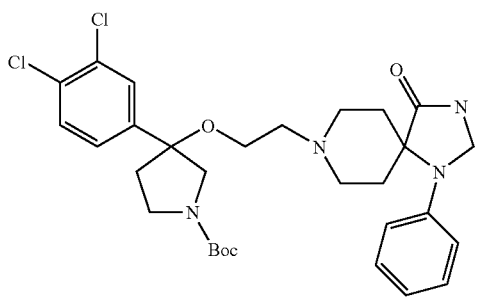

¹HNMR (400 MHz, CDCl₃) δ[ppm]: 7.54 (1H, d, J=7.9 Hz), 7.47 (1H, d, J=1.8 Hz), 7.42 (1H, d, J=8.5 Hz), 7.28

(2H, d, J=7.6 Hz), 6.90-6.83 (3H, m), 4.72 (2H, s), 3.82 (1H, dd, J=40.4 Hz, 11.6 Hz), 3.56 (2H, d, J=8.5 Hz), 3.50-3.42 (1H, m), 3.30-3.20 (2H, m), 2.81-2.58 (8H, m), 2.40-2.37 (1H, m), 2.16-2.05 (1H, m), 1.68 (2H, d, J=13.1 Hz), 1.46 (9H, s). HRMS calculated for $C_{30}H_{39}Cl_2N_4O_4$ (M+H)$^+$ 589.2348. found 589.2360.

IV. Intermediate Compound 8b 1,1-dimethylethyl 3-(3,4-dichlorophenyl)-3-[(2-{1-[3-(methyloxy)phenyl]-4-oxo-1,3,8-triazaspiro[4.5]dec-8-yl}ethyl)oxy]-1-pyrrolidinecarboxylate

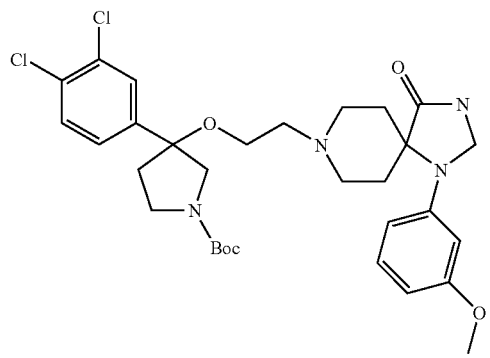

$^1$HNMR (400 MHz, CDCl$_3$) δ[ppm]: 7.97 (1H, s), 7.45-7.41 (2H, m), 7.29-7.25 (1H, m), 7.16 (1H, t, J=8.1 Hz), 6.55 (1H, d, J=7.8 Hz), 6.40-6.36 (2H, m), 4.69 (2H, s), 3.87-3.76 (4H, m), 3.56-3.41 (3H, m), 3.32-3.19 (2H, m), 2.80-2.57 (8H, m), 2.40-2.37 (1H, m), 2.16-2.05 (1H, m), 1.64 (2H, d, J=12.8 Hz), 1.45 (9H, s). HRMS calculated for $C_{31}H_{41}Cl_2N_4O_5$ (M+H)$^+$ 619.2454. found 619.2437.

IV. Intermediate Compound 8c 1,1-dimethylethyl 3-(3,4-dichlorophenyl)-3-({2-[2-oxo-1-(phenylmethyl)-1,3,8-triazaspiro[4.5]dec-8-yl]ethyl}oxy)-1-pyrrolidinecarboxylate

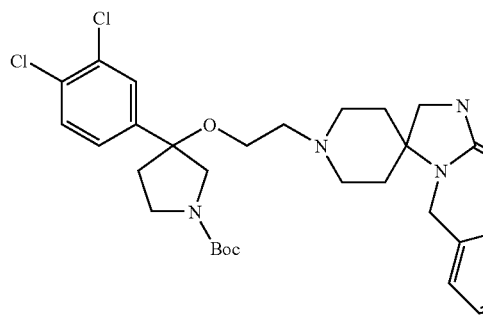

$^1$HNMR (400 MHz, CDCl$_3$) δ[ppm]: 7.41-7.15 (8H, m), 4.31 (2H, s), 3.75 (1H, dd, J=42.5 Hz, 11.5 Hz), 3.50-3.35 (3H, m), 3.25-3.04 (4H, m), 2.67 (2H, broad s), 2.39-2.28 (3H, m), 2.08-2.00 (1H, m), 1.93-1.73 (4H, m), 1.47 (9H, s). LRMS calculated for $C_{31}H_{41}Cl_2N_4O_4$ (M+H)$^+$ 603. found 603.

Additionally, as will be appreciated, the synthesis of O-piperidine analogues may be provided through a parallel synthesis.

EXAMPLE 14

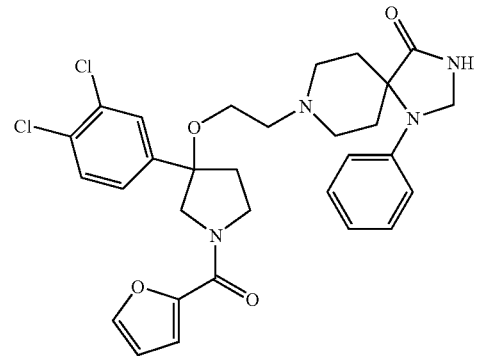

Molecular Weight = 583.51
Exact Mass = 582
Molecular Formula = C30H32Cl2N4O4

8-(2-{[3-(3,4-dichlorophenyl)-1-(2-furoyl)pyrrolidin-3-yl]oxy}ethyl)-1-phenyl-1,3,8-triazaspiro[4.5]decan-4-one $^1$HNMR (400 MHz, CDCl$_3$) δ[ppm]: 7.71-7.64 (2H, m), 7.56 (1H, d, J=8.4 Hz), 7.48-7.44 (1H, m), 7.23 (2H, t, J=7.7 Hz), 7.16 (1H, d, J=3.5 Hz), 6.98 (2H, d, J=8.9 Hz), 6.84 (1H, t, J=7.3 Hz), 4.65 (2H, d, J=3.6 Hz), 4.36 (1H, dd, J=67.1 Hz, 11.9 Hz), 4.14-4.10 (1H, m), 3.85-3.79 (1H, m), 3.83 (1H, dd, J=119.5 Hz, 11.9 Hz), 3.43-3.37 (1H, m), 3.28-3.18 (1H, m), 2.92-2.65 (4H, m), 2.63-2.50 (4H, m), 2.45-2.38 (1H, m), 1.67-1.57 (2H, m). HRMS calculated for $C_{30}H_{33}Cl_2N_4O_4$ (M+H)$^+$ 583.1879. found 583.1865.

EXAMPLE 15

8-(2-{[1-(cyclopentylcarbonyl)-3-(3,4-dichlorophenyl)pyrrolidin-3-yl]oxy}ethyl)-1-phenyl-1,3,8-triazaspiro[4.5]decan-4-one

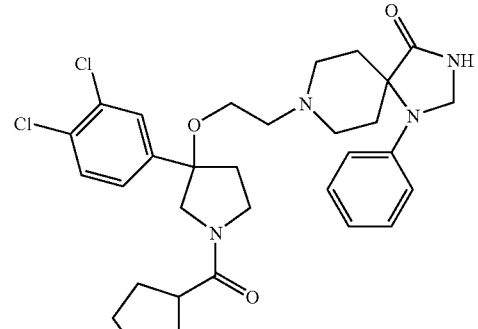

Molecular Weight = 585.57
Exact Mass = 584
Molecular Formula = C31H38Cl2N4O3

$^1$HNMR (400 MHz, CDCl$_3$) δ[ppm]: 7.65 (1H, dd, J=16.8 Hz, 2.0 Hz), 7.55 (1H, dd, J=8.3 Hz, 2.0 Hz), 7.45-7.40 (1H, m), 7.24 (2H, t, J=7.7 Hz), 7.00 (2H, d, J=8.5 Hz), 6.84 (1H, t, J=7.3 Hz), 4.66 (2H, s), 4.08 (1H, dd, J=12.6 Hz, 1.7 Hz), 3.82-3.78 (1H, m), 3.70-3.66 (1H, m), 3.60-3.36 (3H, m), 3.27-3.18 (1H, m), 2.96-2.87 (3H, m), 2.80-2.72 (2H, m), 2.62-2.52 (5H, m), 2.38-2.22 (1H, m), 1.92-1.82 (2H, m), 1.77-1.56 (8H, m). HRMS calculated for $C_{31}H_{39}Cl_2N_4O_3$ $(M+H)^+$ 585.2399. found 585.2384.

EXAMPLE 16

8-(2-{[1-acetyl-3-(3,4-dichlorophenyl)pyrrolidin-3-yl]oxy}ethyl)-1-phenyl-1,3,8-triazaspiro[4.5]decan-4-one

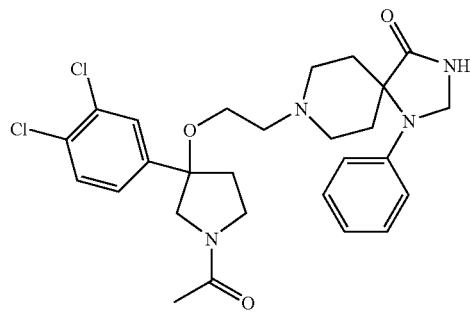

Molecular Weight = 531.48
Exact Mass = 530
Molecular Formula = C27H32Cl2N4O3

$^1$HNMR (400 MHz, CDCl$_3$) δ[ppm]: 7.65 (1H, dd, J=12.8 Hz, 2.2 Hz), 7.55 (1H, dd, J=8.4 Hz, 2.7 Hz), 7.42 (1H, td, J=8.9 Hz, 2.0 Hz), 7.24 (2H, td, J=9.3 Hz, 2.3 Hz), 6.99 (2H, d, J=8.2 Hz), 6.84 (1H, t, J=7.3 Hz), 4.66 (2H, s), 4.07 (1H, t, J=11.2 Hz), 3.79-3.66 (2H, m), 3.58-3.35 (2H, m), 3.26-3.19 (1H, m), 2.95-2.83 (2H, m), 2.79-2.70 (2H, m), 2.63-2.52 (5H, m), 2.38-2.22 (1H, m), 2.07 (2H, d, J=3.6 Hz), 1.66 (2H, d, J=13.7 Hz). HRMS calculated for $C_{27}H_{33}Cl_2N_4O_3$ $(M+H)^+$ 531.1929. found 531.1920.

EXAMPLE 17

8-(2-{[3-(3,4-dichlorophenyl)-1-(phenylsulfonyl)pyrrolidin-3-yl]oxy}ethyl)-1-phenyl-1,3,8-triazaspiro[4.5]decan-4-one

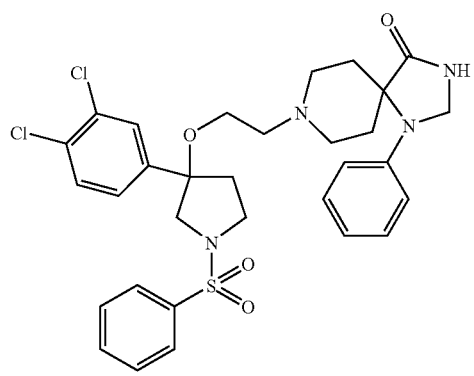

Molecular Weight = 629.61
Exact Mass = 628
Molecular Formula = C31H34Cl2N4O4S $^1$HNMR (400 MHz, CDCl$_3$) δ[ppm]: 7.87 (2H, d, J=7.3 Hz), 7.66 (1H, t, J=7.2 Hz), 7.58 (2H, 7.8 Hz), 7.51 (1H, d, J=1.8 Hz), 7.47 (1H, d, J=8.4 Hz), 7.29 (1H, dd, J=8.4 Hz, 2.0 Hz), 7.23 (2H, t, J=8.2 Hz), 6.96 (2H, d, J=8.2 Hz), 6.83 (1H, t, J=7.3 Hz), 4.66 (2H, s), 3.79 (1H, dd, J=11.3 Hz, 1.1 Hz), 3.57 (1H, t, J=7.5 Hz), 3.46 (1H, d, J=11.4 Hz), 3.42-3.38 (1H, m), 3.12-3.09 (1H, m), 2.94-2.90 (1H, m), 2.80-2.70 (2H, m), 2.61-2.40 (5H, m), 2.22-2.13 (3H, m), 1.61 (2H, d, J=11.4 Hz).

EXAMPLE 18

8-(2-{[3-(3,4-dichlorophenyl)-1-(2-furoyl)pyrrolidin-3-yl]oxy}ethyl)-1-(3-methoxyphenyl)-1,3,8-triazaspiro[4.5]decan-4-one

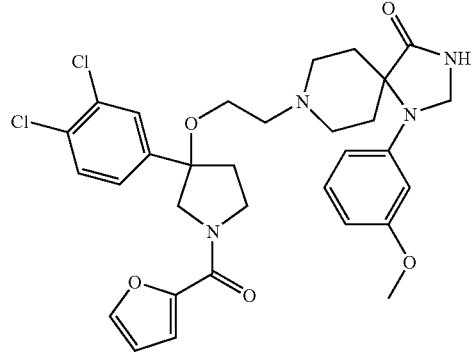

Molecular Weight = 613.54
Exact Mass = 612
Molecular Formula = C31H34Cl2N4O5

$^1$HNMR (400 MHz, CDCl$_3$) δ[ppm]: 7.70-7.63 (2H, m), 7.56 (1H, d, J=8.3 Hz), 7.49-7.45 (1H, m), 7.16-7.12 (2H, m), 6.65-6.61 (1H, m), 6.59-6.55 (1H, m), 6.44 (2H, d, J=6.2 Hz), 4.63 (2H, d, J=3.3 Hz), 4.35 (1H, dd, J=67.0 Hz, 11.9 Hz), 4.25-4.20 (1H, m), 3.85-3.79 (1H, m), 3.82 (1H, dd, J=109.8 Hz, 12.0 Hz), 3.75 (3H, s), 3.42-3.39 (1H, m), 3.30-3.18 (1H, m), 2.90-2.65 (5H, m), 2.64-2.52 (4H, m), 2.45-2.39 (1H, m), 1.65-1.55 (2H, m). HRMS calculated for $C_{31}H_{35}Cl_2N_4O_5$ $(M+H)^+$ 613.1985. found 613.1987.

EXAMPLE 19

8-(2-{[1-(cyclopentylcarbonyl)-3-(3,4-dichlorophenyl)pyrrolidin-3-yl]oxy}ethyl)-1-(3-methoxyphenyl)-1,3,8-triazaspiro[4.5]decan-4-one

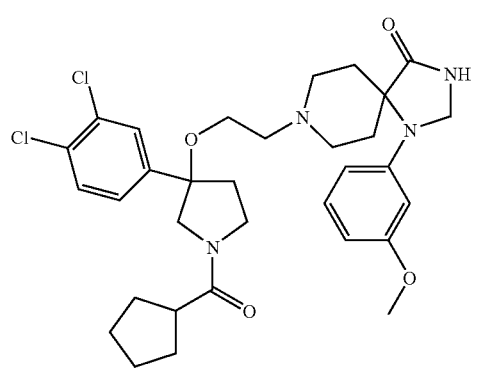

Molecular Weight = 615.60
Exact Mass = 614
Molecular Formula = C32H40Cl2N4O4

$^1$HNMR (400 MHz, CDCl$_3$) δ[ppm]: 7.64 (1H, dd, J=17.0 Hz, 2.0 Hz), 7.55 (1H, dd, J=8.4 Hz, 5.3 Hz), 7.43 (1H, ddd, J=8.4 Hz, 7.2 Hz, 2.0 Hz), 7.15 (1H, t, J=8.4 Hz), 6.65-6.62 (1H, m), 6.45-6.43 (2H, m), 4.64 (2H, s), 4.11 (1H, q, J=11.3 Hz), 3.83-3.79 (1H, m), 3.75 (3H, s), 3.70-3.65 (1H, m), 3.58-3.52 (1H, m), 3.47 (1H, d, J=12.6 Hz), 3.41-3.35 (1H, m), 3.27-3.19 (1H, m), 2.98-2.84 (3H, m), 2.78-2.70 (2H, m), 2.64-2.52 (4H, m), 2.38-2.21 (1H, m), 1.92-1.80 (2H, m), 1.75-1.55 (8H, m). HRMS calculated for $C_{32}H_{41}Cl_2N_4O_4$ (M+H)$^+$ 615.2505. found 615.2496.

EXAMPLE 20

8-(2-{[1-acetyl-3-(3,4-dichlorophenyl)pyrolidin-3-yl]oxy}ethyl)-1-(3-methoxyphenyl)-1,3,8-triazaspiro[4.5]decan-4-one

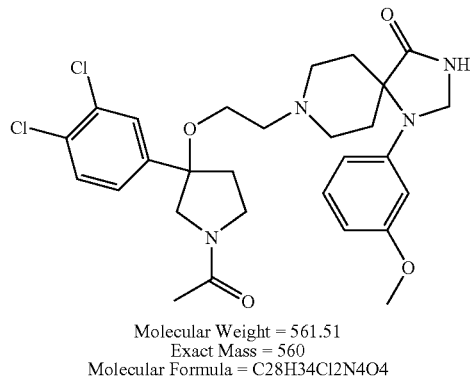

Molecular Weight = 561.51
Exact Mass = 560
Molecular Formula = C28H34Cl2N4O4

$^1$HNMR (400 MHz, CDCl$_3$) δ[ppm]: 7.65 (1H, dd, J=12.6 Hz, 2.0 Hz), 7.55 (1H, dd, J=8.4 Hz, 3.1 Hz), 7.43 (1H, td, J=9.3 Hz, 2.0 Hz), 7.15 (1H, td, J=8.6 Hz, 3.1 Hz), 6.66-6.63 (1H, m), 6.45-6.43 (2H, m), 4.64 (2H, s), 4.06 (1H, t, J=12.7 Hz), 3.75 (3H, s), 3.72 (2H, t, J=4.2 Hz), 3.57-3.50 (1H, m), 3.45 (1H, d, J=12.6), 3.41-3.35 (1H, m), 3.26-3.19 (1H, m), 2.93-2.83 (2H, m), 2.78-2.69 (2H, m), 2.64-2.52 (4H, m), 2.39-2.22 (1H, m), 2.07 (3H, d, J=2.7 Hz), 1.64 (2H, d, J=13.5 Hz). HRMS calculated for $C_{28}H_{35}Cl_2N_4O_4$ (M+H)$^+$ 561.2035. found 561.2051.

EXAMPLE 21

8-(2-{[3-(3,4dichlorophenyl)-1-(phenylsulfonyl)pyrrolidin-3-yl]oxy}ethyl)-1-(3-methoxyphenyl-1,3,8-triazaspiro[4.5]decan-4-one

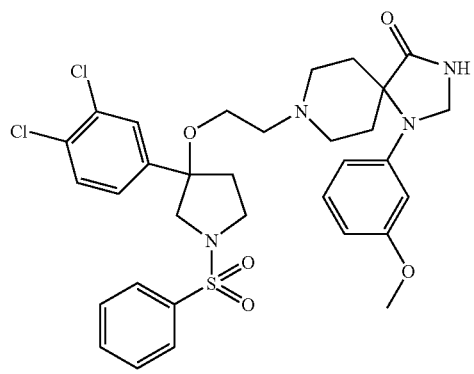

Molecular Weight = 659.63
Exact Mass = 658
Molecular Formula = C32H36Cl2N4O5S $^1$HNMR (400 MHz, CDCl$_3$) δ[ppm]: 7.88 (2H, d, J=7.5 Hz), 7.68-7.64 (1H, m), 7.61-7.57 (2H, m), 7.52 (1H, d, J=2.0 Hz), 7.48 (1H, d, J=8.2 Hz), 7.31 (1H, dd, J=8.3 Hz, 2.0 Hz), 7.15 (1H, t, J=8.8 Hz), 6.62 (1H, dd, J=7.4 Hz, 2.0 Hz), 6.45-6.44 (2H, m), 4.65 (2H, s), 3.81-3.76 (4H, m), 3.57 (1H, broad t, J=3.7 Hz), 3.48-3.38 (2H, m), 3.13-3.07 (1H, m), 2.98-2.85 (2H, m), 2.78-2.71 (2H, m), 2.60-2.49 (4H, m), 2.45-2.39 (1H, m), 2.24-2.14 (3H, m), 1.63-1.58 (2H, m). HRMS calculated for $C_{32}H_{37}Cl_2N_4O_5S$ (M+H)$^+$ 659.1862. found 659.1845.

V. B-Ring is Azetidine

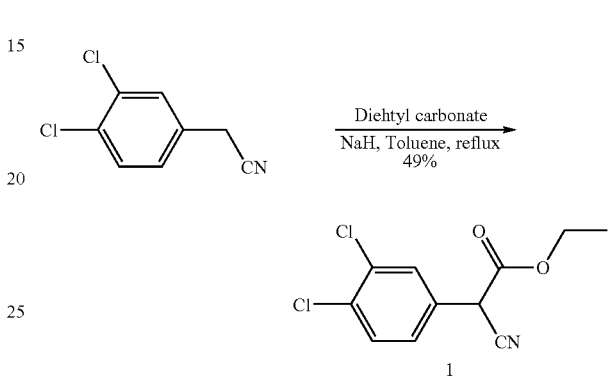

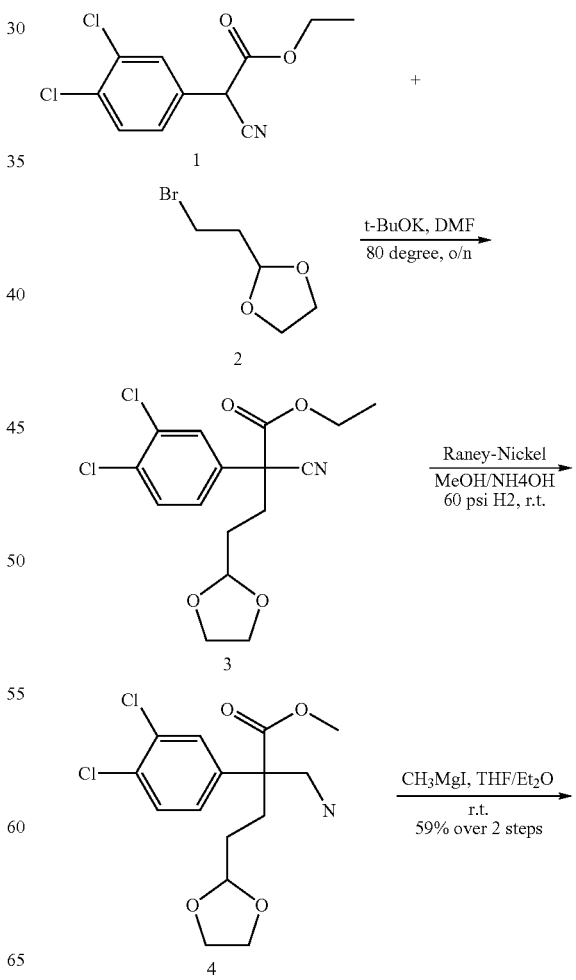

97

-continued

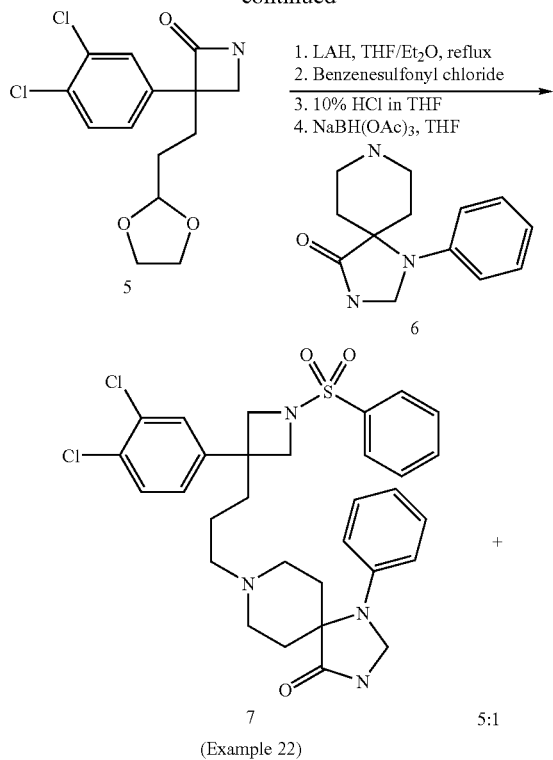

(Example 22)

Synthesis of Intermediate 1 ethyl cyano(3,4-dichlorophenyl)acetate

To a solution of diethyl carbonate (4.1 mL, 33.88 mmol) in toluene (150 mL) at r.t, sodium hydride (1.43 g, 60% in mineral oil, 35.75 mmol) and 3,4-dichlorophenyl acetonitrile (6.34 g, 34.09 mmol) were added. The content was stirred at 80° C. overnight. After cooling to r.t, HCl was added (1 N in $H_2O$, 100 mL). The content was extracted with ethyl acetate (3×). The combined organic layer was washed with water, dried ($Na_2SO_4$), filtered and concentrated. The residue was purified by flash column chromatography with hexane/ethyl acetate (6/1) to give 7.42 g product (85% yield) as brown oil. $^1$H NMR (400 MHz, $CDCl_3$) δ[ppm]: 7.60 (1H, broad s), 7.54 (1H, d, J=8.3 Hz), 7.35 (1H, broad d, J=8.3 Hz), 4.72 (1H, s), 4.29 (2H, q, J=14.2 Hz, 7.0 Hz), 1.28 (3H, t, J=6.7 Hz). LRMS calculated for $C_{11}H_9Cl_2NO_2$ $M^+$ 257. found 257.

98

Synthesis of Intermediate 3 ethyl 2-cyano-2-(3,4-dichlorophenyl)-4-(1,3-dioxolan-2-yl)butanoate

To a solution of 1 (7.02 g, 27.32 mmol) and 2-(2-bromoethyl)-1,3-dioxolane compound 2 (3.85 mL, 32.78 mmol) in anhydrous DMF (100 mL), potassium t-butoxide (32.78 mL, 1 M in t-BuOH) was added. The content was heated to 80° C. and stirred overnight. $H_2O$ (400 mL) and brine (200 mL) were added to the content and the mixture was extracted with ethyl acetate. The combined organic layer was dried over sodium sulfate, filtered and concentrated. Flash column chromatography with hexane/ethyl acetate (6/1) afforded 9.5 g brown oil (~85% product+~15% SM). $^1$H NMR (400 MHz, $CDCl_3$) δ[ppm]: 7.66 (1H, d, J=2.3 Hz), 7.48 (1H, d, J=8.4 Hz), 7.40 (1H, dd, J=8.4 Hz, 2.2 Hz), 4.91 (1H, t, J=4.4 Hz), 4.30-4.20 (2H, m), 3.98-3.94 (2H, m), 3.86-3.83 (2H, m), 2.48 (1H, td, J=12.2 Hz, 4.5 Hz), 2.24 (1H, td, J=12.2 Hz, 4.3 Hz), 1.88-1.81 (1H, m), 1.75-1.68 (1H, m), 1.24 (3H, t, J=7.1 Hz). $^{13}$C NMR (400 MHz, $CDCl_3$) δ[ppm]: 166.90, 134.68, 133.70, 131.28, 128.60, 125.88, 117.58, 103.04, 65.26, 63.91, 53.22, 32.24, 29.88, 14.06.

Synthesis of Intermediate 5

3-(3,4-dichlorophenyl)-3-[2-(1,3-dioxolan-2-yl)ethyl]-2-azetidinone

To a solution of 3 (1.50 g, 4.20 mmol) in EtOH (100 mL), Raney-Nickel (1 g) was added. The content was stirred at 60 psi H2 overnight. It was then filtered through celite and concentrated. The residue was dissolved in Et2O (20 mL), $CH_3MgI$ (5.6 mL, 3M in $Et_2O$, 16.8 mmol) was added. The content was stirred at r.t ovenight. The reaction was quenched with saturated sodium bicarbonate solution, filtered through celite, extracted with EtOAc, dried and then concentrated. The residue was purified with flash column chromatography with hexane/EtOAc (1/2) to give 0.78 g product (59% yield over two steps) as light yellow solid. $^1$H NMR (400 MHz, $CDCl_3$) δ[ppm]: 7.49 (1H, d, J=2.1 Hz), 7.40 (1H, d, J=8.3 Hz), 7.25 (1H, dd, J=8.2 Hz, 1.9 Hz), 6.23 (1H, s), 4.82 (1H, t, J=4.5 Hz), 3.93-3.88 (2H, m), 3.83-3.78 (2H, m), 3.50 (2H, dd, J=15.9 Hz, 5.5 Hz), 2.10-2.02 (2H, m), 1.81-1.72 (1H, m), 1.61-1.52 (1H, m). $^{13}$C NMR (400 MHz, $CDCl_3$) δ[ppm]: 171.44, 140.05, 132.82, 131.48, 130.74, 128.92, 126.42, 103.83, 65.17, 62.98, 48.63, 31.37, 29.36. LRMS calculated for $C_{14}H_{16}Cl_2NO_3$ $(M+H)^+$ 316. found 316.

Synthesis of Intermediate 7

EXAMPLE 22

8-{3-[3-(3,4-dichlorophenyl)-1-(phenylsulfonyl)-3-azetidinyl]propyl}-1-phenyl-1,3,8-triazaspiro[4.5]decan-4-one To a solution of 5 (0.778 g, 2.47 mmol) in THF (15 mL), LAH (4.94 mL, 1M in Et2OH, 4.94 mmol) was added at r.t. The content was heated to reflux for 5 hrs and then continued stirring ar r.t overnight. The reaction was cooled to 0° C. and quenched with $H_2O$ (0.23 mL), sodium hydroxide (15%, 0.23 mL) and $H_2O$ (0.69 mL) sequencially. Then it was filtered and concentrated to give a colorless oil.

Half of the oil was dissolved in dichloromethane. Triethylamine (0.518 mL, 3.72 mmol) was added, followed With benzenesulfonyl chloride (0.237 mL. 0.86 mmol). The content was shaked at r.t for 30 mins. The organic layer was washed with 1N sodium hydroxide, dried over sodium sulfate. Prep. TLC separation with hexane/EtOAc (1/1) afforded 100 mg product as colorless oil.

To a solution of the oil in THF (9 mL), concentrated HCl (1 mL) was added. The content was stirred at r.t overnight. It was quenched with saturated sodium bicarbonate solution, extracted with ethyl acetate. The organic layer was dried over sodium sulfate, filtered and concentrated to give a colorless oil.

To a solution of the oil in THF (5 mL), amine 6 (0.15 g, 0.65 mmol) was added. The content was stirred at r.t for 10 mins before NaBH(OAc)$_3$ (0.27 g, 1.30 mmol) was added. The content was shaken at r.t overnight. The reaction was quenched with saturated sodium bicarbonate and extracted with ethyl acetate. The organic layer was dried over sodium sulfate, filtered and concentrated resulting in the 5:1 mixture of 7 and 8. The residue was purified by PHPLC to remove the monochloro by-product and resulted in 31 mg of product 7 (Example 22) as white solid (formic acid salt). $^1$H NMR (400 MHz, CDCl$_3$) δ[ppm]: 8.41 (1H, s), 7.81 (2H, d, J=7.4 Hz), 7.61 (1H, t, J=7.3 Hz), 7.54 (2H, t, J=7.5 Hz), 7.33 (1H, d, J=8.3 Hz), 7.27 (2H, t, J=7.7 Hz), 6.98 (1H, d, J=2.2 Hz), 6.89-6.85 (3H, m), 6.78 (1H, dd, J=8.3 Hz, 2.2 Hz), 6.46 (1H, s), 4.73 (2H, s), 3.91 (2H, d, J=7.9 Hz), 3.84 (2H, d, J=7.9 Hz), 3.37-3.21 (4H, m), 2.99 (2H, td, J=14.3 Hz, 4.9 Hz), 2.73 (2H, t, J=7.7 Hz), 1.85-1.73 (4H, m), 1.48-1.40 (2H, m). LRMS calculated for $C_{31}H_{35}Cl_2N_4O_3S$ (M+H)$^+$ 613.2. found 613.3.

The following two compounds were made in a similar way. Except substituting 2-furancarbonyl chloride (23), cyclopentanecarbonyl chloride (24) for benzenesulfonyl chloride in the synthesis describe above for example 22.

(Example 23)

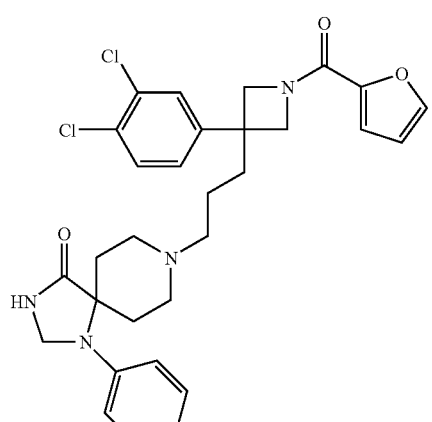

Molecular Weight = 567.51
Exact Mass = 566
Molecular Formula = C30H32Cl2N4O3

-continued (Example 24)

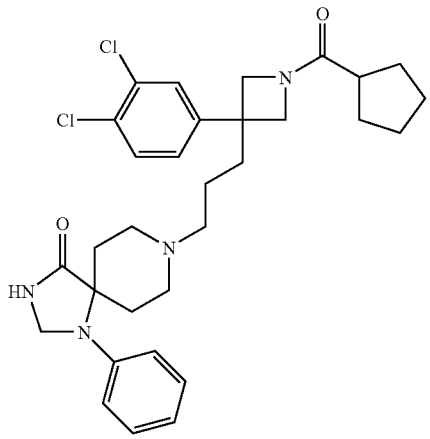

Molecular Weight = 569.57
Exact Mass = 568
Molecular Formula = C31H38Cl2N4O2

EXAMPLE 23

8-{3-[3-(3,4-dichlorophenyl)-1-(2-furanylcarbonyl)-3-azetidinyl]propyl}-1-phenyl-1,3,8-triazaspiro[4.5]decan-4-one $^1$H NMR (400 MHz, CDCl$_3$) δ[ppm]: 7.49 (1H, s), 7.43 (1H, d, J=8.2 Hz), 7.30-7.26 (4H, m), 7.08 (1H, d, J=3.3 Hz), 7.00 (1H, dd, J=8.2 Hz, 2.0 Hz), 6.94-6.85 (3H, m), 6.50-6.47 (1H, m), 4.76-4.68 (3H, m), 4.61-4.56 (1H, m), 4.36 (1H, d, J=9.9 Hz), 4.22 (1H, d, J=9.7 Hz), 2.82-2.52 (6H, broad), 2.46-2.30 (2H, broad s), 2.04-1.96 (2H, m), 1.70 (2H, d, J=12.8 Hz), 1.37 (2H, broad s). LRMS calculated for $C_{30}H_{33}Cl_2N_4O_3$ (M+H)$^+$ 567. found 567.

EXAMPLE 24

8-{3-[1-(cyclopentylcarbonyl)-3-(3,4-dichlorophenyl)-3-azetidinyl]propyl}-1-phenyl-1,3,8-triazaspiro[4.5]decan-4-one $^1$H NMR (400 MHz, CDCl$_3$) δ[ppm]: 7.44 (1H, d, J=8.2 Hz), 7.30-7.25 (3H, m), 7.20 (1H, d, J=2.2 Hz), 6.97 (1H, dd, J=8.4 Hz, 2.0 Hz), 6.92-6.85 (2H, m), 6.45 (1H, broad s), 4.71 (2H, s), 4.30 (1H, d, J=8.1 Hz), 4.24 (2H, d, J=11.4 Hz), 4.18 (1H, d, J=9.5 Hz), 2.70 (4H, broad s), 2.63-2.54 (2H, m), 1.95-1.90 (2H, broad), 1.80-1.67 (10H, m), 1.57-1.50 (2H, m), 1.37-1.20 (2H, broad). LRMS calculated for $C_{31}H_{39}Cl_2N_4O_3$ (M+H)$^+$ 569. found 569.

As will be appreciated by those skilled in the art, additional compounds of the present invention may be similarly prepared according to the schemes provided herein.

Biological Data

The following definitions apply:

| | |
|---|---|
| IC$_{50}$ | Concentration of compound that displaces 50% of radioligand |
| pIC$_{50}$ | The determined IC$_{50}$ value expressed as −log10(IC$_{50}$) |

CC-Chemokine Receptor-5 Binding by Scintillation Proximity Assay (CCR5 SPA)

Scintillation Proximity Assay for the Human CC-Chemokine Receptor, CCR-5

This protocol describes a high-throughput screen using SPA binding to identify compounds that inhibit binding of $^{125}$-MIP1α to the human CCR5 chemokine receptor.

CCR5 is a G protein-coupled receptor that binds the natural chemokine ligands, MIP1α, MIP1β and RANTES. CCR5 acts as a co-receptor with CD4 for entry of HIV-1 into human T-cells and monocytes. Chemokines also play a role in acute and chronic inflammatory processes. Chemokines are soluble proteins produced and released by a wide variety of cell types during the initial phase of a host response to a forgein substance entering the body.

Human CCR5 receptors were expressed in Chinese Hamster Ovary (CHO) cells, registration # 12025. Cells were grown in suspension and a 50 to 80 ml CCR5 cell pellet was prepared. Membrane preparation: 1) Weigh pellet; 2)Prepare an ice-cold 50 mM HEPES buffer, containing 0.0025 mg/ml Pefabloc, 0.0001 mg/ml Pepstatin A, 0.0001 mg/ml Leupeptin, 0.0001 mg/ml Aprotinin (protease inhibitor cocktail), pH 7.4; 3) Homogenize pellet in 5 volumes of HEPES buffer, 4) Homogenize again with a glass homogenizer 10 to 20 strokes; 5) Centrifuge homogenate at 18,000 rpm in a F28/36 rotor using a Sorvall RC26 PIUS refrigerated Centrifuge for 30 minutes; 6) Discard supernatant and resuspend pellet in 3 volumes of HEPES buffer; 7) Homogenize and centrifuge again using steps 4-6, 2 more times; 8) Reweigh pellet and homogenize in 3× weight-to-volume of HEPES buffer; 9) Aliquot 0.5 to 1.5 ml of the membrane preparation into small vials and store at −80 degrees Centigrade; 10) Determine the protein concentration of the membrane preparation using the Bio-Rad or BCA method; 11) The membrane homogenate will need to be characterized for the assay conditions a.) Protein concentration; b.) Optimal protein-to-bead ratio in SPA; and c.) Saturation curve to determine Kd and Bmax in SPA The saturation curve binding experiment is performed by adding varying amounts of [$^{125}$I]MIP1α (0-8.5 nM to membranes and beads in concentrations chosen from the optimal protein/bead ratio. The data is analyzed using a non-linear curve-fitting program. The $K_d$ and Bmax are derived from the curve.

Bacitracin 50 mg/ml is dissolved in deionized water, brought to a boil for 5 minutes (to destroy protease activity) and cooled. Prepared 1 ml aliquots and store at −80° C.

Protease inhibitor cocktail is prepared by dissolving 25 mg/ml of Pefabloc, 1 mg/ml of Leupeptin, 1 mg/ml of Aprotinin and 1 mg/ml of Pepstatin A in 100% DMSO. The cocktail can be aliquoted and stored frozen at −20° C. until needed.

Sigmacote: Any reagent bottles and reservoirs that come in contact with the radioligand are treated with Sigmacote to reduce sticking. Rinse containers with undiluted Sigmacote; rinse with deionized water several times, and allow to air dry before using.

Color Quench Assay-[$^{125}$I] SPA PVT color quench kit, Cat. No. RPAQ 4030, Amersham Ltd. A color quench curve is generated for each Packard TopCount and is stored in each counting protocol specific for the assay. This is done to prevent colored compounds from quenching the scintillation counts.

Compounds Preparation:

Compounds for a single concentration determination (One Shots) are delivered in 96 well Packard Optiplates containing 1 μl of compound in 100% DMSO in columns A1-H10 (80 compounds/plate). Column A11 to H11 is used for total binding (Bo) (vehicle-5 μl of the appropriate DMSO concentration) and column A12 to D12 is used for determination of nonspecific binding. No further preparation is required.

Compounds for concentration-response curves (10 points) are delivered in 96-Packard Optiplates containing 1 μl of compound in 100% DMSO in columns A1-H10. A 10-point concentration-response curve is desired for each compound with a starting high concentration of 30 μM (in the assay final). Column A11 to H11 is used for total binding (Bo) (vehicle-5 μl of the appropriate DMSO concentration) and column A12 to D12 is used for determination of nonspecific binding. No further preparation is required Materials:
1 M HEPES, pH 7.4, Gibco, Cat. No. 15360-080
Bacitracin, Sigma Catalog. Number. B-0125
Bovine Serum Albumin, Sigma, Cat. No. A-7888
$MgCl_2$, J. T. Baker-2444-01
$CaCl_2$, Sigma, Cat. No. C5080
MIP1α, Peprotech, Cat. No. 300-08
Sigmacote, Sigma, Cat. No. SL2
Scintillation Proximity Beads, Wheat Germ Agglutinin, Amersham, Cat No. RPNQ 0001
[$^{125}$I]MIP1α, NEN (#NEX298)
Packard 96 well flat-bottom Optiplate, Cat. No. 6005190
Falcon 96 well round-bottom plate, Cat. No. 3077
TOPSEAL-S, Packard, Cat. No. 6005161
Dimethyl Sulfoxide, EM Science, Cat. No. MX1458-6
Siliconized Pipette tips, Accutip, volume 200-1300 uL, Cat. No. P5048-85
Siliconized Pipette tips, Bio Plas, Inc., volume 1-200 uL, Cat. No. 60828-908
Reagent Reservoir, Elkay, Cat. No. 175-RBAS-000

Assay Buffer Preparation:
50 mM HEPES buffer pH 7.4, 1 mM $CaCl_2$, 5 mM MgCl2(this can be made ahead as a 100× stock), 1% BSA, 0.5 mg/ml Bacitracin, Protease inhibitor Cocktail (see preparation above) 100 uL/100 ml, DMSO is added to equal a final concentration of 2% per well (includes compound % DMSO) if needed.

Experimental Details:

[$^{125}$I]MIP1α preparation:
Prepared radioligand dilutions in container treated with Sigmacote
Reconstitute each 50 μCi vial with 0.5 ml of deionized water and store at 4° C.
Specific Activity=2,000 Ci/mmol
Add ~60,000 cpm (0.17 nM) to each assay well in 50 uL $B_o$:
Make a 20% DMSO solution and add 5uls of this to each well in col A11-H11. This gives a final 2% DMSO concentration for the well when added to the 1% in the assay buffer.

NSB:
Make a stock dilution of MIP1α at 100 uM using deionized water; aliquot and freeze. Dilute the MIP-1α stock solution to a concentration of 2 μM in the same 20% DMSO solution used above and add 5 μ to the wells in column A12 to D12 to give a final assay concentration of 100 nM. Prepare this in a Sigmacote-treated container Membrane and SPA Bead Preparation—

The final assay concentration for the membrane is 15 μg per well. SPA beads are prepared by adding 5 ml of assay buffer to a 500 mg vial. The final concentration of SPA beads in the assay is 0.25 mg/well. Membranes and beads are premixed as a 1:1 (membrane:bead) mixture and maintained at mixture at 4° C. with constant stirring. 50 μl of the mixture is added to each assay well. After all reagents have been added to the plates (total assay volume 100 μl), shake plates for 4 hours at room temperature. After 4 hours, place the plates on the TopCount in a count the plates on the TopCount for 30 sec per well using an appropriate program (i.e., one with a quench curve established for the conditions of the assay.

Data Reduction:

Data reduction is performed using the Microsoft Excel Addins Robofit or Robosage.

For single concentration assays (One Shots), the result of each test well is expressed as % inhibition using the following formula: 100*(1−(U1−C2)/(C1−C2)). Where U1 is the unknown sample in cpm observed in a particular well, C1 is the average of column 12 cpm observed in the absence of any added inhibitor, and C2 is the average of column 11 cpm observed in the presence of 1 μM of MIP1α.

For concentration-response assays, the result of each test well is expressed as % B/Bo (% total specific binding) using the following formula: 100*(U1−C2)/C1−C2). Curves were generated by plotting the % B/Bo versus the concentration and the $IC_{50}$ is derived using the equation $y=V_{max}*(1-(x^n/(k^n+x^n)))$.

Controls and Standards:

Each plate contains 12 wells of total binding (column A11-H11). The cpm/well are averaged and are used in data reduction as value C1. Each plate also contains 4 wells of non-specific binding (wells A12-D12). The counts of these wells are averaged and used in data reduction as value C2.

A standards plate is included in each experiment. This plate contains a 14-point concentration-response curve (in triplicate) for the standard compound MIP1α at a starting concentration of 1 μM. The average historical $pK_i$ obtained with MIP1α is 7.6.

The relevant biological response field for a single concentration (One Shots) is % inhibition. Inhibition values of >40 or >50% were considered positive responses.

The relevant biological response field for a concentration-response experiment is $pK_i$ HOS Assay (Also Referred to as HOS-LTR-Luciferase Assay)

Materials
DMEM (GibcoBRL # 10564-011)
Trpsin-EDTA (GibcoBRL #25300-054)
Heat inactivated Fetal Bovine Serum (FBS) (Hyclone # SH30070.03)
96-well, black-walled, clear-bottom, tissue culture-treated plates (Costar # 3904)
96-well, clear-walled, clear-bottom tissue culture-treated plates (Costar # 3598)
Phosphate Buffered Saline (PBS) (GibcoBRL #14190-144)
Dimethyl Sulfoxide (DMSO) (Sigma # D2650)
Luclite Luciferase Reporter assay (Packard #6016911)
HOS-CD4.CCR5-LTR-Luciferase (Bioresource Registration # 21164): Human Osteosarcoma cell line engineered to overexpress human CD4 and human CCR5 (AIDS Repository cat# 3318) stabily transfected with HIV-1-LTR-Luciferase reporter.

Advanced Preparation

Growth and Maintenance of the HOS-CD4.CCR5-LTR-Luciferase cell line: The cells were propagated in DMEM containing 2% FBS. Cells were split by standard trypsinization when confluency reached 80% (roughly every 2 to 3 days).

Titering of Virus Stocks:

HIV-1 virus stocks were titered in the assay system in order to obtain an estimate of the number of infectious particles per unit volume (described as RLU/ml). Virus stocks were diluted into DMEM containing 2% FBS and assayed as described in the "procedure" section below.

Procedure

Black-walled 96-well tissue culture plates were seeded with HOS-CD4.CCR5-LTR-Luciferase @ 0.6 to $1.2 \times 10^3$ cells per well in 50 ul DMEM containing 2% FBS and placed in a humidified incubator @ 37° C., 5% $CO_2$ overnight. The following day, test compounds were titrated 4-fold at 2× the final concentration in DMEM+2% FBS+ 0.2% DMSO. 50 μl of titrated compound was transferred to the HOS cells and the plates were placed in a humidified incubator at 37° C., 5% $CO_2$ for 1 hr. An additional 60 ul of 2× titrated compound was transferred to a clear-walled 96-well tissue culture plate and 60 ul of HIV (diluted to appropriate m.o.i.) was added to each well and thoroughly mixed. 100 ul of the HIV/compound mixture was transferred to the black-walled plates containing 100 ul of cells/compound. The plates were placed in a humidified incubator at 37° C., 5% $CO_2$ for 72 hr Following the 72 hour incubation, 150 ul of supernatant was removed and 50 ul of reconstituted LUCLITE (kit reagent) was added to each well. Each plate was sealed and read in a Topcount (Packard) luminometer at 1 s/well.

Data Reduction

Relative Light Units (RLU) were expressed as % control (RLU at drug [ ]/RLU no drug)*100=% Control $IC_{50}$ values were determined by any one of the following four nonlinear regression models:

$$y=V\mathrm{max}*(1-(x^n/(K^n+x^n)))+Y2$$

$$y=V\mathrm{max}*(1-(x^n/(K^n+x^n)))$$

$$y=V\mathrm{max}*(1-(x/(K+x)))+Y2$$

$$y=V\mathrm{max}*(1-(x/(K+x)))$$

Where: K is [$IC_{50}$, Y2 is baseline, and N is Hill Coefficient

Each of the compounds of the present invention provides a $pIC_{50}$ value of at least 5 when tested in each of the above-described assays.

Test compounds are employed in free or salt form.

All research complied with the principles of laboratory animal care (NIH publication No. 85-23, revised 1985) and standard pharmaceutical industry policy on animal use.

Although specific embodiments of the present invention have been illustrated and described in detail, the invention is not limited thereto. The above detailed description of preferred embodiments is provided for example only and should not be construed as constituting any limitation of the invention. Modifications will be obvious to those skilled in the art, and all modifications that do not depart from the spirit of the invention are intended to be included within the scope of the appended claims.

What is claimed is:
1. A compound or salt thereof selected from the group consisting of
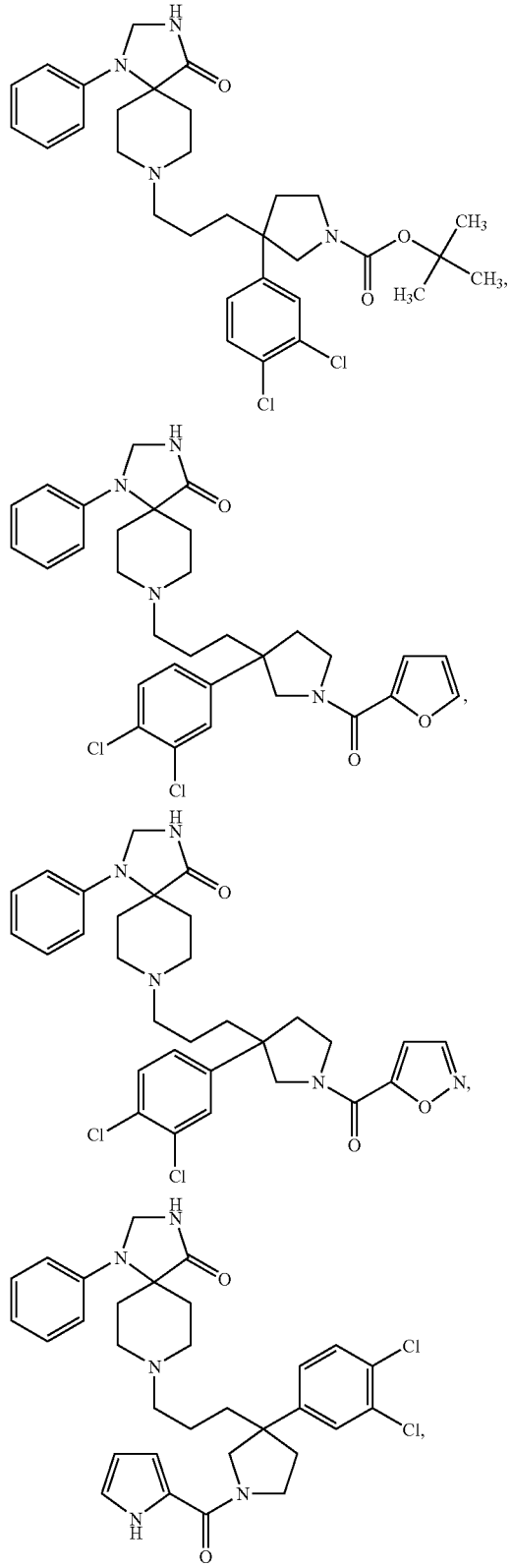
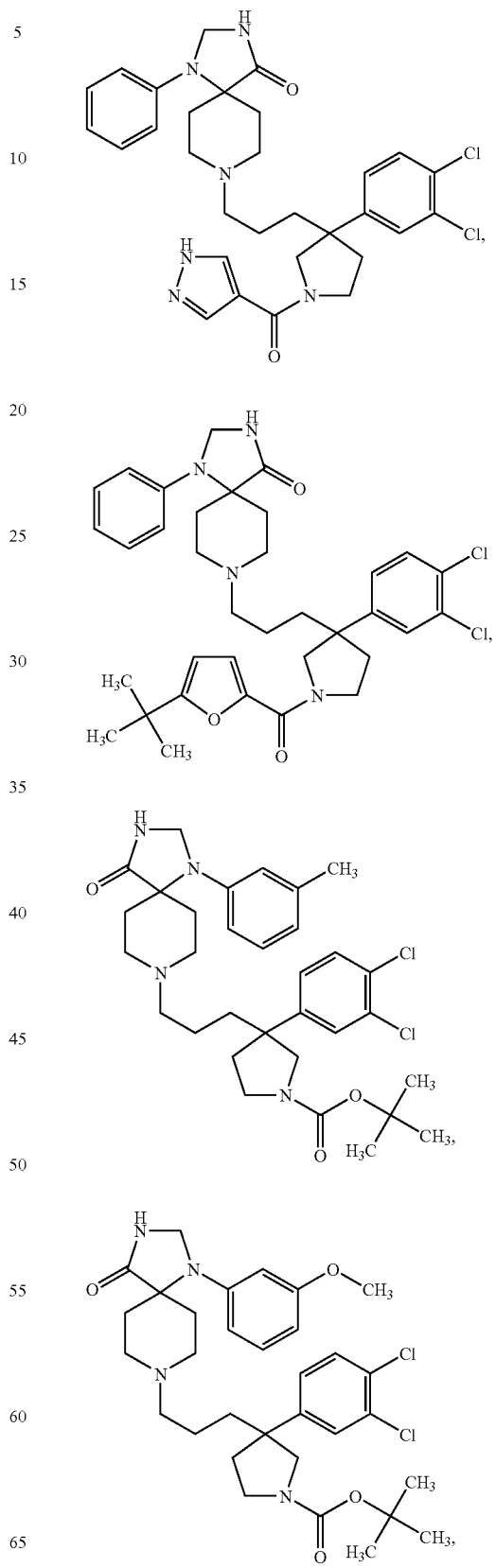

-continued
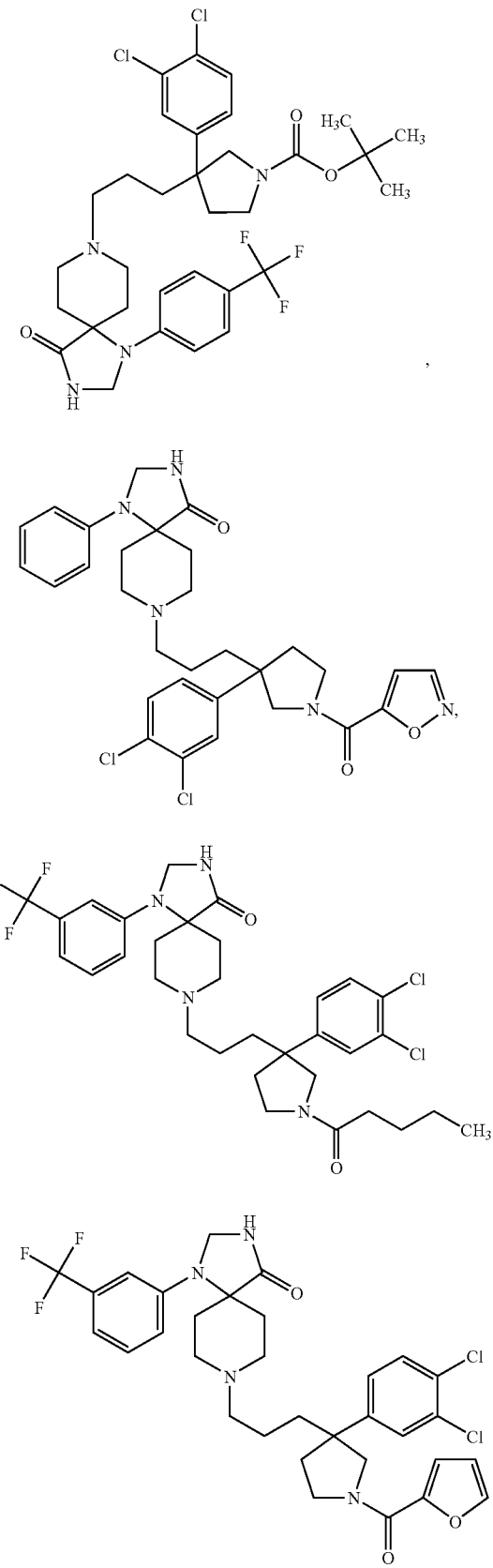
-continued
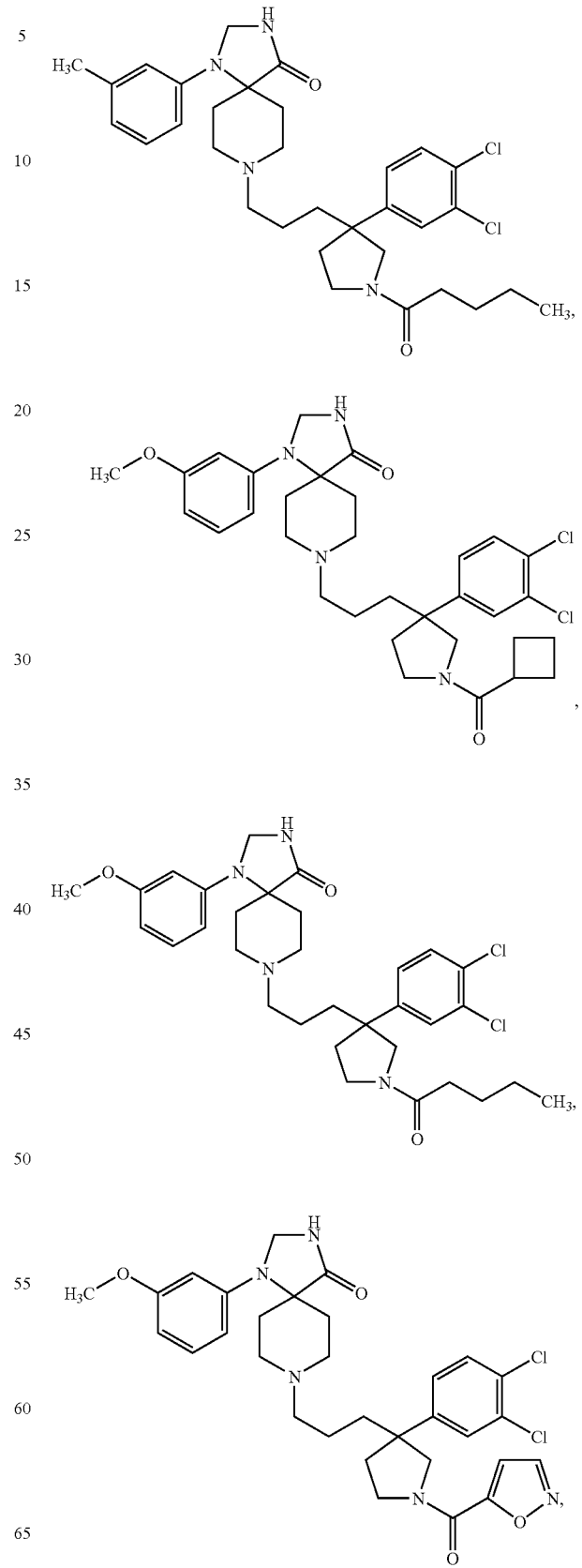

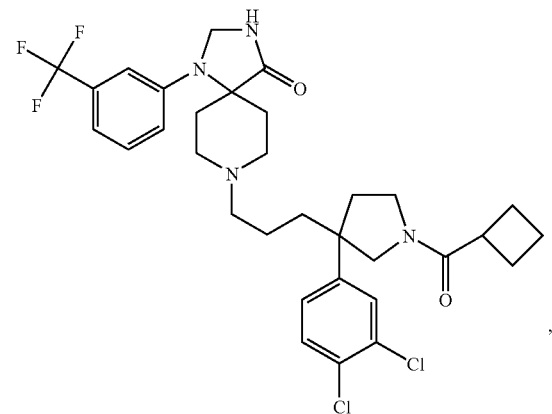
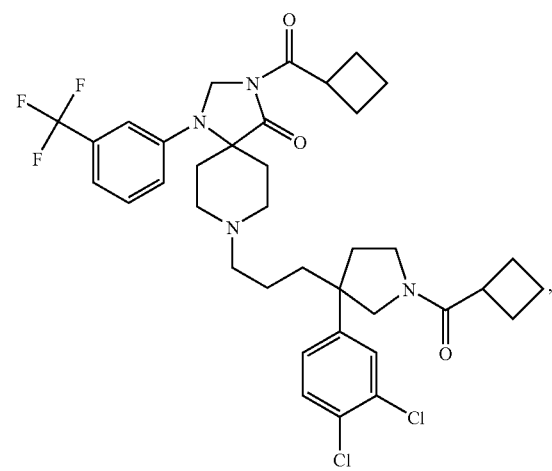
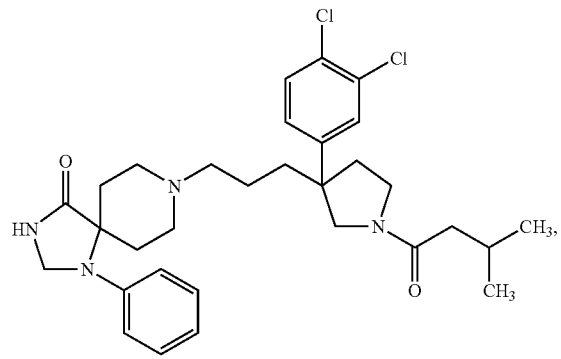
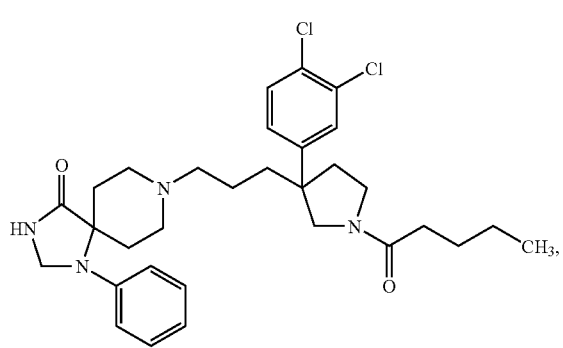
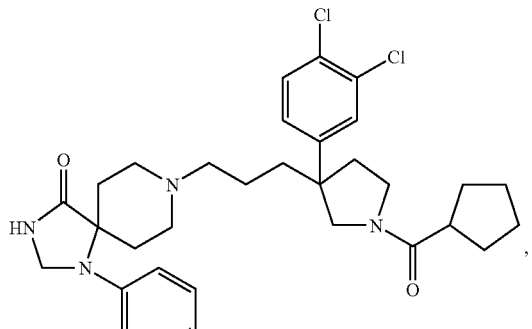
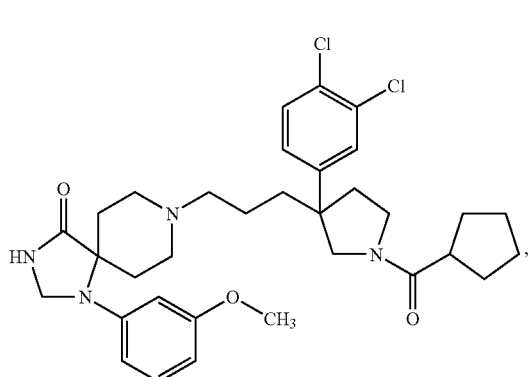
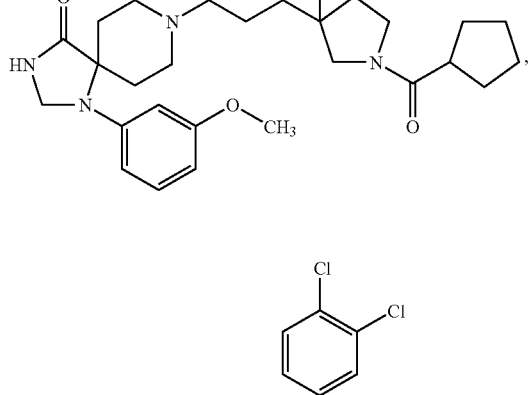
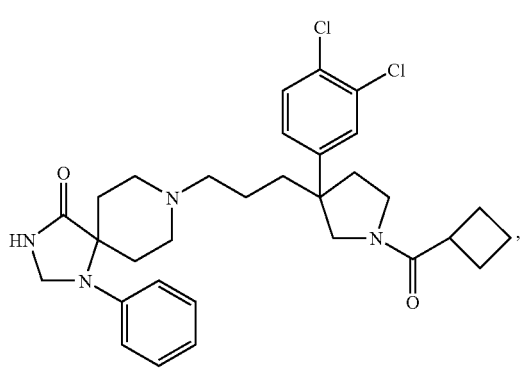
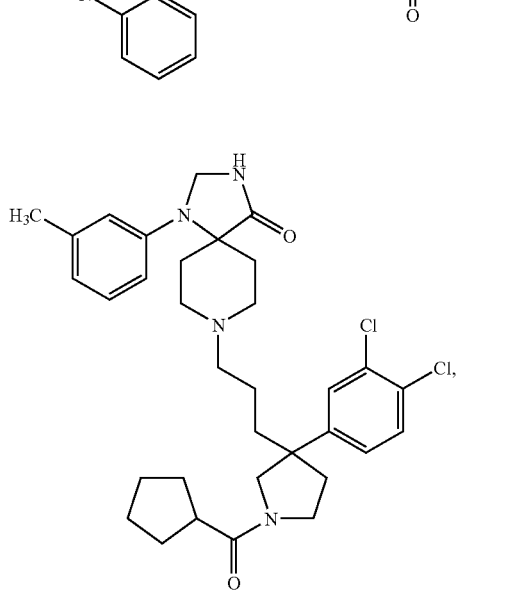

-continued
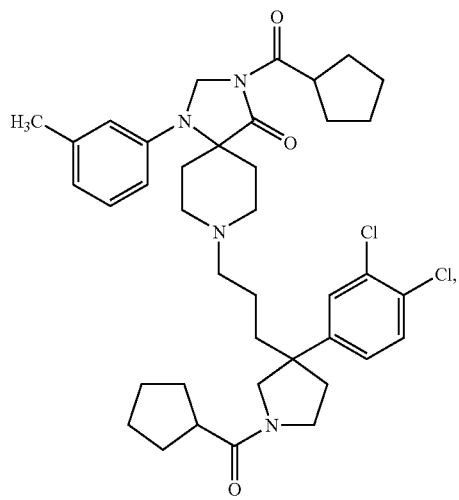
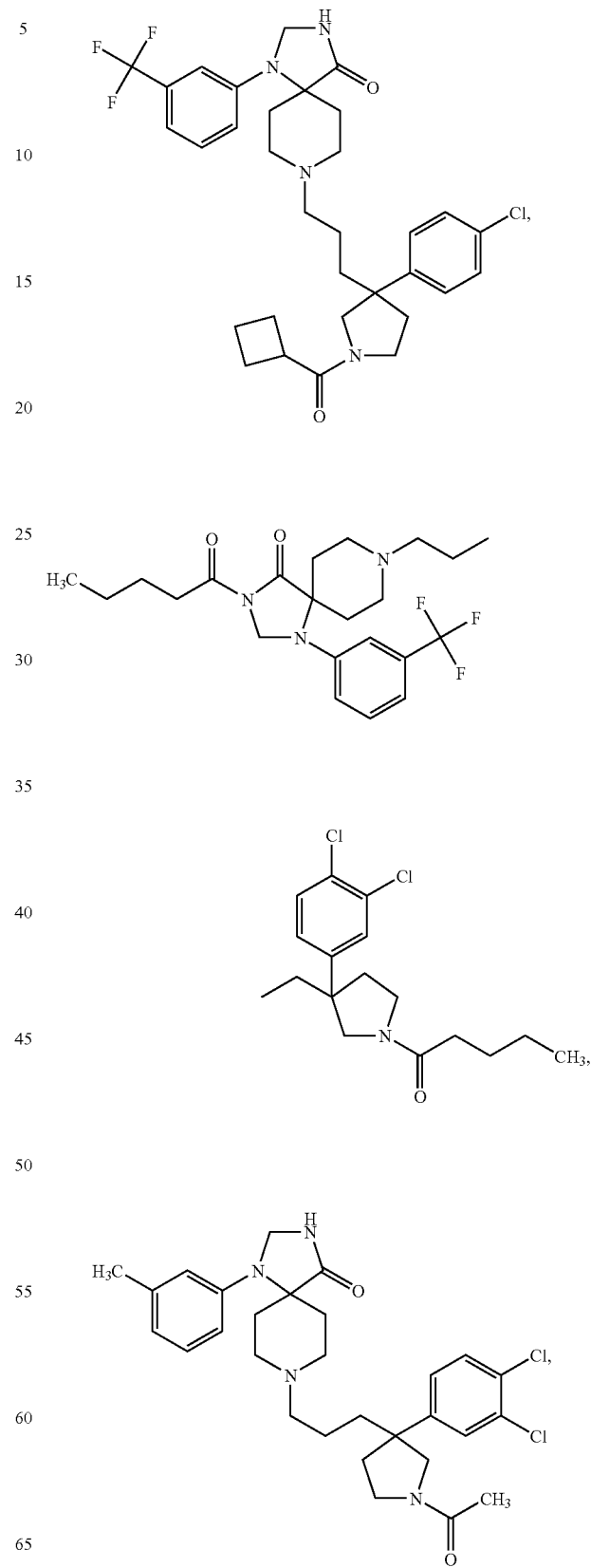

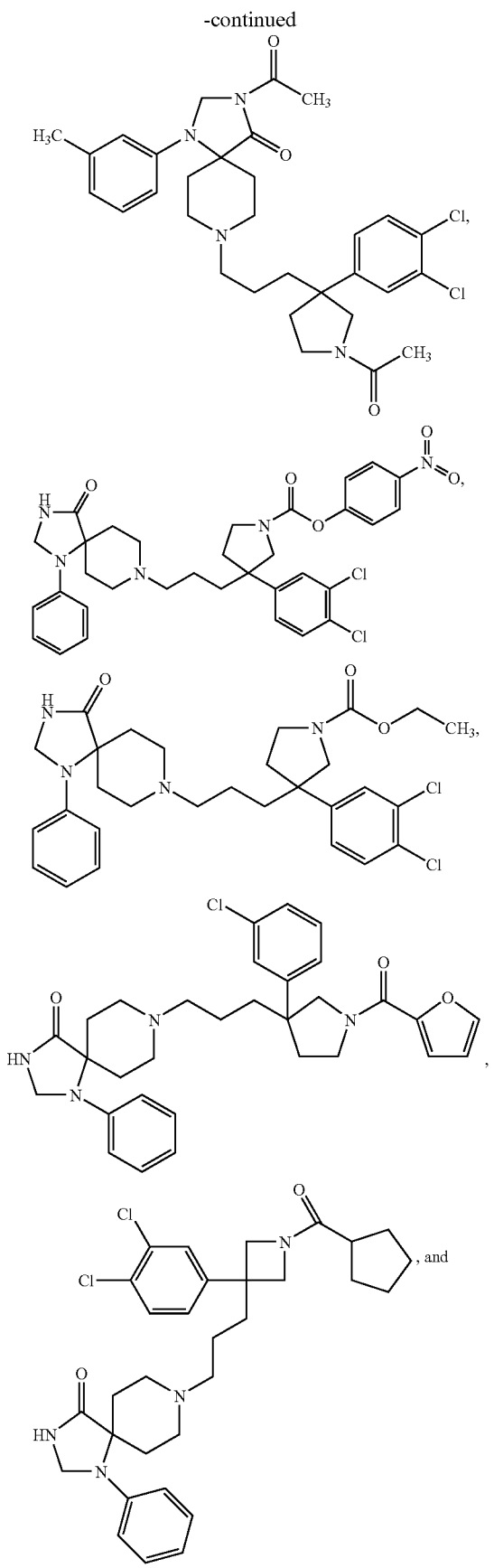

2. A compound selected from the group consisting of tert-butyl 3-(3,4-dichlorophenyl)-3-[3-(4-oxo-1-phenyl-1,3,8-triazaspiro[4.5]dec-8-yl)propyl]pyrrolidine-1-carboxylate;
8-{3-[3-(3,4-dichlorophenyl)-1-(2-furoyl)pyrrolidin-3-yl]propyl}-1-phenyl-1,3,8-triazaspiro[4.5]decan-4-one;
8-{3-[3-(3,4-dichlorophenyl)-1-(isoxazol-5-ylcarbonyl)pyrrolidin-3-yl]propyl}-1-phenyl-1,3,8-triazaspiro[4.5]decan-4-one;
8-{3-[3-(3,4-dichlorophenyl)-1-(1H-pyrrol-2-ylcarbonyl)pyrrolidin-3-yl]propyl}-1-phenyl-1,3,8-triazaspiro[4.5]decan-4-one;
8-{3-[3-(3,4-dichlorophenyl)-1-pentanoylpyrrolidin-3-yl]propyl}-1-[3-(trifluoromethyl)phenyl]-1,3,8-triazaspiro[4.5]decan-4-one;
8-{3-[3-(3,4-dichlorophenyl)-1-(2-furoyl)pyrrolidin-3-yl]propyl}-1-[3-(trifluoromethyl)phenyl]-1,3,8-triazaspiro[4.5]decan-4-one;
8-{3-[1-(cyclobutylcarbonyl)-3-(3,4-dichlorophenyl)pyrrolidin-3-yl]propyl}-1-[3-(trifluoromethyl)phenyl]-1,3,8-triazaspiro[4.5]decan-4-one;
8-{3-[3-(3,4-dichlorophenyl)-1-pentanoylpyrrolidin-3-yl]propyl}-1-phenyl-1,3,8-triazaspiro[4.5]decan-4-one;
8-{3-[1-(cyclopentylcarbonyl)-3-(3,4-dichlorophenyl)pyrrolidin-3-yl]propyl}-1-phenyl-1,3,8-triazaspiro[4.5]decan-4-one;
8-{3-[1-(cyclobutylcarbonyl)-3-(3,4-dichlorophenyl)pyrrolidin-3-yl]propyl}-1-phenyl-1,3,8-triazaspiro[4.5]decan-4-one;
8-{3-[1-(cyclobutylcarbonyl)-3-(3,4-dichlorophenyl)pyrrolidin-3-yl]propyl}-1-(3-methylphenyl)-1,3,8-triazaspiro[4.5]decan-4-one;
3-acetyl-8-{3-[1-acetyl-3-(3,4-dichlorophenyl)pyrrolidin-3-yl]propyl}-1-(3-methylphenyl)-1,3,8-triazaspiro[4.5]decan-4-one;
8-(2-{[3-(3,4-dichlorophenyl)-1-(2-furoyl)pyrrolidin-3-yl]oxy}ethyl)-1-phenyl-1,3,8-triazaspiro[4.5]decan-4-one;
8-(2-{[1-(cyclopentylcarbonyl)-3-(3,4-dichlorophenyl)pyrrolidin-3-yl]oxy}ethyl)-1-phenyl-1,3,8-triazaspiro[4.5]decan-4-one;
8-(2-{[1-acetyl-3-(3,4-dichlorophenyl)pyrrolidin-3-yl]oxy}ethyl)-1-phenyl-1,3,8-triazaspiro[4.5]decan-4-one;
8-(2-{[3-(3,4-dichlorophenyl)-1-(2-furoyl)pyrrolidin-3-yl]oxy}ethyl)-1-(3-methoxyphenyl)-1,3,8-triazaspiro[4.5]decan-4-one;

8-(2-{[1-(cyclopentylcarbonyl)-3-(3,4-dichlorophenyl)pyrrolidin-3-yl]oxy}ethyl)-1-(3-methoxyphenyl)-1,3,8-triazaspiro[4.5]decan-4-one; and 8-(2-{[1-acetyl-3-(3,4-dichlorophenyl)pyrrolidin-3-yl]oxy}ethyl)-1-(3-methoxyphenyl)-1,3,8-triazaspiro[4.5]decan-4-one.

3. A compound of formula (I)

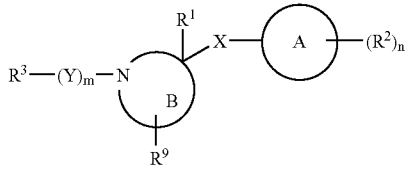

(I)

and pharmaceutically acceptable salts thereof, wherein

X is $(CH_2)_3$;

Ring A is a saturated, 6-membered monocyclic ring having one ring nitrogen;

Ring B is a saturated 4 or 5 membered ring containing the depicted ring nitrogen;

$R^1$ is a phenyl or a phenyl substituted with mono- or di-halogen;

Y is —C(O)— or —C(O)—O, and m is 1;

$R^3$ is H, —N$(R^0)_2$, —N$(R^0)$C(O)$R^0$, —CN, halogen, $CF_3$, alkyl optionally substituted by one or more groups selected from $R^7$ and —S-aryl optionally substituted by —$(CH_2)_{1-6}$—N$(R^0)SO_2(R^0)$, alkenyl optionally substituted by one or more groups selected from $R^7$ and —S-aryl optionally substituted by —$(CH_2)_{1-6}$—N$(R^0)SO_2(R^0)$, alkynyl optionally substituted by one or more groups selected from $R^7$ and —S-aryl optionally substituted by —$(CH_2)_{1-6}$—N$(R^0)SO_2(R^0)$, cycloalkyl or carbocyclyl optionally substituted by one or more $R^8$, or heterocyclyl optionally substituted by one or more $R^8$;

each $R^6$ is independently selected from halogen, —$CF_3$, —$OCF_3$, —$OR^0$, —$(CH_2)_{1-6}$—$OR^0$, —$SR^0$, —$(CH_2)_{1-6}$—$SR^0$, —$SCF_3$, —$R^0$, methylenedioxy, ethylenedioxy, —$NO_2$, —CN, —$(CH_2)_{1-6}$—CN, —N$(R^0)_2$, —$(CH_2)_{1-6}$—N$(R^0)_2$, —NR$^0$C(O)$R^0$, —NR$^0$(CN), —NR$^0$C(O)N$(R^0)_2$, —NR$^0$C(S)N$(R^0)_2$, —NR$^0$CO$_2R^0$, —NR$^0$NR$^0$C(O)$R^0$, —NR$^0$NR$^0$C(O)N$(R^0)_2$, —NR$^0$NR$^0$CO$_2R^0$, —C(O)C(O)$R^0$, —C(O)CH$_2$C(O)$R^0$, —$(CH_2)_{0-6}$—CO$_2R^0$, —O—C(O)$R^0$, —C(O)$R^0$, —C(O)N$(R^0)N(R^0)_2$, —C(O)N$(R^0)_2$, —C(O)N$(R^0)$OH, —C(O)N$(R^0)SO_2R^0$, —OC(O)N$(R^0)_2$, —S(O)$_tR^0$, —S(O)$_t$—OR$^0$, —S(O)$_tN(R^0)C(O)R^0$, —S(O)$_tN(R^0)OR^0$, —NR$^0$SO$_2$N$(R^0)_2$, —NR$^0$SO$_2R^0$, —C(=S)N$(R^0)_2$, —C(=NH)—N$(R^0)_2$, —$(CH_2)_{1-6}$—C(O)$R^0$, —C(=N—OR$^0$)—N$(R^0)_2$, —O—$(CH_2)_{0-6}$—SO$_2$N$(R^0)_2$, —$(CH_2)_{1-6}$—NHC(O)$R^0$, and —SO$_2$N$(R^0)_2$ wherein the two $R^0$s on the same nitrogen are optionally taken together to form a 5-8 membered saturated, partially saturated, or aromatic ring having additional 0-4 heteroatoms selected from oxygen, phosphorus, nitrogen, or sulfur;

each $R^7$ is independently selected from halogen, —$CF_3$, —$R^0$, —$OR^0$, —$OCF_3$, —$(CH_2)_{1-6}$—$OR^0$, —$SR^0$, —$SCF_3$, —$(CH_2)_{1-6}$—$SR^0$, aryl optionally substituted by $R^6$, methylenedioxy, ethylenedioxy, —$NO_2$, —CN, —$(CH_2)_{1-6}$—CN, —N$(R^0)_2$, —$(CH_2)_{1-6}$—N$(R^0)_2$, —NR$^0$C(O)$R^0$, —NR$^0$(CN), —NR$^0$C(O)N$(R^0)_2$, —N$(R^0)$C(S)N$(R^0)_2$, —NR$^0$CO$_2R^0$, —NR$^0$NR$^0$C(O)$R^0$, —NR$^0$NR$^0$C(O)N$(R^0)_2$, —NR$^0$NR$^0$CO$_2R^0$, —C(O)C(O)$R^0$, —C(O)CH$_2$C(O)$R^0$, —$(CH_2)_{0-6}$—CO$_2R^0$, —C(O)$R^0$, —C(O)N$(R^0)N(R^0)_2$, —C(O)N$(R^0)_2$, —C(O)N$(R^0)$OH, —OC(O)$R^0$, —C(O)N$(R^0)SO_2R^0$, —OC(O)N$(R^0)_2$, —S(O)$_tR^0$, —S(O)$_t$—OR$^0$, —S(O)$_tN(R^0)C(O)R^0$, —S(O)$_tN(R^0)OR^0$, —NR$^0$SO$_2$N$(R^0)_2$, —NR$^0$SO$_2R^0$, —C(=S)N$(R^0)_2$, —C(=NH)—N$(R^0)_2$, —$(CH_2)_{1-6}$—C(O)$R^0$, —C(=N—OR$^0$)—N$(R^0)_2$, —O—$(CH_2)_{0-6}$—SO$_2$N$(R^0)_2$, —$(CH_2)_{1-6}$—NHC(O)$R^0$, and —SO$_2$N$(R^0)_2$ wherein the two $R^0$s on the same nitrogen are optionally taken together to form a 5-8 membered saturated, partially saturated, or aromatic ring having additional 0-4 heteroatoms selected from oxygen, phosphorus, nitrogen, or sulfur;

each $R^8$ is independently selected from $R^7$, =O, =S, =N$(R^0)$, and =N(CN);

$R^9$ is H;

each $R^0$ is independently selected from hydrogen, alkyl, alkenyl, alkynyl, cycloalkyl, carbocyclylalkyl, aryl, heteroaryl, aralkyl, heteroaralkyl, heterocyclyl, or heterocyclylalkyl, wherein each member of $R^0$ except H is optionally substituted by one or more R*, OR*, N(R*)$_2$, =O, =S, halo, $CF_3$, $NO_2$, CN, —C(O)R*, —CO$_2$R*, —C(O)-aryl, —C(O)-heteroaryl, —C(O)-aralkyl, —S(O)$_t$-aryl, —S(O)$_t$-heteroaryl, —NR*SO$_2$R*, —NR*C(O)R*, —NR*C(O)N(R*)$_2$, —N(R*)C(S)N(R*)$_2$, —NR*CO$_2$R*, —NR*NR*C(O)R*, —NR*NR*C(O)N(R*)$_2$, —NR*NR*CO$_2$R*, —C(O)C(O)R*, —C(O)CH$_2$C(O)R*, —C(O)N(R*)N(R*)$_2$, —C(O)N(R*)$_2$, —C(O)NR*SO$_2$R*, —OC(O)N(R*)$_2$, —S(O)$_t$R*, —NR*SO$_2$N(R*)$_2$, —SO$_2$N(R*)$_2$ wherein the two R*s on the same nitrogen are optionally taken together to form a 5-8 membered saturated, partially saturated or aromatic ring having additional 0-4 heteroatoms selected from oxygen, phosphorus, nitrogen or sulfur;

each R* is independently H, alkyl, alkenyl, alkynyl, cycloalkyl, aryl, or heteroaryl.

4. The compound of claim 3 wherein the B ring is pyrrolidine.

5. The compound of claim 4 wherein $R^1$ is phenyl mono- or di-substituted with halogen.

6. The compound of claim 3 wherein $R^1$ is phenyl di-substituted with Cl.

7. The compound of claim 3 wherein m is 1, Y is —C(O)O—, and $R^3$ is optionally substituted alkyl or optionally substituted aryl.

8. The compound of claim 3 wherein the A ring, with an asterisk indicating the point of substitution, is

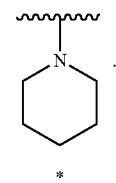

9. The compound of claim 3 wherein the A ring in combination with $R^2$ is selected from the group consisting of

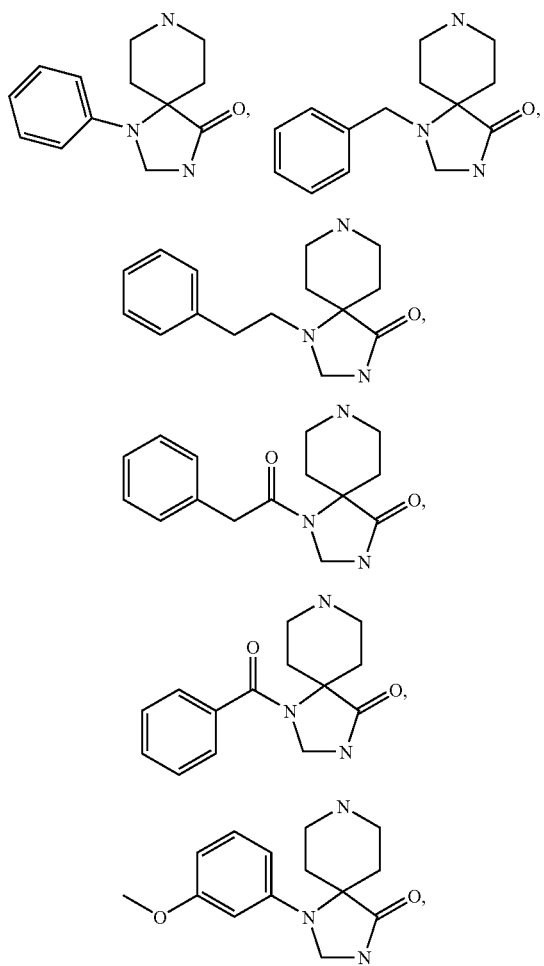
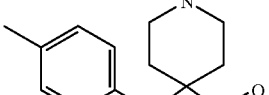
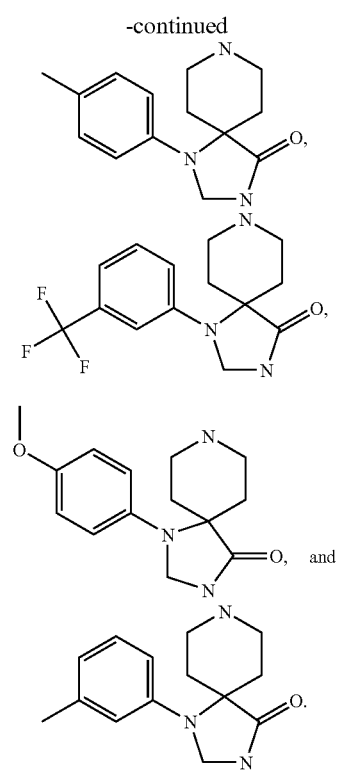
10. A pharmaceutical composition comprising a pharmaceutically effective amount of a compound according to claim 3 together with a pharmaceutically acceptable carrier.
11. The pharmaceutical composition according to claim 10 in the form of a tablet or capsule.
12. The pharmaceutical composition according to claim 10 in the form of a liquid.
* * * * *

UNITED STATES PATENT AND TRADEMARK OFFICE
CERTIFICATE OF CORRECTION

PATENT NO. : 7,271,172 B2
APPLICATION NO. : 10/538134
DATED : September 18, 2007
INVENTOR(S) : Yang et al.

It is certified that error appears in the above-identified patent and that said Letters Patent is hereby corrected as shown below:

In the Claims:

The chemical structure of Claim 3 (Column 115, Lines 10-15) should read as follows:

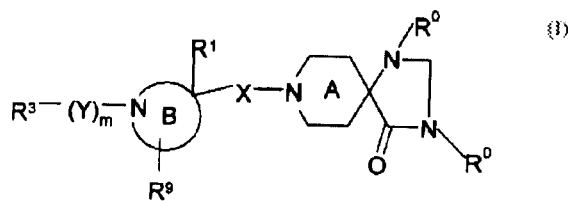

Claim 3 (Column 115, Line 40) should read as follows:

-- each $R^6$ is independently selected from the group consisting of halogen, -$CF_3$, --

Claim 3 (Column 115, Line 61) should read as follows:

-- each $R^7$ is independently selected from the group consisting of halogen, -$CF_3$, --

Claim 3 (Column 116, Lines 21-23) should read as follows:

-- each $R^0$ is independently selected from the group consisting of hydrogen, alkyl, alkenyl, alkynyl, cycloalkyl, carbocyclylalkyl, aryl, heteroaryl, aralkyl, heteroaralkyl, heterocyclyl, and het- --

UNITED STATES PATENT AND TRADEMARK OFFICE
CERTIFICATE OF CORRECTION

PATENT NO. : 7,271,172 B2
APPLICATION NO. : 10/538134
DATED : September 18, 2007
INVENTOR(S) : Yang et al.

It is certified that error appears in the above-identified patent and that said Letters Patent is hereby corrected as shown below:

Claim 5 (Column 116, Lines 46-47) should read as follows:

-- 5. The compound of claim 3 wherein $R^1$ is phenyl mono- or di-substituted with halogen. --

Signed and Sealed this

Fourth Day of March, 2008

JON W. DUDAS
*Director of the United States Patent and Trademark Office*